United States Patent
Roth et al.

(10) Patent No.: US 7,169,936 B2
(45) Date of Patent: Jan. 30, 2007

(54) INDOLINONE DERIVATIVES SUBSTITUTED IN THE 6-POSITION, THEIR PREPARATION AND THEIR USE AS MEDICAMENTS

(75) Inventors: Gerald Juergen Roth, Biberach (DE); Armin Heckel, Biberach (DE); Thorsten Lehmann-Lintz, Ochsenhausen (DE); Joerg Kley, Mittelbiberach (DE); Frank Hilberg, Wien (AT); Jacobus C. A. Van Meel, Moedling (AT); Ulrike Tontsch-Grunt, Baden (AT)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 424 days.

(21) Appl. No.: 10/625,101

(22) Filed: Jul. 22, 2003

(65) Prior Publication Data
US 2005/0043389 A1    Feb. 24, 2005

Related U.S. Application Data

(60) Provisional application No. 60/403,106, filed on Aug. 13, 2002.

(30) Foreign Application Priority Data

Jul. 23, 2002 (DE) ................. 102 33 366
Jun. 24, 2003 (DE) ................. 103 28 533

(51) Int. Cl.
*C07D 209/04* (2006.01)
(52) U.S. Cl. .................................. 548/491
(58) Field of Classification Search ........ 548/484, 548/491, 490, 469, 486
See application file for complete search history.

(56) References Cited

FOREIGN PATENT DOCUMENTS

| WO | WO 00/18734 | 4/2000 |
|---|---|---|
| WO | WO0018734 | 4/2000 |
| WO | WO 200018734 A1 * | 4/2000 |
| WO | WO0056710 | 9/2000 |
| WO | WO03026650 | 4/2003 |
| WO | WO03027102 | 4/2003 |
| WO | WO2004009547 | 1/2004 |

OTHER PUBLICATIONS

Copy of the International Search Report for PCT/EP 03/07961.
Copy of International Search Report for Reference #PCT/EP03/07960.
A. Heckel, et al; Indolinone derivatives substituted in the 6 position, the preparation thereof and their use as pharmaceutical compositions; U.S. Serial No. 10624983; Filed Jul. 22, 2003.
J. Park, et al; Medicaments for the treatment or prevention of fibrotic diseases; U.S. Serial No. 11275226; Filed Dec. 20, 2005.

* cited by examiner

*Primary Examiner*—Kamal A. Saeed
*Assistant Examiner*—Michael P. Barker
(74) *Attorney, Agent, or Firm*—Michael P. Morris; Mary-Ellen M. Devlin

(57) ABSTRACT

The present invention relates to indolinone derivatives, substituted in the 6-position, of the formula

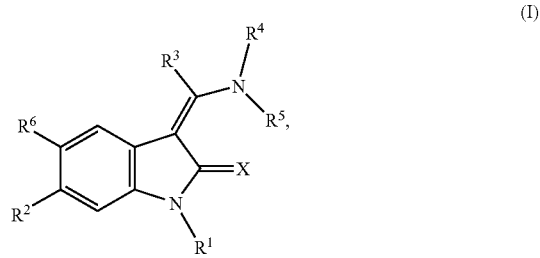

(I)

in which $R^1$ to $R^6$ and X are as defined in claim 1, to their tautomers, enantiomers, diastereomers, to their mixtures and to their salts, in particular their physiologically acceptable salts, which have useful pharmacological properties, in particular in inhibiting action on various receptor tyrosine kinases and on the proliferation of endothelial cells and various tumour cells, to medicaments comprising these compounds, to their use and to processes for their preparation.

4 Claims, No Drawings

INDOLINONE DERIVATIVES SUBSTITUTED IN THE 6-POSITION, THEIR PREPARATION AND THEIR USE AS MEDICAMENTS

RELATED APPLICATIONS

Benefit of U.S. Provisional Application Ser. No. 60/403,106, filed on Aug. 13, 2002, DE 10233366.1 filed Jul. 23, 2002, and DE 10328533.4, filed Jun. 24, 2003 are hereby claimed, and said applications are herein incorporated by reference.

The present invention relates to indolinone derivatives, substituted in the 6-position, of the formula

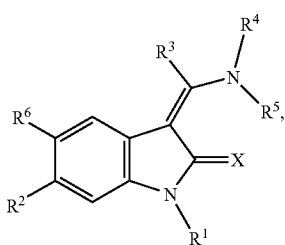

to their tautomers, enantiomers, diastereomers, their mixtures and their salts, in particular their physiologically acceptable salts, which have useful pharmacological properties, to medicaments comprising these compounds to their use and to processes for their preparation.

The above compounds of the formula I have useful pharmacological properties, in particular an inhibition action on various kinases, especially on receptor tyrosine kinases, such as VEGFR1, VEGFR2, VEGFR3, PDGFRα, PDGFRβ, FGFR1, FGFR3, EGFR, HER2, c-Kit, IGF1R and HGFR, Flt-3, and on the proliferation of cultivated human cells, in particular that of endothelial cells, for example in angiogenesis, but also on the proliferation of other cells, in particular tumour cells.

Accordingly, the present invention provides the above compounds of the formula I, which have useful pharmacological properties, medicaments comprising these pharmacologically active compounds, their use and processes for their preparation.

Moreover, the present invention provides the physiologically acceptable salts of the compounds according to the invention, medicaments comprising these compounds which in addition, if appropriate, contain one or more inert carrier materials and/or diluents, and their use for preparing a medicament suitable in particular for treating excessive or anormal cell proliferations.

The present invention furthermore provides processes for preparing this medicament, characterized in particular in that the compounds according to the invention or their physiologically acceptable salts are incorporated into one or more inert carrier materials and/or diluents.

I. In the above formula I,

X is an oxygen atom, $R^1$ is a hydrogen atom, $R^2$ is a fluorine, chlorine or bromine atom or a cyano group, $R^3$ is a phenyl group or a phenyl group which is mono-substituted by a fluorine, chlorine, bromine or iodine atom or by a $C_{1-3}$-alkoxy group, where the abovementioned unsubstituted and the monosubstituted phenyl groups may additionally be substituted in the 3- or 4-position by a fluorine, chlorine or bromine atom, by a cyano group, by a $C_{1-3}$-alkoxy or $C_{1-2}$-alkyl-carbonyl-amino group, by a cyano-$C_{1-3}$-alkyl, carboxy-$C_{1-3}$-alkyl, carboxy-$C_{1-4}$-alkoxy, carboxy-$C_{1-3}$-alkylamino, carboxy-$C_{1-3}$-alkyl-N-($C_{1-3}$-alkyl)-amino, $C_{1-4}$-alkoxy-carbonyl-$C_{1-3}$-alkyl, $C_{1-4}$-alkoxy-carbonyl-$C_{1-3}$-alkoxy, $C_{1-4}$-alkoxy-carbonyl-$C_{1-3}$-alkylamino, $C_{1-4}$-alkoxy-carbonyl-$C_{1-3}$-alkyl-N-($C_{1-3}$-alkyl)-amino, amino-$C_{1-3}$-alkyl, aminocarbonyl-$C_{1-3}$-alkyl, ($C_{1-2}$-alkylamino)-carbonyl-$C_{1-3}$-alkyl, di-($C_{1-2}$-alkyl)-aminocarbonyl-$C_{1-3}$-alkyl, ($C_{1-2}$-alkyl-carbonyl)-amino-$C_{1-3}$-alkyl, ($C_{1-4}$-alkoxy-carbonyl)-amino-$C_{1-3}$-alkyl, ($C_{3-6}$-alkyl-carbonyl)-amino-$C_{1-3}$-alkyl, (phenyl-carbonyl)-amino-$C_{1-3}$-alkyl, ($C_{3-6}$-cycloalkyl-carbonyl)-amino-$C_{1-3}$-alkyl, ($C_{3-6}$-cycloalkyl-$C_{1-3}$-alkyl-carbonyl)-amino-$C_{1-3}$-alkyl, (thiophen-2-yl-carbonyl)-amino-$C_{1-3}$-alkyl, (furan-2-yl-carbonyl)-amino-$C_{1-3}$-alkyl, (phenyl-$C_{1-3}$-alkyl-carbonyl)-amino-$C_{1-3}$-alkyl, (2-($C_{1-4}$-alkoxy)-benzoyl-carbonyl)-amino-$C_{1-3}$-alkyl, (pyridin-2-yl-carbonyl)-amino-$C_{1-3}$-alkyl, (pyridin-3-yl-carbonyl)-amino-$C_{1-3}$-alkyl-, (pyridin-4-yl-carbonyl)-amino-$C_{1-3}$-alkyl- or $C_{1-3}$-alkyl-piperazin-1-yl-carbonyl-$C_{1-3}$-alkyl group, by a carboxy-$C_{2-3}$-alkenyl, aminocarbonyl-$C_{2-3}$-alkenyl, ($C_{1-3}$-alkyl-amino)-carbonyl-$C_{2-3}$-alkenyl, di-($C_{1-3}$-alkyl)-amino-carbonyl-$C_{2-3}$-alkenyl or $C_{1-4}$-alkoxy-carbonyl-$C_{2-3}$-alkenyl group, where the substituents may be identical or different, $R^4$ is a phenyl group or a phenyl group which is mono-substituted by a $C_{1-3}$-alkyl group which is terminally substituted by an amino, guanidino, mono- or di-($C_{1-2}$-alkyl)-amino-, N-[ω-di-($C_{1-3}$-alkyl)-amino-$C_{2-3}$-alkyl]-N-($C_{1-3}$-alkyl)-amino, N-methyl-($C_{3-4}$-alkyl)-amino, N-($C_{1-3}$-alkyl)-N-benzylamino, N-($C_{1-4}$-alkoxycarbonyl)-amino, N-($C_{1-4}$-alkoxycarbonyl)-$C_{1-4}$-alkylamino, 4-($C_{1-3}$-alkyl)-piperazin-1-yl, imidazol-1-yl, pyrrolidin-1-yl, azetidin-1-yl, morpholin-4-yl, piperazin-1-yl, thiomorpholin-4-yl group, by a di-($C_{1-3}$-alkyl)-amino-($C_{1-3}$-alkyl)-sulphonyl, 2-[di-($C_{1-3}$-alkyl)-amino]-ethoxy, 4-($C_{1-3}$-alkyl)-piperazin-1-yl-carbonyl, {ω-[di-($C_{1-3}$-alkyl)-amino]-($C_{2-3}$-alkyl)}-N-($C_{1-3}$-alkyl)-amino-carbonyl, 1-($C_{1-3}$-alkyl)imidazol-2-yl, ($C_{1-3}$-alkyl)-sulphonyl group, or by a group of the formula

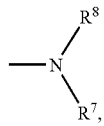

in which $R^7$ is a $C_{1-2}$-alkyl, $C_{1-2}$-alkyl-carbonyl, di-($C_{1-2}$-alkyl)-amino-carbonyl-$C_{1-3}$-alkyl or $C_{1-3}$-alkyl-sulphonyl group and $R^8$ is $C_{1-3}$-alkyl, ω-[di-($C_{1-2}$-alkyl)-amino]-$C_{2-3}$-alkyl, ω-[mono-($C_{1-2}$-alkyl)-amino]-$C_{2-3}$-alkyl group, or a ($C_{1-3}$-alkyl)-carbonyl, ($C_{4-6}$-alkyl)-carbonyl or carbonyl-($C_{1-3}$-alkyl) group which is terminally substituted by a di-($C_{1-2}$-alkyl)-amino, piperazin-1-yl or 4-($C_{1-3}$-alkyl)-piperazin-1-yl group, where all dialkylamino groups present in the radical $R^4$ may also be present in quaternized form, for example as an N-methyl-(N,N-dialkyl)-ammonium group, where the counterion is preferably selected from the group consisting of iodide, chloride, bromide, methylsulphonate, para-toluenesulphonate and trifluoroacetate, $R^5$ is a hydrogen atom and $R^6$ is a hydrogen atom, where the abovementioned alkyl groups include linear and branched alkyl groups in which additionally one to 3 hydrogen atoms may be replaced by fluorine atoms, where additionally a carboxyl, amino or imino group present may be substituted by an in vivo cleavable radical or may be present in the form of a prodrug radical, for example in the form of a group which can be converted in vivo into a carboxyl group or in the form of a group which can be converted in vivo into an imino or amino group, their tautomers, enantiomers, diastereomers, their mixtures and their salts.

II. Particularly preferred compounds of the above formula I are those compounds in which X, $R^1$, $R^5$ and $R^6$ are as defined under I. and:

II.i. $R^2$ and $R^4$ are as defined under I. and $R^3$ is a phenyl group or a phenyl group which is monosubstituted by a fluorine, chlorine, bromine or iodine atom or by a $C_{1-3}$-alkoxy group, where the abovementioned unsubstituted and the monosubstituted phenyl groups may additionally be substituted in the 3- or 4-position by a fluorine, chlorine or bromine atom, by a cyano group, by a $C_{1-3}$-alkoxy or $C_{1-2}$-alkyl-carbonyl-amino group, by a cyano-$C_{1-3}$-alkyl, carboxy-$C_{1-3}$-alkyl, carboxy-$C_{1-4}$-alkoxy, carboxy-$C_{1-3}$-alkylamino, carboxy-$C_{1-3}$-alkyl-N-($C_{1-3}$-alkyl)-amino, $C_{1-4}$-alkoxy-carbonyl-$C_{1-3}$-alkyl, $C_{1-4}$-alkoxy-carbonyl-$C_{1-3}$-alkoxy, $C_{1-4}$-alkoxy-carbonyl-$C_{1-3}$-alkylamino, $C_{1-4}$-alkoxy-carbonyl-$C_{1-3}$-alkyl-N-($C_{1-3}$-alkyl)-amino, amino-$C_{1-3}$-alkyl, aminocarbonyl-$C_{1-3}$-alkyl, ($C_{1-2}$-alkylamino)-carbonyl-$C_{1-3}$-alkyl, di-($C_{1-2}$-alkyl)-aminocarbonyl-$C_{1-3}$-alkyl, ($C_{1-2}$-alkyl-carbonyl)-amino-$C_{1-3}$-alkyl, ($C_{1-4}$-alkoxy-carbonyl)-amino-$C_{1-3}$-alkyl, ($C_{3-6}$-alkyl-carbonyl)-amino-$C_{1-3}$-alkyl, (phenyl-carbonyl)-amino-$C_{1-3}$-alkyl, ($C_{3-6}$-cycloalkyl-carbonyl)-amino-$C_{1-3}$-alkyl, ($C_{3-6}$-cycloalkyl-$C_{1-3}$-alkyl-carbonyl)-amino-$C_{1-3}$-alkyl, (thiophen-2-yl-carbonyl)-amino-$C_{1-3}$-alkyl, (furan-2-yl-carbonyl)-amino-$C_{1-3}$-alkyl, (phenyl-$C_{1-3}$-alkyl-carbonyl)-amino-$C_{1-3}$-alkyl, (2-($C_{1-4}$-alkoxy)-benzoyl-carbonyl)-amino-$C_{1-3}$-alkyl, (pyridin-2-yl-carbonyl)-amino-$C_{1-3}$-alkyl, (pyridin-3-yl-carbonyl)-amino-$C_{1-3}$-alkyl, (pyridin-4-yl-carbonyl)-amino-$C_{1-3}$-alkyl or $C_{1-3}$-alkyl-piperazin-1-yl-carbonyl-$C_{1-3}$-alkyl group, by a carboxy-$C_{2-3}$-alkenyl, aminocarbonyl-$C_{2-3}$-alkenyl-, ($C_{1-3}$-alkyl-amino)-carbonyl-$C_{2-3}$-alkenyl-, di-($C_{1-3}$-alkyl)-amino-carbonyl-$C_{2-3}$-alkenyl or $C_{1-4}$-alkoxy-carbonyl-$C_{2-3}$-alkenyl group, where the substituents may be identical or different;

II.ii. $R^2$ and $R^4$ are as defined under I. and $R^3$ is a phenyl group which is substituted by a $C_{1-2}$-alkyl-carbonyl-amino group, by a carboxy-$C_{1-3}$-alkyl, carboxy-$C_{1-4}$-alkoxy, $C_{1-4}$-alkoxy-carbonyl-$C_{1-3}$-alkyl, $C_{1-4}$-alkoxy-carbonyl-$C_{1-3}$-alkoxy, aminocarbonyl-$C_{1-3}$-alkyl, ($C_{1-2}$-alkylamino)-carbonyl-$C_{1-3}$-alkyl, di-($C_{1-2}$-alkyl)-aminocarbonyl-$C_{1-3}$-alkyl, ($C_{1-2}$-alkyl-carbonyl)-amino-$C_{1-3}$-alkyl, ($C_{1-4}$-alkoxy-carbonyl)-amino-$C_{1-3}$-alkyl, (phenyl-carbonyl)-amino-$C_{1-3}$-alkyl, ($C_{3-6}$-cycloalkyl-carbonyl)-amino-$C_{1-3}$-alkyl, ($C_{3-6}$-cycloalkyl-$C_{1-3}$-alkyl-carbonyl)-amino-$C_{1-3}$-alkyl, (thiophen-2-yl-carbonyl)-amino-$C_{1-3}$-alkyl, (furan-2-yl-carbonyl)-amino-$C_{1-3}$-alkyl, (phenyl-$C_{1-3}$-alkyl-carbonyl)-amino-$C_{1-3}$-alkyl, (2-($C_{1-4}$-alkoxy)-benzoyl-carbonyl)-amino-$C_{1-3}$-alkyl, (pyridin-2-yl-carbonyl)-amino-$C_{1-3}$-alkyl, (pyridin-3-yl-carbonyl)-amino-$C_{1-3}$-alkyl, (pyridin-4-yl-carbonyl)-amino-$C_{1-3}$-alkyl or $C_{1-3}$-alkyl-piperazin-1-yl-carbonyl-$C_{1-3}$-alkyl group, by an aminocarbonyl-$C_{2-3}$-alkenyl, ($C_{1-3}$-alkylamino)-carbonyl-$C_{2-3}$-alkenyl, di-($C_{1-3}$-alkyl)-amino-carbonyl-$C_{2-3}$-alkenyl or $C_{1-4}$-alkoxy-carbonyl-$C_{2-3}$-alkenyl group;

II.iii. $R^2$ and $R^4$ are as defined under I. and $R^3$ is a phenyl group substituted by a carboxy-$C_{1-3}$-alkyl or $C_{1-4}$-alkoxy-carbonyl-$C_{1-3}$-alkyl group;

II.iv. $R^3$ and $R^4$ are as defined under I. and $R^2$ is a fluorine or chlorine atom;

II.v. $R^2$ and $R^3$ are as defined under I. and $R^4$ is a phenyl group or a phenyl group which is monosubstituted by a $C_{1-3}$-alkyl group which is terminally substituted by an amino, guanidino, mono- or di-($C_{1-2}$-alkyl)-amino-, N-[ω-di-($C_{1-3}$-alkyl)-amino-$C_{2-3}$-alkyl]-N-($C_{1-3}$-alkyl)-amino, N-methyl-($C_{3-4}$-alkyl)-amino, N-($C_{1-3}$-alkyl)-N-benzylamino, N-($C_{1-4}$-alkoxycarbonyl)-amino, N-($C_{1-4}$-alkoxycarbonyl)-$C_{1-4}$-alkylamino, 4-($C_{1-3}$-alkyl)-piperazin-1-yl, imidazol-1-yl, pyrrolidin-1-yl, azetidin-1-yl, morpholin-4-yl, piperazin-1-yl, thiomorpholin-4-yl group, by a di-($C_{1-3}$-alkyl)-amino-($C_{1-3}$-alkyl)-sulphonyl, 2-[di-($C_{1-3}$-alkyl)-amino]-ethoxy, 4-($C_{1-3}$-alkyl)-piperazin-1-yl-carbonyl, {ω-[di-($C_{1-3}$-alkyl)-amino]-($C_{2-3}$-alkyl)}-N-($C_{1-3}$-alkyl)-amino-carbonyl, 1-($C_{1-3}$-alkyl)imidazol-2-yl, ($C_{1-3}$-alkyl)-sulphonyl group, or by a group of the formula

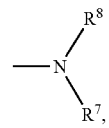

in which $R^7$ is a $C_{1-2}$-alkyl, $C_{1-2}$-alkyl-carbonyl, di-($C_{1-2}$-alkyl)-amino-carbonyl-$C_{1-3}$-alkyl or $C_{1-3}$-alkyl-sulphonyl group and $R^8$ is $C_{1-3}$-alkyl, ω-[di-($C_{1-2}$-alkyl)-amino]-$C_{2-3}$-alkyl, ω-[mono-($C_{1-2}$-alkyl)-amino]-$C_{2-3}$-alkyl group, or a ($C_{1-3}$-alkyl)-carbonyl, ($C_{4-6}$-alkyl)-carbonyl or carbonyl-($C_{1-3}$-alkyl) group which is terminally substituted by a di-($C_{1-2}$-alkyl)-amino, piperazin-1-yl or 4-($C_{1-3}$-alkyl)-piperazin-1-yl group, where all dialkylamino groups present in the radical $R^4$ may also be present in quaternized form, for example as an N-methyl-(N,N-dialkyl)-ammonium group, where the counterion is preferably selected from the group consisting of iodide, chloride, bromide, methylsulphonate, para-toluenesulphonate and trifluoroacetate.

III. Subgroups of particularly preferred compounds of the above formula I which are to be mentioned in particular are those in which:

III.i. X, $R^1$, $R^2$, $R^5$ and $R^6$ are as defined under I., $R^3$ is as defined under II.i. and $R^4$ is as defined under II.v.;

III.ii. X, $R^1$, $R^2$, $R^5$ and $R^6$ are as defined under I., $R^3$ is as defined under II.ii. and $R^4$ is as defined under II.v.;

III.iii. X, $R^1$, $R^2$, $R^5$ and $R^6$ are as defined under I., $R^3$ is as defined under II.iii. and $R^4$ is as defined under II.v.;

III.iv. X, $R^1$, $R^5$ and $R^6$ are as defined under I., $R^2$ is as defined under II.iv., $R^3$ is as defined under II.i., II.ii. or II.iii. and $R^4$ is as defined under II.v.

A further preferred group of compounds of the above formula I are those in which X is an oxygen atom, $R^1$ is a hydrogen atom, $R^2$ is a fluorine, chlorine or bromine atom or a cyano group, $R^3$ is a phenyl group or a phenyl group which is monosubstituted by a fluorine, chlorine, bromine or iodine atom or by a $C_{1-3}$-alkoxy group, where the abovementioned unsubstituted and the monosubstituted phenyl groups may additionally be substituted in the 3- or 4-position by a fluorine, chlorine or bromine atom, by a $C_{1-3}$-alkoxy or $C_{1-2}$-alkyl-carbonyl-amino group, by a carboxy-$C_{1-3}$-alkyl, aminocarbonyl-$C_{1-3}$-alkyl, ($C_{1-2}$-alkylamino)-carbonyl-$C_{1-3}$-alkyl, di-($C_{1-2}$-alkyl)-aminocarbonyl-$C_{1-3}$-alkyl, ($C_{1-2}$-alkyl-carbonyl)-amino-$C_{1-3}$-alkyl or (phenyl-carbonyl)-amino-$C_{1-3}$-alkyl group, where the substituents may be identical or different, $R^4$ is a phenyl group which is substituted by a $C_{1-3}$-alkyl group terminally substituted by a di-($C_{1-2}$-alkyl)-amino group, or by a group of the formula

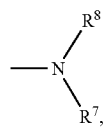

in which $R^7$ is a $C_{1-2}$-alkyl, $C_{1-2}$-alkyl-carbonyl, di-($C_{1-2}$-alkyl)-amino-carbonyl-$C_{1-3}$-alkyl or $C_{1-3}$-alkylsulphonyl group and $R^8$ is a $C_{1-3}$-alkyl or ω-[di-($C_{1-2}$-alkyl)-amino]-$C_{2-3}$-alkyl group, or a $C_{1-3}$-alkyl-carbonyl group terminally substituted by a di-($C_{1-2}$-alkyl)-amino, piperazino or 4-($C_{1-3}$-alkyl)-piperazin-1-yl group, $R^5$ is a hydrogen atom and $R^6$ is a hydrogen atom, where the abovementioned alkyl groups include linear and branched alkyl groups in which additionally one to 3 hydrogen atoms may be replaced by fluorine atoms, where additionally a carboxyl, amino or imino group present may be substituted by an in vivo cleavable radical, their tautomers, enantiomers, diastereomers, their mixtures and their salts.

The following compounds of the formula I are particularly preferred:

(a)  3-Z-[1-(4-dimethylaminomethylanilino)-1-(3-(2-carboxyethyl)phenyl)methylene]-6-chloro-2-indolinone (b)  3-Z-[1-(4-dimethylaminomethylanilino)-1-(4-(2-carboxyethyl)phenyl)methylene]-6-fluoro-2-indolinone (c)  3-Z-[1-(4-dimethylaminomethylanilino)-1-(3-(2-carboxyethyl)phenyl)methylene]-6-fluoro-2-indolinone (d)  3-Z-[1-(4-(N-(4-methylpiperazin-1-ylmethylcarbonyl)-N-methylamino)anilino)-1-(4-(2-carboxyethyl)phenyl)methylene]-6-fluoro-2-indolinone (e)  3-Z-[1-(4-(N-(2-dimethylaminoethyl)-N-methylsulphonylamino)anilino)-1-(4-(2-carboxyethyl)phenyl)methylene]-6-fluoro-2-indolinone (f)  3-Z-[1-(4-(N-(3-dimethylaminopropyl)-N-acetylamino)anilino)-1-(4-(2-carboxyethyl)phenyl)methylene]-6-fluoro-2-indolinone (g)  3-Z-[1-(4-(1-methylimidazol-2-yl)anilino)-1-(4-(2-carboxyethyl)phenyl)methylene]-6-fluoro-2-indolinone (h)  3-Z-[1-(4-(N-(dimethylaminomethylcarbonyl)-N-methylamino)anilino)-1-(4-(2-carboxyethyl)phenyl)methylene]-6-fluoro-2-indolinone (i) 3-Z-[1-(4-(N-(2-dimethylaminoethylcarbonyl)-N-methylamino)anilino)-1-(4-(2-carboxyethyl)phenyl)methylene]-6-fluoro-2-indolinone (j)  3-Z-[1-(4-(pyrrolidin-1-ylmethyl)anilino)-1-(4-(2-carboxyethyl)phenyl)methylene]-6-fluoro-2-indolinone (k)  3-Z-[1-(4-(diethylaminomethyl)anilino)-1-(4-(2-carboxyethyl)phenyl)methylene]-6-fluoro-2-indolinone (l)  3-Z-[1-(4-(2-dimethylaminoethyl)anilino)-1-(4-(2-carboxyethyl)phenyl)methylene]-6-chloro-2-indolinone (m)  3-Z-[1-(4-dimethylaminomethylanilino)-1-(4-(2-carboxyethyl)phenyl)methylene]-6-chloro-2-indolinone (n)  3-Z-[1-(4-(pyrrolidin-1-ylmethyl)anilino)-1-(4-(2-carboxyethyl)phenyl)methylene]-6-chloro-2-indolinone (o)  3-Z-[1-(4-(pyrrolidin-1-ylmethyl)anilino)-1-(4-(2-carboxyethyl)phenyl)methylene]-6-bromo-2-indolinone (p)  3-Z-[1-(4-(dimethylaminomethyl)anilino)-1-(4-(2-carboxyethyl)phenyl)methylene]-6-bromo-2-indolinone (q)  3-Z-[1-(4-(diethylaminomethyl)anilino)-1-(4-(2-carboxyethyl)-methylene]-6-bromo-2-indolinone where additionally a carboxyl, amino or imino group present may be substituted by an in vivo cleavable radical or may be present in the form of a prodrug radical, for example in the form of a group which can be converted in vivo into a carboxyl group or in the form of a group which can be converted in vivo into an imino or amino group, and their salts.

A group which can be converted in vivo into a carboxyl group is to be understood as meaning, for example, a hydroxymethyl group, a carboxyl group which is esterified with an alcohol in which the alcoholic moiety is preferably a $C_{1-6}$-alkanol, a phenyl-$C_{1-3}$-alkanol, a $C_{3-9}$-cycloalkanol, where a $C_{5-8}$-cycloalkanol may additionally be substitituted by one or two $C_{1-3}$-alkyl groups, a $C_{5-8}$-cycloalkanol in which one methylene group in the 3- or 4-position is replaced by an oxygen atom or by an imino group optionally substituted by a $C_{1-3}$-alkyl, phenyl-$C_{1-3}$-alkyl, phenyl-$C_{1-3}$-alkoxy-carbonyl or $C_{1-6}$-alkyl-carbonyl group and in which the cycloalkanol moiety may additionally be substituted by one or two $C_{1-3}$-alkyl groups, a $C_{4-7}$-cycloalkenol, a $C_{3-5}$-alkenol, a phenyl-$C_{3-5}$-alkenol, a $C_{3-5}$-alkynol or a phenyl-$C_{3-5}$-alkynol, with the proviso that no bond to the oxygen atom originates from a carbon atom which carries a double or triple bond, a $C_{3-8}$-cycloalkyl-$C_{1-3}$-alkanol, a bicycloalkanol having a total of 8 to 10 carbon atoms which may additionally be substituted in the bicycloalkyl moiety by one or two $C_{1-3}$-alkyl groups, a 1,3-dihydro-3-oxo-1-isobenzofuranol or an alcohol of the formula

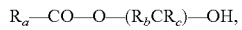

in which $R_a$ is a $C_{1-8}$-alkyl, $C_{5-7}$-cycloalkyl, phenyl or phenyl-$C_{1-3}$-alkyl group, $R_b$ is a hydrogen atom, a $C_{1-3}$-alkyl, $C_{5-7}$-cycloalkyl or phenyl group, and $R_c$ is a hydrogen atom or a $C_{1-3}$-alkyl group, and a radical cleavable in vivo from an imino or amino group is to be understood as meaning, for example, a hydroxyl group, an acyl group, such as the benzoyl or pyridinoyl group, or a $C_{1-16}$-alkylcarbonyl group, such as the formyl, acetyl, propionyl, butanoyl, pentanoyl or hexanoyl group, an allyloxycarbonyl group, a $C_{1-16}$-alkoxycarbonyl group, such as the methoxycarbonyl, ethoxycarbonyl, propoxycarbonyl, isopropoxycarbonyl, butoxycarbonyl, tert-butoxycarbonyl, pentoxycarbonyl, hexyloxycarbonyl, octyloxycarbonyl, nonyloxycarbonyl, decyloxycarbonyl, undecyloxycarbonyl, dodecyloxycarbonyl or hexadecyloxycarbonyl group, a phenyl-$C_{1-6}$-alkoxy-carbonyl group, such as the benzyloxycarbonyl, phenylethoxycarbonyl or phenylpropoxycarbonyl group, a $C_{1-3}$-alkylsulphonyl-$C_{1-4}$-alkoxycarbonyl, $C_{1-3}$-alkoxy-$C_{2-4}$-alkoxy-$C_{2-4}$-alkoxy-carbonyl or $R_aCO$—O—$(R_bCR_c)$—O—CO— group, in which $R_a$ is a $C_{1-8}$-alkyl, $C_{5-7}$-cycloalkyl, phenyl or phenyl-$C_{1-3}$-alkyl group, $R_b$ is a hydrogen atom, a $C_{1-3}$-alkyl, $C_{5-7}$-cycloalkyl or phenyl group and $R_c$ is a hydrogen atom, a $C_{1-3}$-alkyl or $R_aCO$—O—$(R_bCR_c)$—O— group, in which $R_a$ to $R_c$ are as defined above, and additionally, for an amino group, the phthalimido group, where the ester radicals mentioned above can also be used as a group which can be converted in vivo into a carboxyl group.

Preferred prodrug radicals for a carboxyl group are a $C_{1-6}$-alkoxy-carbonyl group, such as the methoxycarbonyl, ethoxycarbonyl, n-propyloxycarbonyl, isopropyloxycarbonyl, n-butyloxycarbonyl, n-pentyloxycarbonyl, n-hexyloxycarbonyl or cyclohexyloxycarbonyl group, or a phenyl-$C_{1-3}$-alkoxy-carbonyl group, such as the benzyloxycarbonyl group, and, for an imino or amino group, a $C_{1-9}$-alkoxy-carbonyl group, such as the methoxy-carbonyl, ethoxycarbonyl, n-propyloxycarbonyl, isopropyloxycarbonyl, n-butyloxy-carbonyl, n-pentyloxycarbonyl, n-hexyloxycarbonyl, cyclohexyloxycarbonyl, n-heptyloxycarbonyl, n-octyloxycarbonyl or n-nonyloxycarbonyl group, a phenyl-$C_{1-3}$-alkoxy-carbonyl group, such as the benzyloxycarbonyl group, a phenylcarbonyl group optionally substituted by a $C_{1-3}$-alkyl group, such as the benzoyl or 4-ethyl-benzoyl group, a pyridinoyl group, such as the nicotinoyl group, a $C_{1-3}$-alkylsulphonyl-n-$C_{2-3}$-alkoxy-carbonyl or $C_{1-3}$-alkoxy-$C_{2-3}$-alkoxy-$C_{1-4}$-alkoxy-carbonyl group, such as the 2-methylsulphonylethoxycarbonyl or 2-(2-ethoxy)-ethoxycarbonyl group.

According to the invention, the novel compounds are obtained, for example, by the following processes, which are known in principle from the literature:

a. reaction of a compound of the formula

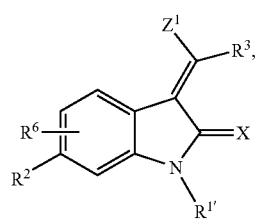

in which the radicals $Z^1$ and $R^3$ may, if appropriate, change their positions, X, $R^2$, $R^3$ and $R^6$ are as defined at the outset, $R^{1'}$ has the meanings mentioned at the outset for $R^1$ or is a protective group for the nitrogen atom of the lactam group, where $R^1$ may also, if appropriate, represent a bond, formed via a spacer, to a solid phase, and $Z^1$ is a halogen atom, a hydroxyl, alkoxy or arylalkoxy group, for example a chlorine or bromine atom, a methoxy, ethoxy or benzyloxy group, with an amine of the formula

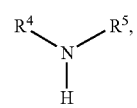

in which $R^4$ and $R^5$ are defined as mentioned at the outset, and, if required, the product is subsequently cleaved from a protective group used for the nitrogen atom of the lactam group or from a solid phase.

Suitable protective groups for the nitrogen atom of the lactam group are, for example, an acetyl, benzoyl, ethoxycarbonyl, tert-butyloxycarbonyl or benzyloxycarbonyl group and suitable solid phases are a resin, such as a 4-(2',4'-dimethoxyphenylaminomethyl)-phenoxy resin, where the attachment is expediently via the amino group, or a p-benzyloxybenzyl alcohol resin, where the attachment is expediently via a spacer, such as a 2,5-dimethoxy-4-hydroxybenzyl derivative.

The reaction is expediently carried out in a solvent, such as dimethylformamide, toluene, acetonitrile, tetrahydrofuran, dimethyl sulphoxide, methylene chloride or a mixture thereof, if appropriate in the presence of an inert base, such as triethylamine, N-ethyldiisopropylamine or sodium bicarbonate, at temperatures between 20 and 175° C., where any protective groups used may be simultaneously removed owing to transamidation.

If, in a compound of the formula V, $Z^1$ is a halogen atom, the reaction is preferably carried out in the presence of an inert base at temperatures between 20 and 120° C.

If, in a compound of the formula V, $Z^1$ is a hydroxyl, alkoxy or arylalkoxy group, the reaction is preferably carried out at temperatures between 20 and 200° C.

The subsequent removal of a protective group used, which may be required, if appropriate, is expediently carried out either hydrolytically in an aqueous or alcoholic solvent, for example in methanol/water, ethanol/water, isopropanol/water, tetrahydrofuran/water, dioxane/water, dimethylformamide/water, methanol or ethanol, in the presence of an alkali metal base, such as lithium hydroxide, sodium hydroxide or potassium hydroxide, at temperatures between 0 and 100° C., preferably at temperatures between 10 and 50° C., or, advantageously, by transamidation with an organic base, such as ammonia, butylamine, dimethylamine or piperidine, in a solvent, such as methanol, ethanol, dimethylformamide and mixtures thereof, or in an excess of the amine used, at temperatures between 0 and 100° C., preferably at temperatures between 10 and 50° C.

Cleavage from a solid phase employed is preferably carried out using trifluoroacetic acid and water at temperatures between 0 and 35° C., preferably at room temperature.

b. To prepare a compound of the formula I in which $R^3$ is a phenyl or naphthyl group substituted by a carboxy-$C_{2-3}$-alkenyl, aminocarbonyl-$C_{2-3}$-alkenyl, ($C_{1-3}$-alkylamino)-carbonyl-$C_{2-3}$-alkenyl, di-($C_{1-3}$-alkylamino)-carbonyl-$C_{2-3}$-alkenyl or $C_{1-4}$-alkoxy-carbonyl-$C_{2-3}$-alkenyl group, reaction of a compound of the formula

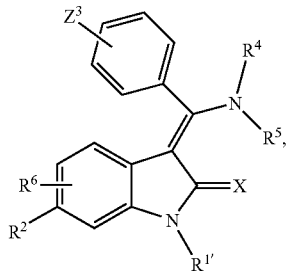

(IX)

in which
$R^2$, $R^4$, $R^5$, $R^6$ and X are as defined at the outset,
$R^{1'}$ has the meanings mentioned at the outset for $R^1$ or is a protective group for the nitrogen atom of the lactam group, where $R^{1'}$ may also, if appropriate, represent a bond, formed via a spacer, to a solid phase, and
$Z^3$ is a leaving group, for example a halogen atom or an alkyl- or arylsulphonyloxy group, such as a chlorine, bromine or iodine atom or a methylsulphonyloxy, ethylsulphonyloxy, p-toluenesulphonyloxy or trifluoromethanesulphonyloxy group, with an alkene of the formula

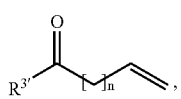

(X)

in which
$R^{3'}$ is an amino, ($C_{1-3}$-alkylamino), di-($C_{1-3}$-alkylamino) or $C_{1-4}$-alkoxy group and n is the number 0 or 1.

The reaction is expediently carried out with palladium catalysis, using, for example, palladium(II) acetate, palladium(II) chloride, bis(triphenylphosphine)palladium(II) acetate, bis(triphenylphosphine)palladium(II) chloride, palladium/carbon, bis-[1,2-bis(diphenylphosphino)ethane]palladium(0), dichloro-(1,2-bis(diphenylphosphino)-ethane) palladium(II), tetrakistriphenylphosphinepalladium(0), tris(dibenzylideneacetone)dipalladium(0), 1,1'-bis(diphenylphosphino)ferrocenedichloropalladium(II) or tris(dibenzylideneacetone)dipalladium(0)/chloroform adduct, in the presence of a base, such as triethylamine, diisopropylethylamine, lithium carbonate, potassium carbonate, sodium carbonate, caesium carbonate, and a ligand, such as triphenylphosphine, tri-ortho-tolylphosphine or tri-(tert-butyl)phosphine, in solvents such as acetonitrile, N-methylpyrrolidinone, dioxane or dimethylformamide and mixtures thereof.

The cleavage of a protective group used for the nitrogen atoms of the lactam group or from a solid phase, which may be required, if appropriate, is carried out as described above under process (a).

c. To prepare a compound of the formula I in which $R^3$ is a phenyl or naphthyl group substituted by
a carboxy-$C_{1-3}$-alkyl, $C_{1-4}$-alkoxy-carbonyl-$C_{1-3}$-alkyl, aminocarbonyl-$C_{1-3}$-alkyl, ($C_{1-3}$-alkylamino)-carbonyl-$C_{1-3}$-alkyl or di-($C_{1-3}$-alkyl)-aminocarbonyl-$C_{1-3}$-alkyl group, hydrogenation of a compound of the formula

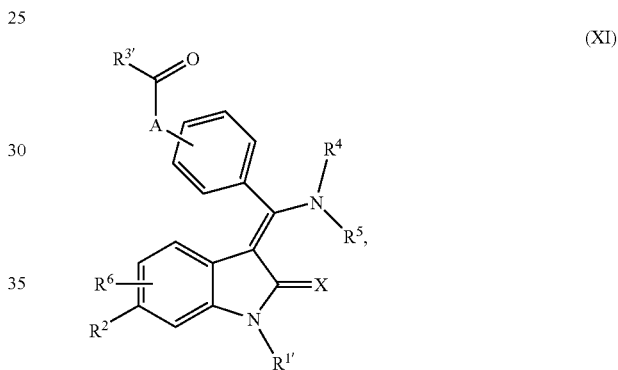

(XI)

in which
$R^2$, $R^4$, $R^5$, $R^6$ and X are as defined at the outset,
$R^{1'}$ has the meanings mentioned at the outset for $R^1$ or is a protective group for the nitrogen atom of the lactam group, where $R^{1'}$ may also, if appropriate, represent a bond, formed via a spacer, to a solid phase,
A is a $C_{2-3}$-alkenyl group and
$R^{3'}$ is a hydroxyl, $C_{1-4}$-alkoxy, amino, ($C_{1-3}$-alkylamino) or di-($C_{1-3}$-alkyl)amino group.

The hydrogenation is preferably carried out using catalytic hydrogenation with hydrogen in the presence of a catalyst, such as palladium/carbon or platinum, in a solvent, such as methanol, ethanol, ethyl acetate, dimethylformamide, dimethylformamide/acetone or glacial acetic acid, if appropriate with addition of an acid, such as hydrochloric acid, at temperatures between 0 and 50° C., but preferably at room temperature, and at a hydrogen pressure of 1 to 7 bar, but preferably 3 to 5 bar.

The cleavage of a protective group used for the nitrogen atom of the lactam group or from a solid phase, which may be required, if appropriate, is carried out as described under process (a).

If, according to the invention, a compound of the formula I is obtained which contains an alkoxycarbonyl group, this can be converted by hydrolysis into a corresponding carboxyl compound, or if a compound of the formula I is obtained which contains an amino or alkylamino group, this can be converted by reduction alkylation into a corresponding alkylamino or dialkylamino compound, or if a compound of the formula I is obtained which contains a dialkylamino group, this can be converted by alkylation into a corresponding trialkylammonium compound, or if a compound of the formula I is obtained which contains an amino or alkylamino group, this can be converted by acylation or sulphonation into a corresponding acyl or sulphonyl compound, respectively, or if a compound of the formula I is obtained which contains a carboxyl group, this can be converted by esterification or amidation into a corresponding ester or aminocarbonyl compound, respectively, or if a compound of the formula I is obtained which contains a nitro group, this can be converted by reduction into a corresponding amino compound, or if a compound of the formula I is obtained which contains a cyano group, this can be converted by reduction into a corresponding aminomethyl compound, or if a compound of the formula I is obtained which contains an arylalkyloxy group, this can be converted with acid into a corresponding hydroxyl compound, or if a compound of the formula I is obtained which contains an alkoxycarbonyl group, this can be converted by hydrolysis into a corresponding carboxyl compound, or if a compound of the formula I is obtained in which $R_4$ is a phenyl group substituted by an amino, alkylamino, aminoalkyl or N-alkylamino group, this can then be converted by reaction with a corresponding cyanate, isocyanate or carbamoyl halide into a corresponding urea compound of the formula I, or if a compound of the formula I is obtained in which $R_4$ is a phenyl group substituted by an amino, alkylamino, aminoalkyl or N-alkylamino group, this can subsequently be converted by reaction with a corresponding amidino-group-transferring compound or by reaction with a corresponding nitrile into a corresponding guanidino compound of the formula I.

The subsequent hydrolysis is preferably carried out in an aqueous solvent, for example in water, methanol/water, ethanol/water, isopropanol/water, tetrahydrofuran/water or dioxane/water, in the presence of an acid, such as trifluoroacetic acid, hydrochloric acid or sulphuric acid, or in the presence of an alkali metal base, such as lithium hydroxide, sodium hydroxide or potassium hydroxide, at temperatures between 0 and 100° C., preferably at temperatures between 10 and 50° C.

The subsequent reductive alkylation is preferably carried out in a suitable solvent, such as methanol, methanol/water, methanol/water/ammonia, ethanol, ether, tetrahydrofuran, dioxane or dimethylformamide, if appropriate with addition of an acid, such as hydrochloric acid, in the presence of catalytically activated hydrogen, for example of hydrogen in the presence of Raney nickel, platinum or palladium/carbon, or in the presence of a metal hydride, such as sodium borohydride, lithium borohydride, sodium cyanoborohydride or lithium aluminium hydride, at temperatures between 0 and 100° C., preferably at temperatures between 20 and 80° C.

The subsequent alkylation is preferably carried out in a suitable solvent, such as ether, tetrahydrofuran, dioxane, dichloromethane, acetone or acetonitrile, in the presence of alkylating agents, such as alkyl iodides, alkyl bromides, alkyl chlorides, methanesulphonic acid alkyl esters, para-toluenesulphonic acid alkyl esters or alkyl trifluoroacetates, at temperatures between 0 and 100° C., preferably at temperatures between 20 and 60° C.

The subsequent acylation or sulphonylation is expediently carried out using the corresponding free acid or a corresponding reactive compound, such as its anhydride, ester, imidazolide or halide, preferably in a solvent, such as methylene chloride, diethyl ether, tetrahydrofuran, toluene, dioxane, acetonitrile, dimethyl sulphoxide or dimethylformamide, if appropriate in the presence of an inorganic or a tertiary organic base, at temperatures between −20 and 200° C., preferably at temperatures between 20° C. and the boiling point of the solvent used. The reaction with the free acid can, if appropriate, be carried out in the presence of an agent which activates the acid or of a dehydrating agent, for example in the presence of isobutyl chloroformate, tetraethyl orthocarbonate, trimethyl orthoacetate, 2,2-dimethoxypropane, tetramethoxysilane, thionyl chloride, trimethylchlorosilane, phosphorus trichloride, phosphorus pentoxide, N,N'-dicyclohexylcarbodiimide, N,N'-dicyclohexylcarbodiimide/N-hydroxysuccinimide, N,N'-dicyclohexyl-carbodiimide/1-hydroxybenzotriazole, 2-(1H-benzotriazol-1-yl)-1,1,3,3-tetramethyluronium tetrafluoroborate, 2-(1H-benzotriazol-1-yl)-1,1,3,3-tetramethyluronium tetrafluoroborate/1-hydroxybenzotriazole, N,N'-carbonyldiimidazole or triphenylphosphine/carbon tetrachloride, and, if appropriate, with addition of a base, such as pyridine, 4-dimethylaminopyridine, N-methylmorpholine or triethylamine, expediently at temperatures between 0 and 150° C., preferably at temperatures between 0 and 100° C. The reaction with a corresponding reactive compound can, if appropriate, be carried out in the presence of a tertiary organic base, such as triethylamine, N-ethyl-diisopropylamine, N-methylmorpholine or pyridine, or, if an anhydride is used, in the presence of the corresponding acids, at temperatures between 0 and 150° C., preferably at temperatures between 50 and 100° C.

The subsequent esterification or amidation is expediently carried out by reacting a reactive corresponding carboxylic acid derivative with an appropriate alcohol or amine, as described above.

The esterification or amidation is preferably carried out in a solvent, such as methylene chloride, diethyl ether, tetrahydrofuran, toluene, dioxane, acetonitrile, dimethyl sulphoxide or dimethylformamide, if appropriate in the presence of an inorganic or a tertiary organic base, preferably at temperatures between 20° C. and the boiling point of the solvent used. Here, the reaction with a corresponding acid is preferably carried out in the presence of a dehydrating agent, for example in the presence of isobutyl chloroformate, tetraethyl orthocarbonate, trimethyl orthoacetate, 2,2-dimethoxypropane, tetramethoxysilane, thionyl chloride, trimethylchlorosilane, phosphorus trichloride, phosphorus pentoxide, N,N'-dicyclohexylcarbodiimide, N,N'-dicyclohexylcarbodiimide/N-hydroxysuccinimide, N,N'-dicyclohexylcarbodiimide/1-hydroxybenzotriazole, 2-(1H-benzotriazol-1-yl)-1,1,3,3-tetramethyluronium-tetrafluoroborate, 2-(1H-benzotriazol-1-yl)-1,1,3,3-tetramethyluronium-tetrafluoroborate/1-hydroxybenzotriazole, N,N'-carbonyldiimidazole or triphenyl-phosphine/carbon tetrachloride, and, if appropriate, with addition of a base, such as pyridine, 4-dimethylaminopyridine, N-methylmorpholine or triethylamine, expediently at temperatures between 0 and 150° C., preferably at temperatures between 0 and 100° C., and the acylation with a corresponding reactive compound, such as its anhydride, ester, imidazolide or halide, is, if appropriate, carried out in the presence of a tertiary organic base, such triethylamine, N-ethyldiisopropylamine or N-methylmorpholine, at temperatures between 0 and 150° C., preferably at temperatures between 50 and 100° C.

The subsequent reduction of a nitro group is preferably carried out hydrogenolytically, for example with hydrogen in the presence of a catalyst, such as palladium/carbon or Raney nickel, in a solvent, such as methanol, ethanol, ethyl acetate, dimethylformamide, dimethylformamide/acetone or glacial acetic acid, if appropriate with addition of an acid, such as hydrochloric acid or glacial acetic acid, at temperatures between 0 and 50° C., but preferably at room temperature, and at a hydrogen pressure of from 1 to 7 bar, but preferably from 3 to 5 bar.

The subsequent hydrogenation of a cyano group is preferably carried out hydrogenolytically, for example using hydrogen in the presence of a catalyst, such as palladium/carbon or Raney nickel, in a solvent, such as methanol, ethanol, ethyl acetate, methylene chloride, dimethylformamide, dimethylformamide/acetone or glacial acetic acid, if appropriate with addition of an acid, such as hydrochloric acid or glacial acetic acid, at temperatures between 0 and 50° C., but preferably at room temperature, and at a hydrogen pressure of from 1 to 7 bar, but preferably of from 3 to 5 bar.

The subsequent preparation of a corresponding guanidino compound of the formula I is expediently carried out by reaction with an amidino-group-transferring compound, such as 3,5-dimethylpyrazole-1-carboxamidine, preferably in a solvent, such as dimethylformamide, and, if appropriate, in the presence of a tertiary organic base, such as triethylamine, at temperatures between 0 and 50° C., preferably at room temperature.

In the reactions described above, any reactive groups present, such as carboxyl, hydroxyl, amino, alkylamino or imino groups, can be protected during the reaction by customary protective groups which are removed again after the reaction.

A protective radical for a carboxyl group is, for example, the trimethylsilyl, methyl, ethyl, tert-butyl, benzyl or tetrahydropyranyl group, and a protective group for a hydroxyl, amino, alkylamino or imino group is, for example, the acetyl, trifluoroacetyl, benzoyl, ethoxycarbonyl, tert-butoxycarbonyl, benzyloxycarbonyl, benzyl, methoxybenzyl or 2,4-dimethoxybenzyl group, and, for the amino group, additionally the phthalyl group.

The subsequent removal of a protective radical used is, if appropriate, carried out, for example, hydrolytically in an aqueous solvent, for example in water, isopropanol/water, tetrahydrofuran/water or dioxane/water, in the presence of an acid, such as trifluoroacetic acid, hydrochloric acid or sulphuric acid, or in the presence of an alkali metal base, such as lithium hydroxide, sodium hydroxide or potassium hydroxide, at temperatures between 0 and 100° C., preferably at temperatures between 10 and 50° C.

However, a benzyl, methoxybenzyl or benzyloxycarbonyl radical is removed, for example, hydrogenolytically, for example using hydrogen in the presence of a catalyst, such as palladium/carbon, in a solvent such as methanol, ethanol, ethyl acetate, dimethylformamide, dimethylformamide/acetone or glacial acetic acid, if appropriate with addition of an acid, such as hydrochloric acid or glacial acetic acid, at temperatures between 0 and 50° C., but preferably at room temperature, and at a hydrogen pressure of from 1 to 7 bar, but preferably of from 3 to 5 bar.

A methoxybenzyl group can also be removed in the presence of an oxidizing agent, such as cerium(IV) ammonium nitrate, in a solvent, such as methylene chloride, acetonitrile or acetonitrile/water, at temperatures between 0 and 50° C., but preferably at room temperature.

However, a 2,4-dimethoxybenzyl radical is preferably removed in trifluoroacetic acid in the presence of anisole.

A tert-butyl or tert-butyloxycarbonyl radical is preferably removed by treatment with an acid, such as trifluoroacetic acid or hydrochloric acid, using, if appropriate, a solvent, such as methylene chloride, dioxane, ethyl acetate or ether.

A phthalyl radical is preferably removed in the presence of hydrazine or a primary amine, such as methylamine, ethylamine or n-butylamine, in a solvent, such as methanol, ethanol, isopropanol, toluene/water or dioxane, at temperatures between 20 and 50° C.

Furthermore, chiral compounds of the formula I obtained can be separated into their enantiomers and/or diastereomers.

Thus, for example, compounds of the formula I obtained which occur as racemates can be separated by methods known per se (see Allinger N. L. and Eliel E. L. in "Topics in Stereochemistry", Vol. 6, Wiley Interscience, 1971) into their enantiomers, and compounds of the formula I having at least 2 asymmetric carbon atoms can, owing to their physicochemical differences, be separated by methods known per se, for example by chromatography and/or fractional crystallization, into their diastereomers, which, if they are obtained in racemic form, can then be separated into the enantiomers as mentioned above.

The separation of enantiomers is preferably carried out by column separation on chiral phases or by recrystallization from an optically active solvent or by reaction with an optically active substance which forms salts or derivatives, such as, for example, esters or amides, with the racemic compound, in particular acids and their activated derivatives or alcohols, and separating the mixture of diastereomeric salts or derivatives obtained in this manner, for example owing to different solubilities, whereupon the free enantiomers can be released from the pure diastereomeric salts or derivatives by action of suitable agents. Particularly common optically active acids are, for example, the D and L forms of tartaric acid, dibenzoyltartaric acid, di-o-tolyltartaric acid, malic acid, mandelic acid, camphorsulphonic acid, glutamic acid, N-acetylglutamic acid, aspartic acid, N-acetylaspartic acid or quinic acid. A suitable optically active alcohol is, for example, (+)- or (−)-menthol, and a suitable optically active acyl radical in amides is, for example, the (+)- or (−)-menthyloxycarbonyl radical.

Furthermore, the compounds of the formula I obtained can be converted into their salts, in particular, for pharmaceutical use, into their physiologically acceptable salts, with inorganic or organic acids. Acids suitable for this purpose are, for example, hydrochloric acid, hydrobromic acid, sulphuric acid, phosphoric acid, fumaric acid, succinic acid, lactic acid, citric acid, tartaric acid, maleic acid, methanesulphonic acid, ethanesulphonic acid, para-toluenesulphonic acid, phenylsulphonic acid or L-(+)-mandelic acid.

Moreover, the resulting novel compounds of the formula I can, if they contain a carboxyl group, then, if desired, be converted into their salts with inorganic or organic bases, in particular, for pharmaceutical use, into their physiologically acceptable salts. Bases suitable for this purpose are, for example, sodium hydroxide, potassium hydroxide, cyclohexylamine, ethanolamine, diethanolamine and triethanolamine.

Also suitable, for compounds of the formula I which contain 2 or more acidic or basic groups, are salts with 2 or more inorganic or organic bases or acids (disalts etc.).

Some of the compounds of the general formulae V to XI used as starting materials are known from the literature or can be obtained by processes known from the literature or can be obtained by the processes described above and in the examples. Compounds of the general formula IX, for example, are described in the German patent application 198 44 003.

As already mentioned at the outset, the novel compounds of the formula (I) have useful pharmacological properties, in particular in inhibiting action on various kinases, especially on receptor tyrosine kinases, such as VEGFR1, VEGFR2, VEGFR3, PDGFRα, PDGFRβ, FGFR1, FGFR3, EGFR, HER2, c-Kit, IGF1R and HGFR, Flt-3, and on the proliferation of cultivated human cells, in particular that of endothelial cells, for example in angiogenesis, but also on the proliferation of other cells, in particular of tumour cells.

The biological properties of the novel compounds were examined by the following standard methods:

Human umbilical cord endothelial cells (HUVEC) were cultivated in IMDM (Gibco BRL), supplemented with 10% foetal bovine serum (FBS) (Sigma), 50 µM β-mercaptoethanol (Fluka), standard antibiotics, 15 µg/ml of endothelial cell growth factor (ECGS, Collaborative Biomedical Products) and 100 µg/ml of heparin (Sigma) on gelatin-coated culture bottles (0.2% gelatin, Sigma) at 37° C., 5% $CO_2$, in an atmosphere saturated with water.

To examine the inhibitory activity of the compounds according to the invention, the cells were "starved" for 16 hours, i.e. kept in culture medium without growth factors (ECGS+heparin). Using trypsin/EDTA, the cells were detached from the culture bottles and washed once with serum-containing medium. $2.5 \times 10^3$ cells were then seeded in each well.

The proliferation of the cells was stimulated using 5 ng/ml of $VEGF_{165}$ (vascular endothelial growth factor; H. Weich, GBF Brunswick) and 10 µg/ml of heparin. Per plate, as control value, in each case 6 wells were not stimulated.

The compounds according to the invention were dissolved in 100% dimethyl sulphoxide and, in triplicate, added to the cultures in different dilutions, the maximum dimethyl sulphoxide concentration being 0.3%.

The cells were incubated at 37° C. for 76 hours, and $^3$H-thymidine (0.1 µCi/well, Amersham) was then added for a further 16 hours to determine DNA synthesis. The radioactively labelled cells were then immobilized on filter mats and the incorporated radioactivity was determined in a β counter. To determine the inhibitory activity of the compounds according to the invention, the mean value for the non-stimulated cells was subtracted from the mean value of the factor-stimulated cells (in the presence or absence of the compounds according to the invention).

The relative cell proliferation was calculated in percent of the control (HUVEC without inhibitor), and the concentration of active compound at which the proliferation of the cells is inhibited by 50% ($IC_{50}$) was derived therefrom.

The compounds of the formula I according to the invention have an $IC_{50}$ between 50 µM and 1 nM.

Owing to their inhibitory action on the proliferation of cells, in particular of endothelian cells and of tumour cells, the compounds of the formula I are suitable for treating diseases in which the proliferation of cells, in particular that of endothelial cells, plays a role.

Thus, for example, the proliferation of endothelial cells and the related neovascularization is a decisive step in tumour progression (Folkman J. et al., Nature 339, 58–61, (1989); Hanahan D. and Folkman J., Cell 86, 353–365, (1996)). Furthermore, the proliferation of endothelial cells is also of importance in haemangiomes, in metastasization, in rheumatoid arthritis, in psoriasis and in ocular neovascularization (Folkman J., Nature Med. 1, 27–31, (1995); Carmeliet P & Rakeh J., Nature 407, 249–257, (2000)). The therapeutic benefit of inhibitors of endothelial cell proliferation in the animal model was shown, for example, by O'Reilly et al. and Parangi et al. (O'Reilly M. S. et al., Cell 88, 277–285, (1997); Parangi S. et al., Proc Natl Acad Sci USA 93, 2002–2007, (1996)).

Thus, the compounds of the formula I, their tautomers, their stereoisomers or their physiologically acceptable salts are suitable, for example, for treating tumours (for example squamous epithelium carcinoma, astrocytoma, Kaposi sarcoma, glioblastoma, lung cancer, cancer of the bladder, neck carcinoma, oesophagus carcinoma, melanoma, ovarial carcinoma, prostate carcinoma, breast cancer, small-cell lung carcinoma, glioma, colorectal carcinoma, pancreas carcinoma, urogenital cancer and gastrointestinal carcinoma, and also haematological cancers, such as, for example, multiple myeloma and acute myelotic leukaemia), psoriasis, arthritis (for example rheumatoid arthritis), haemangioma, angiofibroma, disorders of the eye (for example diabetic retinopathy), neovascular glaucoma, disorders of the kidneys (for example glomerulonephritis), diabetic nephropathy, malignant nephrosclerosis, thrombic microangiopathic syndromes, transplantation rejections and glomerulopathy, fibrotic disorders (for example cirrhosis of the liver), mesangial-cell-proliferative disorders, atherosclerosis, injuries of the nerve tissue and for inhibiting the reocclusion of vessels after balloon catheter treatment, in vessel prosthetics or after implantation of mechanical devices for keeping vessels open (for example stents) or other disorders in which cell proliferation or angiogenesis play a role.

Owing to their biological properties, the compounds according to the invention can be used alone or in combination with other pharmacologically active compounds, for example in tumour therapy in monotherapy or in combination with other antitumor therapeutics, for example in combination with topoisomerase inhibitors (for example etoposide), mitosis inhibitors (for example vinblastine, Taxol), compounds which interact with nucleic acids (for example cisplatin, cyclophosphamide, adriamycin), hormone antagonists (for example tamoxifen), steroids and analogues thereof (for example dexamethasone), inhibitors of metabolic processes (for example 5-FU etc.), cytokines (for example interferons), kinase inhibitors (for example EGFR kinase inhibitoren, such as, for example, Iressa; Gleevec), allosterically acting receptor tyrosine kinase inhibitors, antibodies (for example Herceptin), COX-2 inhibitors or else in combination with radiotherapy, etc. These combinations can be administered either simultaneously or sequentially.

The invention is illustrated in more detail by the examples below:

| Example | Name |
|---|---|
| 1.0 | 3-Z-[1-(4-(N-methyl-N-methylsulphonylamino)anilino)-1-(3-iodophenyl)-methylene]-6-chloro-2-indolinone |
| 1.1 | 3-Z-[1-(4-(dimethylaminomethyl)anilino)-1-(3-iodophenyl)methylene]-6-chloro-2-indolinone |
| 1.2 | 3-Z-[1-(4-(N-(dimethylaminomethylcarbonyl)-N-methylamino)anilino)-1-(4-chlorophenyl)methylene]-6-chloro-2-indolinone |
| 1.3 | 3-Z-[1-(4-(N-(2-dimethylaminoethyl)-N-acetylamino)anilino)-1-(4-chlorophenyl)methylene]-6-chloro-2-indolinone |
| 1.4 | 3-Z-[1-(4-(N-(4-methylpiperazin-1-ylmethylcarbonyl)-N-methylamino)anilino)-1-(4-chlorophenyl)methylene]-6-chloro-2-indolinone |
| 1.5 | 3-Z-[1-(4-(N-(3-dimethylaminopropyl)-N-acetylamino)anilino)-1-(4-chlorophenyl)methylene]-6-chloro-2-indolinone |
| 1.6 | 3-Z-[1-(4-(dimethylaminomethyl)anilino)-1-(4-chlorophenyl)methylene]-6-chloro-2-indolinone |
| 1.7 | 3-Z-[1-(4-(N-(2-dimethylaminoethyl)-N-acetylamino)anilino)-1-(3,4-dimethoxyphenyl)methylene]-6-chloro-2-indolinone |
| 1.8 | 3-Z-[1-(4-(N-(4-methylpiperazin-1-ylmethylcarbonyl)-N-methylamino)anilino)-1-(3,4-dimethoxyphenyl)methylene]-6-chloro-2-indolinone |
| 1.9 | 3-Z-[1-(4-(N-(2-dimethylaminoethyl)-N-methylsulphonylamino)anilino)-1-(3,4-dimethoxyphenyl)methylene]-6-chloro-2-indolinone |
| 1.10 | 3-Z-[1-(4-(dimethylaminomethyl)anilino)-1-(3,4-dimethoxyphenyl)-methylene]-6-chloro-2-indolinone |
| 1.11 | 3-Z-[1-(4-(N-(2-dimethylaminoethyl)-N-methylcarbamoyl)anilino)-1-(3,4-dimethoxyphenyl)methylene]-6-chloro-2-indolinone |
| 2.0 | 3-Z-[1-(4-(dimethylaminomethyl)anilino)-1-(4-cyanophenyl)-methylene]-6-chloro-2-indolinone |
| 3.0 | 3-Z-[1-(4-(dimethylaminomethyl)anilino)-1-(4-iodophenyl)methylene]-6-fluoro-2-indolinone |
| 3.1 | 3-Z-[1-(4-(dimethylaminomethyl)anilino)-1-(3-fluorophenyl)methylene]-6-fluoro-2-indolinone |
| 3.2 | 3-Z-[1-(4-(N-(3-dimethylaminopropyl)-N-acetylamino)anilino)-1-(3-fluorophenyl)methylene]-6-fluoro-2-indolinone |
| 3.3 | 3-Z-[1-(4-(N-(4-methylpiperazin-1-ylmethylcarbonyl)-N-methylamino)anilino)-1-(3-fluorophenyl)methylene]-6-fluoro-2-indolinone |
| 3.4 | 3-Z-[1-(4-(dimethylaminomethyl)anilino)-1-(4-(2-acetylaminoethyl)phenyl)methylene]-6-fluoro-2-indolinone |
| 3.5 | 3-Z-[1-(4-(N-(3-dimethylaminopropyl)-N-acetylamino)anilino)-1-(4-(2-acetylaminoethyl)phenyl)methylene]-6-fluoro-2-indolinone |
| 3.6 | 3-Z-[1-(4-(N-(4-methylpiperazin-1-ylmethylcarbonyl)-N-methylamino)anilino)-1-(4-(2-acetylaminoethyl)phenyl)methylene]-6-fluoro-2-indolinone |
| 3.7 | 3-Z-[1-(4-(dimethylaminomethyl)anilino)-1-(4-methoxycarbonylmethylphenyl)methylene]-6-fluoro-2-indolinone |
| 3.8 | 3-Z-[1-(4-(dimethylaminomethyl)anilino)-1-(3-iodophenyl)methylene]-6-fluoro-2-indolinone |
| 3.9 | 3-Z-[1-(4-(dimethylaminomethyl)anilino)-1-(3-methoxycarbonylmethylphenyl)methylene]-6-fluoro-2-indolinone |
| 3.10 | 3-Z-[1-(4-(dimethylaminomethyl)anilino)-1-(3-(N-tert-butoxycarbonyl-aminomethyl)phenyl)methylene]-6-fluoro-2-indolinone |
| 3.11 | 3-Z-[1-(4-(N-(2-dimethylaminoethyl)-N-methylsulphonylamino)anilino)-1-(4-methoxycarbonylmethylphenyl)methylene]-6-fluoro-2-indolinone |
| 3.12 | 3-Z-[1-(4-(N-(4-methylpiperazin-1-ylmethylcarbonyl)-N-methylamino)anilino)-1-(4-methoxycarbonylmethylphenyl)methylene]-6-fluoro-2-indolinone |
| 3.13 | 3-Z-[1-(4-(dimethylaminomethyl)anilino)-1-(3-cyanomethylphenyl)-methylene]-6-fluoro-2-indolinone |
| 3.14 | 3-Z-[1-(4-(N-(4-methylpiperazin-1-ylmethylcarbonyl)-N-methylamino)anilino)-1-(4-(N-tert-butoxycarbonyl-aminomethyl)phenyl)methylene]-6-fluoro-2-indolinone |
| 3.15 | 3-Z-[1-(4-(dimethylaminomethyl)anilino)-1-(4-(N-tert-butoxycarbonyl-aminomethyl)phenyl)methylene]-6-fluoro-2-indolinone |
| 3.16 | 3-Z-[1-(4-(dimethylaminomethyl)anilino)-1-(3-(N-tert-butoxycarbonyl-2-aminoethyl)phenyl)methylene]-6-fluoro-2-indolinone |
| 3.17 | 3-Z-[1-(4-(N-Acetyl-N-methylamino)anilino)-1-(4-(2-methoxycarbonylethyl)phenyl)methylene]-6-fluoro-2-indolinone |
| 3.18 | 3-Z-[1-(4-(N-(4-methylpiperazin-1-ylmethylcarbonyl)-N-methylamino)anilino)-1-(4-(2-methoxycarbonylethyl)phenyl)methylene]-6-fluoro-2-indolinone |
| 3.19 | 3-Z-[1-(4-(N-(2-dimethylaminoethyl)-N-methylsulphonylamino)anilino)-1-(4-methoxycarbonylmethylphenyl)methylene]-6-fluoro-2-indolinone |
| 3.20 | 3-Z-[1-(4-(N-(3-dimethylaminopropyl)-N-acetylamino)anilino)-1-(4-(2-methoxycarbonylethyl)phenyl)methylene]-6-fluoro-2-indolinone |
| 3.21 | 3-Z-[1-(4-(N-tert-butoxycarbonylmethylaminomethyl)anilino)-1-(4-(2-methoxycarbonylethyl)phenyl)methylene]-6-fluoro-2-indolinone |

-continued

| Example | Name |
|---|---|
| 3.22 | 3-Z-[1-(4-(4-methylpiperazin-1-yl-carbonyl)anilino)-1-(4-(2-methoxycarbonylethyl)phenyl)methylene]-6-fluoro-2-indolinone |
| 3.23 | 3-Z-[1-(4-(1-methylimidazol-2-yl)anilino)-1-(4-(2-methoxycarbonylethyl)phenyl)methylene]-6-fluoro-2-indolinone |
| 3.24 | 3-Z-[1-(4-methylsulphonylanilino)-1-(4-(2-methoxycarbonylethyl)phenyl)methylene]-6-fluoro-2-indolinone |
| 3.25 | 3-Z-[1-(4-(N-(4-methylpiperazin-1-ylmethylcarbonyl)-N-methylamino)anilino)-1-(3-methoxycarbonylmethylphenyl)methylene]-6-fluoro-2-indolinone |
| 3.26 | 3-Z-[1-(4-(N-(2-dimethylaminoethyl)-N-methylsulphonylamino)anilino)-1-(3-methoxycarbonylmethylphenyl)methylene]-6-fluoro-2-indolinone |
| 3.27 | 3-Z-[1-(4-(4-methylpiperazin-1-yl-carbonyl)anilino)-1-(3-methoxycarbonylmethylphenyl)methylene]-6-fluoro-2-indolinone |
| 3.28 | 3-Z-[1-(4-(N-(dimethylaminomethylcarbonyl)-N-methylamino)anilino)-1-(3-methoxycarbonylmethylphenyl)methylene]-6-fluoro-2-indolinone |
| 3.29 | 3-Z-[1-(4-(N-(3-dimethylaminopropyl)-N-acetylamino)anilino)-1-(3-methoxycarbonylmethylphenyl)methylene]-6-fluoro-2-indolinone |
| 3.30 | 3-Z-[1-(4-(N-(2-dimethylaminoethyl)-N-acetylamino)anilino)-1-(3-methoxycarbonylmethylphenyl)methylene]-6-fluoro-2-indolinone |
| 3.31 | 3-Z-[1-(4-(N-(4-dimethylamino-butylcarbonyl)-N-methylamino)anilino)-1-(3-methoxycarbonylmethylphenyl)methylene]-6-fluoro-2-indolinone |
| 3.32 | 3-Z-[1-Anilino-1-(4-methoxycarbonylmethylphenyl)methylene]-6-fluoro-2-indolinone |
| 3.33 | 3-Z-[1-(4-(1-methylimidazol-2-yl)anilino)-1-(4-methoxycarbonylmethylphenyl)methylene]-6-fluoro-2-indolinone |
| 3.34 | 3-Z-[1-(4-(4-methylpiperazin-1-ylcarbonyl)anilino)-1-(4-methoxycarbonylmethylphenyl)methylene]-6-fluoro-2-indolinone |
| 3.35 | 3-Z-[1-(4-(N-(dimethylaminocarbonylmethyl)-N-methylsulphonylamino)anilino)-1-(4-methoxycarbonylmethylphenyl)-methylene]-6-fluoro-2-indolinone |
| 3.36 | 3-Z-[1-(4-(N-(dimethylaminomethylcarbonyl)-N-methylamino)anilino)-1-(4-methoxycarbonylmethylphenyl)methylene]-6-fluoro-2-indolinone |
| 3.37 | 3-Z-[1-(4-(N-methyl-N-acetylamino)anilino)-1-(4-methoxycarbonylmethylphenyl)methylene]-6-fluoro-2-indolinone |
| 3.38 | 3-Z-[1-(4-(N-(2-dimethylaminoethylcarbonyl)-N-methylamino)anilino)-1-(4-methoxycarbonylmethylphenyl)methylene]-6-fluoro-2-indolinone |
| 3.39 | 3-Z-[1-(4-methylsulphonylanilino)-1-(4-methoxycarbonylmethylphenyl)methylene]-6-fluoro-2-indolinone |
| 3.40 | 3-Z-[1-(4-(N-(3-dimethylaminopropylcarbonyl)-N-methylamino)anilino)-1-(4-methoxycarbonylmethylphenyl)methylene]-6-fluoro-2-indolinone |
| 3.41 | 3-Z-[1-(4-(N-(3-dimethylaminopropyl)-N-acetylamino)anilino)-1-(4-methoxycarbonylmethylphenyl)methylene]-6-fluoro-2-indolinone |
| 3.42 | 3-Z-[1-Anilino-1-(3-methoxycarbonylmethylphenyl)methylene]-6-fluoro-2-indolinone |
| 3.43 | 3-Z-[1-(4-methylsulphonylanilino)-1-(3-methoxycarbonylmethylphenyl)-methylene]-6-fluoro-2-indolinone |
| 3.44 | 3-Z-[1-(4-(1-methylimidazol-2-yl)anilino)-1-(3-methoxycarbonylmethylphenyl)methylene]-6-fluoro-2-indolinone |
| 3.45 | 3-Z-[1-(4-(N-(dimethylaminocarbonylmethyl)-N-methylsulphonylamino)anilino)-1-(3-methoxycarbonylmethylphenyl)-methylene]-6-fluoro-2-indolinone |
| 3.46 | 3-Z-[1-(4-(N-(3-dimethylaminopropylcarbonyl)-N-methylamino)anilino)-1-(3-methoxycarbonylmethylphenyl)methylene]-6-fluoro-2-indolinone |
| 3.47 | 3-Z-[1-(4-(N-(2-dimethylaminoethylcarbonyl)-N-methylamino)anilino)-1-(3-methoxycarbonylmethylphenyl)methylene]-6-fluoro-2-indolinone |
| 3.48 | 3-Z-[1-(4-(N-(4-methylpiperazin-1-ylmethylcarbonyl)-N-methylamino)anilino)-1-(3-(2-methoxycarbonylethyl)phenyl)methylene]-6-fluoro-2-indolinone |
| 3.49 | 3-Z-[1-(4-(N-(2-dimethylaminoethyl)-N-methylsulphonylamino)anilino)-1-(3-(2-methoxycarbonylethyl)phenyl)methylene]-6-fluoro-2-indolinone |
| 3.50 | 3-Z-[1-(4-(N-(dimethylaminomethylcarbonyl)-N-methylamino)anilino)-1-(3-(2-methoxycarbonylethyl)phenyl)methylene]-6-fluoro-2-indolinone |
| 3.51 | 3-Z-[1-(4-(N-(3-dimethylaminopropyl)-N-acetylamino)anilino)-1-(3-(2-methoxycarbonylethyl)phenyl)methylene]-6-fluoro-2-indolinone |
| 3.52 | 3-Z-[1-(4-(N-(4-methylpiperazin-1-ylmethylcarbonyl)-N-methylamino)anilino)-1-(3-(N-tert-butoxycarbonyl-aminomethyl)phenyl)methylene]-6-fluoro-2-indolinone |
| 3.53 | 3-Z-[1-(4-(N-methyl-N-acetylamino)anilino)-1-(3-acetylaminomethylphenyl)methylene]-6-chloro-2-indolinone |
| 3.54 | 3-Z-[1-(4-(N-(3-dimethylaminopropyl)-N-acetylamino)anilino)-1-(3-acetylaminomethylphenyl)methylene]-6-chloro-2-indolinone |
| 3.55 | 3-Z-[1-(4-(N-(2-dimethylaminoethyl)-N-methylsulphonylamino)anilino)-1-(3-acetylaminomethylphenyl)methylene]-6-chloro-2-indolinone |
| 3.56 | 3-Z-[1-(4-(N-(dimethylaminomethylcarbonyl)-N-methylamino)anilino)-1-(3-acetylaminomethylphenyl)methylene]-6-chloro-2-indolinone |
| 3.57 | 3-Z-[1-(4-(2-dimethylaminoethyl)anilino)-1-(4-(2-methoxycarbonylethyl)phenyl)methylene]-6-fluoro-2-indolinone |

-continued

| Example | Name |
|---|---|
| 3.58 | 3-Z-[1-(4-(N-(2-dimethylaminoethylcarbonyl)-N-methylamino)anilino)-1-(4-(2-methoxycarbonylethyl)phenyl)methylene]-6-fluoro-2-indolinone |
| 3.59 | 3-Z-[1-(4-(N-(dimethylaminomethylcarbonyl)-N-methylamino)anilino)-1-(4-(2-methoxycarbonylethyl)phenyl)methylene]-6-fluoro-2-indolinone |
| 3.60 | 3-Z-[1-(4-(2-dimethylaminoethyl)anilino)-1-(3-(2-ethoxycarbonylethyl)phenyl)methylene]-6-fluoro-2-indolinone |
| 3.61 | 3-Z-[1-(4-(N-(2-dimethylaminoethyl)-N-acetylamino)anilino)-1-(4-(2-methoxycarbonylethyl)phenyl)methylene]-6-fluoro-2-indolinone |
| 3.62 | 3-Z-[1-(4-(N-(3-dimethylaminopropylcarbonyl)-N-methylamino)anilino)-1-(3-(2-ethoxycarbonylethyl)phenyl)methylene]-6-fluoro-2-indolinone |
| 3.63 | 3-Z-[1-(4-(N-(4-dimethylaminobutylcarbonyl)-N-methylamino)anilino)-1-(3-(2-ethoxycarbonylethyl)phenyl)methylene]-6-fluoro-2-indolinone |
| 3.64 | 3-Z-[1-(4-(1-methylimidazol-2-yl)anilino)-1-(3-(2-ethoxycarbonylethyl)phenyl)methylene]-6-fluoro-2-indolinone |
| 3.65 | 3-Z-[1-(4-(N-(4-dimethylaminobutylcarbonyl)-N-methylamino)anilino)-1-(4-(2-methoxycarbonylethyl)phenyl)methylene]-6-fluoro-2-indolinone |
| 3.66 | 3-Z-[1anilino-1-(4-(2-methoxycarbonylethyl)phenyl)methylene]-6-fluoro-2-indolinone |
| 3.67 | 3-Z-[1-(4-(pyrrolidin-1-ylmethyl)anilino)-1-(4-(2-methoxycarbonylethyl)phenyl)methylene]-6-fluoro-2-indolinone |
| 3.68 | 3-Z-[1-(4-(diethylaminomethyl)anilino)-1-(4-(2-methoxycarbonylethyl)phenyl)methylene]-6-fluoro-2-indolinone |
| 3.69 | 3-Z-[1-(4-(N-tert-butoxycarbonylaminomethyl)anilino)-1-(4-(2-methoxycarbonylethyl)phenyl)methylene]-6-fluoro-2-indolinone |
| 3.70 | 3-Z-[1-(4-(2-dimethylaminoethyl)anilino)-1-(3-methoxycarbonylmethylphenyl)methylene]-6-fluoro-2-indolinone |
| 3.71 | 3-Z-[1-(4-(2-dimethylaminoethyl)anilino)-1-(4-methoxycarbonylmethylphenyl)methylene]-6-fluoro-2-indolinone |
| 3.72 | 3-Z-[1-(4-(dimethylaminomethyl)anilino)-1-(3-(2-ethoxycarbonylethyl)phenyl)methylene]-6-fluoro-2-indolinone |
| 3.73 | 3-Z-[1-(4-(2-dimethylaminoethyl)anilino)-1-(4-(2-methoxycarbonylethyl)phenyl)methylene]-6-chloro-2-indolinone |
| 3.74 | 3-Z-[1-(4-(1-methylimidazol-2-yl)anilino)-1-(4-(2-ethoxycarbonylethyl)phenyl)methylene]-6-chloro-2-indolinone |
| 3.75 | 3-Z-[1-(4-dimethylaminomethylanilino)-1-(4-(2-methoxycarbonylethyl)phenyl)methylene]-6-chloro-2-indolinone |
| 3.76 | 3-Z-[1-(4-dimethylaminomethylanilino)-1-(4-(2-ethoxycarbonylethyl)phenyl)methylene]-6-fluoro-2-indolinone |
| 3.77 | 3-Z-[1-(4-((4-methylpiperazin-1-yl)methyl)anilino)-1-(3-(2-methoxycarbonylethyl)phenyl)methylene]-6-fluoro-2-indolinone |
| 3.78 | 3-Z-[1-(4-(imidazol-1-ylmethyl)anilino)-1-(3-(2-methoxycarbonylethyl)phenyl)methylene]-6-fluoro-2-indolinone |
| 3.79 | 3-Z-[1-(4-((4-methylpiperazin-1-yl)methyl)anilino)-1-(4-(2-methoxycarbonylethyl)phenyl)methylene]-6-fluoro-2-indolinone |
| 3.80 | 3-Z-[1-(4-(imidazol-1-ylmethyl)anilino)-1-(4-(2-methoxycarbonylethyl)phenyl)methylene]-6-fluoro-2-indolinone |
| 3.81 | 3-Z-[1-(4-(N-(2-dimethylaminoethyl)-N-methylaminomethyl)anilino)-1-(4-(2-methoxycarbonylethyl)phenyl)methylene]-6-fluoro-2-indolinone |
| 3.82 | 3-Z-[1-(4-(N-(2-dimethylaminoethyl)-N-methylaminomethyl)anilino)-1-(3-(2-ethoxycarbonylethyl)phenyl)methylene]-6-fluoro-2-indolinone |
| 3.83 | 3-Z-[1-(4-(pyrrolidin-1-ylmethyl)anilino)-1-(4-(2-methoxycarbonylethyl)phenyl)methylene]-6-chloro-2-indolinone |
| 3.84 | 3-Z-[1anilino-1-(3-(2-ethoxycarbonylethyl)phenyl)methylene]-6-fluoro-2-indolinone |
| 3.85 | 3-Z-[1-(4-(N-tert-butoxycarbonylaminomethyl)anilino)-1-(3-(2-ethoxycarbonylethyl)phenyl)methylene]-6-fluoro-2-indolinone |
| 3.86 | 3-Z-[1-(4-(N-tert-butoxycarbonylmethylaminomethyl)anilino)-1-(3-(2-ethoxycarbonylethyl)phenyl)methylene]-6-fluoro-2-indolinone |
| 3.87 | 3-Z-[1-(4-dimethylaminomethylanilino)-1-(3-methoxycarbonylmethoxy-phenyl)methylene]-6-fluoro-2-indolinone |
| 3.88 | 3-Z-[1-(4-dimethylaminomethylanilino)-1-(4-methoxycarbonylmethoxy-phenyl)methylene]-6-fluoro-2-indolinone |
| 3.89 | 3-Z-[1-(4-dimethylaminomethylanilino)-1-(3-(2-ethoxycarbonyl-ethoxy)phenyl)methylene]-6-fluoro-2-indolinone |
| 3.90 | 3-Z-[1-(4-(pyrrolidin-1-ylmethyl)anilino)-1-(4-(2-methoxycarbonylethyl)phenyl)methylene]-6-bromo-2-indolinone |
| 3.91 | 3-Z-[1-(4-(dimethylaminomethyl)anilino)-1-(4-(2-methoxycarbonylethyl)phenyl)methylene]-6-bromo-2-indolinone |
| 3.92 | 3-Z-[1-(4-(diethylaminomethyl)anilino)-1-(4-(2-methoxycarbonylethyl)phenyl)methylene]-6-bromo-2-indolinone |
| 3.93 | 3-Z-[1-(3-dimethylaminomethylanilino)-1-(4-(2-methoxycarbonylethyl)phenyl)methylene]-6-fluoro-2-indolinone |
| 3.94 | 3-Z-[1-(3-dimethylaminomethylanilino)-1-(3-(2-ethoxycarbonylethyl)phenyl)methylene]-6-fluoro-2-indolinone |
| 3.95 | 3-Z-[1-(3-dimethylaminomethylanilino)-1-(4-(2-methoxycarbonylethyl)phenyl)methylene]-6-chloro-2-indolinone |

-continued

| Example | Name |
|---|---|
| 4.0 | 3-Z-[1-(4-(dimethylaminomethyl)anilino)-1-(3,4-dimethoxyphenyl)-methylene]-6-cyano-2-indolinone |
| 5.0 | 3-Z-[1-(4-(N-methyl-N-methylsulphonylamino)anilino)-1-(3-(2-methoxycarbonylvinyl)phenyl)methylene]-6-chloro-2-indolinone |
| 5.1 | 3-Z-[1-(4-(dimethylaminomethyl)anilino)-1-(4-(2-methoxycarbonyl-vinyl)phenyl)methylene]-6-chloro-2-indolinone |
| 5.2 | 3-Z-[1-(4-(dimethylaminomethyl)anilino)-1-(4-(2-carbamoyl-vinyl)phenyl)methylene]-6-fluoro-2-indolinone |
| 5.3 | 3-Z-[1-(4-(dimethylaminomethyl)anilino)-1-(4-(2-methoxycarbonyl-vinyl)phenyl)methylene]-6-fluoro-2-indolinone |
| 5.4 | 3-Z-[1-(4-(dimethylaminomethyl)anilino)-1-(3-(2-methoxycarbonyl-vinyl)phenyl)methylene]-6-fluoro-2-indolinone |
| 6.0 | 3-Z-[1-(4-dimethylaminomethylanilino)-1-(3-(2-methoxycarbonylethyl)phenyl)methylene]-6-chloro-2-indolinone |
| 6.1 | 3-Z-[1-(4-(N-methyl-N-methylsulphonylamino)anilino)-1-(3-(2-methoxycarbonylethyl)phenyl)methylene]-6-chloro-2-indolinone |
| 6.2 | 3-Z-[1-(4-dimethylaminomethylanilino)-1-(4-(2-carbamoyl-ethyl)phenyl)methylene]-6-fluoro-2-indolinone |
| 6.3 | 3-Z-[1-(4-dimethylaminomethylanilino)-1-(4-(2-methoxycarbonylethyl)phenyl)methylene]-6-fluoro-2-indolinone |
| 6.4 | 3-Z-[1-(4-dimethylaminomethylanilino)-1-(3-(2-methoxycarbonylethyl)phenyl)methylene]-6-fluoro-2-indolinone |
| 7.0 | 3-Z-[1-(4-dimethylaminomethylanilino)-1-(4-aminomethylphenyl)-methylene]-6-chloro-2-indolinone |
| 8.0 | 3-Z-[1-(4-(N-((4-methylpiperazin-1-yl)methylcarbonyl)-N-methylamino)anilino)-1-(4-aminomethylphenyl)methylene]-6-chloro-2-indolinone |
| 9.0 | 3-Z-[1-(4-(dimethylaminomethyl)anilino)-1-(3-aminomethylphenyl)-methylene]-6-fluoro-2-indolinone |
| 9.1 | 3-Z-[1-(4-(dimethylaminomethyl)anilino)-1-(3-(2-aminoethyl)phenyl)methylene]-6-fluoro-2-indolinone |
| 9.2 | 3-Z-[1-(4-(dimethylaminomethyl)anilino)-1-(4-aminomethylphenyl)-methylene]-6-fluoro-2-indolinone |
| 9.3 | 3-Z-[1-(4-(N-(4-methylpiperazin-1-ylmethylcarbonyl)-N-methylamino)anilino)-1-(4-aminomethylphenyl)methylene]-6-fluoro-2-indolinone |
| 9.4 | 3-Z-[1-(4-(methylaminomethyl)anilino)-1-(4-(2-carboxyethyl)phenyl)methylene]-6-fluoro-2-indolinone |
| 9.5 | 3-Z-[1-(4-(methylaminomethyl)anilino)-1-(4-(2-methylcarbamoyl-ethyl)phenyl)methylene]-6-fluoro-2-indolinone |
| 9.6 | 3-Z-[1-(4-(N-(4-methylpiperazin-1-ylmethylcarbonyl)-N-methylamino)anilino)-1-(3-aminomethylphenyl)methylene]-6-fluoro-2-indolinone |
| 9.7 | 3-Z-[1-(4-(aminomethyl)anilino)-1-(4-(2-methoxycarbonylethyl)phenyl)methylene]-6-fluoro-2-indolinone |
| 9.8 | 3-Z-[1-(4-(aminomethyl)anilino)-1-(3-(2-ethoxycarbonylethyl)phenyl)methylene]-6-fluoro-2-indolinone |
| 9.9 | 3-Z-[1-(4-(methylaminomethyl)anilino)-1-(3-(2-ethoxycarbonylethyl)phenyl)methylene]-6-fluoro-2-indolinone |
| 10.0 | 3-Z-[1-(4-dimethylaminomethylanilino)-1-(3-(2-carboxyethyl)phenyl)methylene]-6-chloro-2-indolinone |
| 10.1 | 3-Z-[1-(4-dimethylaminomethylanilino)-1-(4-(2-carboxyethyl)phenyl)methylene]-6-fluoro-2-indolinone |
| 10.2 | 3-Z-[1-(4-dimethylaminomethylanilino)-1-(3-carboxymethylphenyl)-methylene]-6-fluoro-2-indolinone |
| 10.3 | 3-Z-[1-(4-dimethylaminomethylanilino)-1-(3-(2-carboxyethyl)phenyl)methylene]-6-fluoro-2-indolinone |
| 10.4 | 3-Z-[1-(4-dimethylaminomethylanilino)-1-(4-carboxymethylphenyl)-methylene]-6-fluoro-2-indolinone |
| 10.5 | 3-Z-[1-(4-(N-(4-methylpiperazin-1-ylmethylcarbonyl)-N-methylamino)anilino)-1-(4-carboxymethylphenyl)methylene]-6-fluoro-2-indolinone |
| 10.6 | 3-Z-[1-(4-(N-(2-dimethylaminoethyl)-N-methylsulphonylamino)anilino)-1-(4-carboxymethylphenyl)methylene]-6-fluoro-2-indolinone |
| 10.7 | 3-Z-[1-(4-(N-methyl-N-acetylamino)anilino)-1-(4-(2-carboxyethyl)phenyl)methylene]-6-fluoro-2-indolinone |
| 10.8 | 3-Z-[1-(4-(N-(4-methylpiperazin-1-ylmethylcarbonyl)-N-methylamino)anilino)-1-(4-(2-carboxyethyl)phenyl)methylene]-6-fluoro-2-indolinone |
| 10.9 | 3-Z-[1-(4-(N-(2-dimethylaminoethyl)-N-methylsulphonylamino)anilino)-1-(4-(2-carboxyethyl)phenyl)methylene]-6-fluoro-2-indolinone |
| 10.10 | 3-Z-[1-(4-(N-(3-dimethylaminopropyl)-N-acetylamino)anilino)-1-(4-(2-carboxyethyl)phenyl)methylene]-6-fluoro-2-indolinone |
| 10.11 | 3-Z-[1-(4-(N-tert-butoxycarbonylmethylaminomethyl)anilino)-1-(4-(2-carboxyethyl)phenyl)methylene]-6-fluoro-2-indolinone |
| 10.12 | 3-Z-[1-(4-(4-methylpiperazin-1-ylcarbonyl)anilino)-1-(4-(2-carboxyethyl)phenyl)methylene]-6-fluoro-2-indolinone |

-continued

| Example | Name |
|---|---|
| 10.13 | 3-Z-[1-(4-(1-methylimidazol-2-yl)anilino)-1-(4-(2-carboxyethyl)phenyl)methylene]-6-fluoro-2-indolinone |
| 10.14 | 3-Z-[1-(4-methylsulphonylanilino)-1-(4-(2-carboxyethyl)phenyl)methylene]-6-fluoro-2-indolinone |
| 10.15 | 3-Z-[1-(4-(4-methylpiperazin-1-ylcarbonyl)anilino)-1-(3-carboxymethylphenyl)methylene]-6-fluoro-2-indolinone |
| 10.16 | 3-Z-[1-(4-(N-(4-methylpiperazin-1-ylmethylcarbonyl)-N-methylamino)anilino)-1-(3-carboxymethylphenyl)methylene]-6-fluoro-2-indolinone |
| 10.17 | 3-Z-[1-(4-(N-(dimethylaminomethylcarbonyl)-N-methylamino)anilino)-1-(3-carboxymethylphenyl)methylene]-6-fluoro-2-indolinone |
| 10.18 | 3-Z-[1-(4-(N-(4-dimethylaminobutylcarbonyl)-N-methylamino)anilino)-1-(3-carboxymethylphenyl)methylene]-6-fluoro-2-indolinone |
| 10.19 | 3-Z-[1-Anilino-1-(3-carboxymethylphenyl)-methylene]-6-fluoro-2-indolinone |
| 10.20 | 3-Z-[1-(4-methylsulphonylanilino)-1-(3-carboxymethylphenyl)-methylene]-6-fluoro-2-indolinone |
| 10.21 | 3-Z-[1-(4-(1-methylimidazol-2-yl)anilino)-1-(3-carboxymethylphenyl)-methylene]-6-fluoro-2-indolinone |
| 10.22 | 3-Z-[1-(4-(N-(dimethylaminocarbonylmethyl)-N-methylsulphonylamino)anilino)-1-(3-carboxymethylphenyl)-methylene]-6-fluoro-2-indolinone |
| 10.23 | 3-Z-[1anilino-1-(4-carboxymethylphenyl)methylene]-6-fluoro-2-indolinone |
| 10.24 | 3-Z-[1-(4-(1-methylimidazol-2-yl)anilino)-1-(4-carboxymethylphenyl)-methylene]-6-fluoro-2-indolinone |
| 10.25 | 3-Z-[1-(4-(N-(3-dimethylaminopropylcarbonyl)-N-methylamino)anilino)-1-(4-carboxymethylphenyl)methylene]-6-fluoro-2-indolinone |
| 10.26 | 3-Z-[1-(4-(N-(dimethylaminomethylcarbonyl)-N-methylamino)anilino)-1-(4-carboxymethylphenyl)methylene]-6-fluoro-2-indolinone |
| 10.27 | 3-Z-[1-(4-(4-methylpiperazin-1-yl-carbonyl)anilino)-1-(4-carboxymethylphenyl)methylene]-6-fluoro-2-indolinone |
| 10.28 | 3-Z-[1-(4-methylsulphonylanilino)-1-(4-carboxymethylphenyl)-methylene]-6-fluoro-2-indolinone |
| 10.29 | 3-Z-[1-(4-(N-methyl-N-acetylamino)anilino)-1-(4-carboxymethylphenyl)-methylene]-6-fluoro-2-indolinone |
| 10.30 | 3-Z-[1-(4-(N-(dimethylaminocarbonylmethyl)-N-methylsulphonylamino)anilino)-1-(4-carboxymethylphenyl)methylene]-6-fluoro-2-indolinone |
| 10.31 | 3-Z-[1-(4-(N-(2-dimethylaminoethylcarbonyl)-N-methylamino)anilino)-1-(4-carboxymethylphenyl)methylene]-6-fluoro-2-indolinone |
| 10.32 | 3-Z-[1-(4-(N-(3-dimethylaminopropylcarbonyl)-N-methylamino)anilino)-1-(4-carboxymethylphenyl)methylene]-6-fluoro-2-indolinone |
| 10.33 | 3-Z-[1-(4-(N-(4-methylpiperazin-1-ylmethylcarbonyl)-N-methylamino)anilino)-1-(3-(2-carboxyethyl)phenyl)methylene]-6-fluoro-2-indolinone |
| 10.34 | 3-Z-[1-(4-(N-(2-dimethylaminoethyl)-N-methylsulphonylamino)anilino)-1-(3-carboxymethylphenyl)methylene]-6-fluoro-2-indolinone |
| 10.35 | 3-Z-[1-(4-(N-(2-dimethylaminoethyl)-N-methylsulphonylamino)anilino)-1-(3-(2-carboxyethyl)phenyl)methylene]-6-fluoro-2-indolinone |
| 10.36 | 3-Z-[1-(4-(N-(dimethylaminomethylcarbonyl)-N-methylamino)anilino)-1-(3-(2-carboxyethyl)phenyl)methylene]-6-fluoro-2-indolinone |
| 10.37 | 3-Z-[1-(4-(N-(3-dimethylaminopropyl)-N-acetylamino)anilino)-1-(3-(2-carboxyethyl)phenyl)methylene]-6-fluoro-2-indolinone |
| 10.38 | 3-Z-[1-(4-(N-(dimethylaminomethylcarbonyl)-N-methylamino)anilino)-1-(4-(2-carboxyethyl)phenyl)methylene]-6-fluoro-2-indolinone |
| 10.39 | 3-Z-[1-(4-(2-dimethylaminoethyl)anilino)-1-(4-(2-carboxyethyl)phenyl)methylene]-6-fluoro-2-indolinone |
| 10.40 | 3-Z-[1-(4-(N-(2-dimethylaminoethylcarbonyl)-N-methylamino)anilino)-1-(4-(2-carboxyethyl)phenyl)methylene]-6-fluoro-2-indolinone |
| 10.41 | 3-Z-[1-(4-(2-dimethylaminoethyl)anilino)-1-(3-(2-carboxyethyl)phenyl)methylene]-6-fluoro-2-indolinone |
| 10.42 | 3-Z-[1-(4-(N-(2-dimethylaminoethyl)-N-acetylamino)anilino)-1-(4-(2-carboxyethyl)phenyl)methylene]-6-fluoro-2-indolinone |
| 10.43 | 3-Z-[1-(4-(N-(3-dimethylaminopropylcarbonyl)-N-methylamino)anilino)-1-(3-(2-carboxyethyl)phenyl)methylene]-6-fluoro-2-indolinone |
| 10.44 | 3-Z-[1-(4-(N-(4-dimethylamino-butylcarbonyl)-N-methylamino)anilino)-1-(3-(2-carboxyethyl)phenyl)methylene]-6-fluoro-2-indolinone |
| 10.45 | 3-Z-[1-(4-(1-methylimidazol-2-yl)anilino)-1-(3-(2-carboxyethyl)phenyl)methylene]-6-fluoro-2-indolinone |
| 10.46 | 3-Z-[1-(4-(N-(4-dimethylaminobutylcarbonyl)-N-methylamino)anilino)-1-(4-(2-carboxyethyl)phenyl)methylene]-6-fluoro-2-indolinone |
| 10.47 | 3-Z-[1anilino-1-(4-(2-carboxyethyl)phenyl)methylene]-6-fluoro-2-indolinone |
| 10.48 | 3-Z-[1-(4-(pyrrolidin-1-ylmethyl)anilino)-1-(4-(2-carboxyethyl)phenyl)methylene]-6-fluoro-2-indolinone |

-continued

| Example | Name |
|---|---|
| 10.49 | 3-Z-[1-(4-(diethylaminomethyl)anilino)-1-(4-(2-carboxyethyl)phenyl)methylene]-6-fluoro-2-indolinone |
| 10.50 | 3-Z[1-(4-aminomethylanilino)-1-(4-(2-carboxyethyl)phenyl)methylene]-6-fluoro-2-indolinone |
| 10.51 | 3-Z-[1-(4-(2-dimethylaminoethyl)anilino)-1-(3-carboxymethylphenyl)methylene]-6-fluoro-2-indolinone |
| 10.52 | 3-Z-[1-(4-(2-dimethylaminoethyl)anilino)-1-(4-carboxymethylphenyl)methylene]-6-fluoro-2-indolinone |
| 10.53 | 3-Z-[1-(4-(2-dimethylaminoethyl)anilino)-1-(4-(2-carboxyethyl)phenyl)methylene]-6-chloro-2-indolinone |
| 10.54 | 3-Z-[1-(4-(1-methylimidazol-2-yl)anilino)-1-(4-(2-carboxyethyl)phenyl)methylene]-6-chloro-2-indolinone |
| 10.55 | 3-Z-[1-(4-dimethylaminomethylanilino)-1-(4-(2-carboxyethyl)phenyl)methylene]-6-chloro-2-indolinone |
| 10.56 | 3-Z-[1-(4-((4-methylpiperazin-1-yl)methyl)anilino)-1-(3-(2-carboxyethyl)phenyl)methylene]-6-fluoro-2-indolinone |
| 10.57 | 3-Z-[1-(4-(imidazol-1-ylmethyl)anilino)-1-(3-(2-carboxyethyl)phenyl)methylene]-6-fluoro-2-indolinone |
| 10.58 | 3-Z-[1-(4-(N-(2-dimethylaminoethyl)-N-methylaminomethyl)anilino)-1-(3-(2-carboxyethyl)phenyl)methylene]-6-fluoro-2-indolinone |
| 10.59 | 3-Z-[1-(4-((4-methylpiperazin-1-yl)methyl)anilino)-1-(4-(2-carboxyethyl)phenyl)methylene]-6-fluoro-2-indolinone |
| 10.60 | 3-Z-[1-(4-(imidazol-1-ylmethyl)anilino)-1-(4-(2-carboxyethyl)phenyl)methylene]-6-fluoro-2-indolinone |
| 10.61 | 3-Z-[1-(4-(pyrrolidin-1-ylmethyl)anilino)-1-(4-(2-carboxyethyl)phenyl)methylene]-6-chloro-2-indolinone |
| 10.62 | 3-Z-[1-(4-(N-(2-dimethylaminoethyl)-N-methylaminomethyl)anilino)-1-(4-(2-carboxyethyl)phenyl)methylene]-6-fluoro-2-indolinone |
| 10.63 | 3-Z-[1anilino-1-(3-(2-carboxyethyl)phenyl)methylene]-6-fluoro-2-indolinone |
| 10.64 | 3-Z-[1-(4-aminomethylanilino)-1-(3-(2-carboxyethyl)phenyl)methylene]-6-fluoro-2-indolinone |
| 10.65 | 3-Z-[1-(4-methylaminomethylanilino)-1-(3-(2-carboxyethyl)phenyl)methylene]-6-fluoro-2-indolinone |
| 10.66 | 3-Z-[1-(4-dimethylaminomethylanilino)-1-(3-carboxymethoxy-phenyl)-methylene]-6-fluoro-2-indolinone |
| 10.67 | 3-Z-[1-(4-dimethylaminomethylanilino)-1-(4-carboxymethoxy-phenyl)phenyl)methylene]-6-fluoro-2-indolinone |
| 10.68 | 3-Z-[1-(4-(pyrrolidin-1-ylmethyl)anilino)-1-(4-(2-carboxyethyl)phenyl)methylene]-6-bromo-2-indolinone |
| 10.69 | 3-Z-[1-(4-(dimethylaminomethyl)anilino)-1-(4-(2-carboxyethyl)phenyl)methylene]-6-bromo-2-indolinone |
| 10.70 | 3-Z-[1-(4-(diethylaminomethyl)anilino)-1-(4-(2-carboxyethyl)-methylene]-6-bromo-2-indolinone |
| 10.71 | 3-Z-[1-(3-dimethylaminomethylanilino)-1-(4-(2-carboxyethyl)phenyl)methylene]-6-fluoro-2-indolinone |
| 10.72 | 3-Z-[1-(3-dimethylaminomethylanilino)-1-(3-(2-carboxyethyl)phenyl)methylene]-6-fluoro-2-indolinone |
| 10.73 | 3-Z-[1-(3-dimethylaminomethylanilino)-1-(4-(2-carboxyethyl)phenyl)methylene]-6-chloro-2-indolinone |
| 11.0 | 3-Z-[1-(4-dimethylaminomethylanilino)-1-(3-(2-carbamoyl-ethyl)phenyl)methylene]-6-chloro-2-indolinone |
| 11.1 | 3-Z-[1-(4-dimethylaminomethylanilino)-1-(3-(2-methylcarbamoyl-ethyl)phenyl)methylene]-6-chloro-2-indolinone |
| 11.2 | 3-Z-[1-(4-dimethylaminomethylanilino)-1-(4-(2-methylcarbamoyl-ethyl)phenyl)methylene]-6-fluoro-2-indolinone |
| 11.3 | 3-Z-[1-(4-dimethylaminomethylanilino)-1-(3-dimethylcarbamoylmethylphenyl)methylene]-6-fluoro-2-indolinone |
| 11.4 | 3-Z-[1-(4-dimethylaminomethylanilino)-1-(3-(2-carbamoyl-ethyl)phenyl)methylene]-6-fluoro-2-indolinone |
| 11.5 | 3-Z-[1-(4-dimethylaminomethylanilino)-1-(3-(2-methylcarbamoyl-ethyl)phenyl)methylene]-6-fluoro-2-indolinone |
| 11.6 | 3-Z-[1-(4-dimethylaminomethylanilino)-1-(3-(2-dimethylcarbamoyl-ethyl)phenyl)methylene]-6-fluoro-2-indolinone |
| 11.7 | 3-Z-[1-(4-dimethylaminomethylanilino)-1-(3-carbamoylmethylphenyl)-methylene]-6-fluoro-2-indolinone |
| 11.8 | 3-Z-[1-(4-dimethylaminomethylanilino)-1-(3-methylcarbamoylmethylphenyl)methylene]-6-fluoro-2-indolinone |
| 11.9 | 3-Z-[1-(4-dimethylaminomethylanilino)-1-(4-carbamoylmethylphenyl)-methylene]-6-fluoro-2-indolinone |
| 11.10 | 3-Z-[1-(4-dimethylaminomethylanilino)-1-(4-(2-dimethylcarbamoyl-ethyl)phenyl)methylene]-6-fluoro-2-indolinone |
| 11.11 | 3-Z-[1-(4-dimethylaminomethylanilino)-1-(4-(2-(4-methylpiperazin-1-yl-carbonyl)ethyl)phenyl)methylene]-6-fluoro-2-indolinone |
| 11.12 | 3-Z-[1-(4-(N-(4-methylpiperazin-1-ylmethylcarbonyl)-N-methylamino)anilino)-1-(4-carbamoylmethylphenyl)methylene]-6-fluoro-2-indolinone |

-continued

| Example | Name |
|---|---|
| 11.13 | 3-Z-[1-(4-(N-(2-dimethylaminoethyl)-N-methylsulphonylamino)anilino)-1-(4-carbamoylmethylphenyl)methylene]-6-fluoro-2-indolinone |
| 11.14 | 3-Z-[1-(4-dimethylaminomethylanilino)-1-(4-dimethylcarbamoylmethylphenyl)methylene]-6-fluoro-2-indolinone |
| 11.15 | 3-Z-[1-(4-dimethylaminomethylanilino)-1-(4-methylcarbamoylmethylphenyl)methylene]-6-fluoro-2-indolinone |
| 11.16 | 3-Z-[1-(4-(N-(2-dimethylaminoethyl)-N-methylsulphonylamino)anilino)-1-(4-methylcarbamoylmethylphenyl)methylene]-6-fluoro-2-indolinone |
| 11.17 | 3-Z-[1-(4-(N-(2-dimethylaminoethyl)-N-methylsulphonylamino)anilino)-1-(4-dimethylcarbamoylmethylphenyl)methylene]-6-fluoro-2-indolinone |
| 11.18 | 3-Z-[1-(4-(N-(4-methylpiperazin-1-ylmethylcarbonyl)-N-methylamino)anilino)-1-(4-methylcarbamoylmethylphenyl)methylene]-6-fluoro-2-indolinone |
| 11.19 | 3-Z-[1-(4-(N-methyl-N-acetylamino)anilino)-1-(4-(2-methylcarbamoyl-ethyl)phenyl)methylene]-6-fluoro-2-indolinone |
| 11.20 | 3-Z-[1-(4-(N-(4-methylpiperazin-1-ylmethylcarbonyl)-N-methylamino)anilino)-1-(4-(2-methylcarbamoyl-ethyl)phenyl)methylene]-6-fluoro-2-indolinone |
| 11.21 | 3-Z-[1-(4-(N-(2-dimethylaminoethyl)-N-methylsulphonylamino)anilino)-1-(4-(2-methylcarbamoylethyl)phenyl)methylene]-6-fluoro-2-indolinone |
| 11.22 | 3-Z-[1-(4-(N-tert-butoxycarbonylmethylaminomethyl)anilino)-1-(4-(2-methylcarbamoylethyl)phenyl)methylene]-6-fluoro-2-indolinone |
| 11.23 | 3-Z-[1-(4-(1-methylimidazol-2-yl)anilino)-1-(4-(2-methylcarbamoyl-ethyl)phenyl)methylene]-6-fluoro-2-indolinone |
| 11.24 | 3-Z-[1-(4-methylsulphonylanilino)-1-(4-(2-methylcarbamoyl-ethyl)phenyl)methylene]-6-fluoro-2-indolinone |
| 11.25 | 3-Z-[1-(4-(4-methylpiperazin-1-ylcarbonyl)anilino)-1-(4-(2-methylcarbamoylethyl)phenyl)methylene]-6-fluoro-2-indolinone |
| 11.26 | 3-Z-[1-(4-(4-methylpiperazin-1-ylcarbonyl)anilino)-1-(3-methylcarbamoylmethylphenyl)methylene]-6-fluoro-2-indolinone |
| 11.27 | 3-Z-[1-(4-(N-(4-methylpiperazin-1-ylmethylcarbonyl)-N-methylamino)anilino)-1-(3-methylcarbamoylmethylphenyl)methylene]-6-fluoro-2-indolinone |
| 12.0 | 3-Z-[1-(4-dimethylaminomethylanilino)-1-(4-acetylaminomethylphenyl)-methylene]-6-chloro-2-indolinone |
| 12.1 | 3-Z-[1-(4-(N-(4-methylpiperazin-1-ylmethylcarbonyl)-N-methylamino)anilino)-1-(4-acetylaminomethylphenyl)methylene)-6-chloro-2-indolinone |
| 12.2 | 3-Z-[1-(4-dimethylaminomethylanilino)-1-(4-benzoylaminophenyl)-methylene]-6-chloro-2-indolinone |
| 12.3 | 3-Z-[1-(4-(N-(4-methylpiperazin-1-ylmethylcarbonyl)-N-methylamino)anilino)-1-(4-benzoylaminomethylphenyl)methylene]-6-chloro-2-indolinone |
| 12.4 | 3-Z-[1-(4-dimethylaminomethylanilino)-1-(3-acetylaminomethylphenyl)-methylene]-6-fluoro-2-indolinone |
| 12.5 | 3-Z-[1-(4-dimethylaminomethylanilino)-1-(3-propionylaminomethylphenyl)methylene]-6-fluoro-2-indolinone |
| 12.6 | 3-Z-[1-(4-dimethylaminomethylanilino)-1-(3-benzoylaminomethylphenyl)methylene]-6-fluoro-2-indolinone |
| 12.7 | 3-Z-[1-(4-dimethylaminomethylanilino)-1-(3-phenylacetylaminomethylphenyl)methylene]-6-fluoro-2-indolinone |
| 12.8 | 3-Z-[1-(4-dimethylaminomethylanilino)-1-(3-(2-acetylaminoethyl)phenyl)methylene]-6-fluoro-2-indolinone |
| 12.9 | 3-Z-[1-(4-dimethylaminomethylanilino)-1-(3-(2-benzoylaminoethyl)phenyl)methylene]-6-fluoro-2-indolinone |
| 12.10 | 3-Z-[1-(4-dimethylaminomethylanilino)-1-(3-(2-propionylaminoethyl)phenyl)methylene]-6-fluoro-2-indolinone |
| 12.11 | 3-Z-[1-(4-dimethylaminomethylanilino)-1-(3-(2-phenylacetylaminoethyl)phenyl)methylene]-6-fluoro-2-indolinone |
| 12.12 | 3-Z-[1-(4-dimethylaminomethylanilino)-1-(4-acetylaminomethylphenyl)-methylene]-6-fluoro-2-indolinone |
| 12.13 | 3-Z-[1-(4-dimethylaminomethylanilino)-1-(4-propionylaminomethylphenyl)methylene]-6-fluoro-2-indolinone |
| 12.14 | 3-Z-[1-(4-dimethylaminomethylanilino)-1-(4-phenylacetylaminomethylphenyl)methylene]-6-fluoro-2-indolinone |
| 12.15 | 3-Z-[1-(4-(N-(4-methylpiperazin-1-ylmethylcarbonyl)-N-methylamino)anilino)-1-(4-acetylaminomethylphenyl)methylene]-6-fluoro-2-indolinone |
| 12.16 | 3-Z-[1-(4-(N-(4-methylpiperazin-1-ylmethylcarbonyl)-N-methylamino)anilino)-1-(4-propionylaminomethylphenyl)methylene]-6-fluoro-2-indolinone |
| 12.17 | 3-Z-[1-(4-(N-(4-methylpiperazin-1-ylmethylcarbonyl)-N-methylamino)anilino)-1-(4-phenylacetylaminomethylphenyl)-methylene]-6-fluoro-2-indolinone |
| 12.18 | 3-Z-[1-(4-(N-(4-methylpiperazin-1-ylmethylcarbonyl)-N-methylamino)anilino)-1-(3-cyclopropylcarbonylaminomethylphenyl)-methylene]-6-fluoro-2-indolinone |

-continued

| Example | Name |
|---|---|
| 12.19 | 3-Z-[1-(4-(N-(4-methylpiperazin-1-ylmethylcarbonyl)-N-methylamino)anilino)-1-(3-cyclobutylcarbonylaminomethylphenyl)-methylene]-6-fluoro-2-indolinone |
| 12.20 | 3-Z-[1-(4-(N-(4-methylpiperazin-1-ylmethylcarbonyl)-N-methylamino)anilino)-1-(3-(pyridin-2-yl-carbonylaminomethyl)phenyl)methylene]-6-fluoro-2-indolinone |
| 12.21 | 3-Z-[1-(4-(N-(4-methylpiperazin-1-ylmethylcarbonyl)-N-methylamino)anilino)-1-(3-cyclohexylcarbonylaminomethylphenyl)-methylene]-6-fluoro-2-indolinone |
| 12.22 | 3-Z-[1-(4-(N-(4-methylpiperazin-1-ylmethylcarbonyl)-N-methylamino)anilino)-1-(3-(pyridin-3-yl-carbonylaminomethyl)phenyl)methylene]-6-fluoro-2-indolinone |
| 12.23 | 3-Z-[1-(4-(N-(4-methylpiperazin-1-ylmethylcarbonyl)-N-methylamino)anilino)-1-(3-isobutyrylaminomethylphenyl)methylene]-6-fluoro-2-indolinone |
| 12.24 | 3-Z-[1-(4-(N-(4-methylpiperazin-1-ylmethylcarbonyl)-N-methylamino)anilino)-1-(3-(3-methylbutyrylaminomethylphenyl)-methylene]-6-fluoro-2-indolinone |
| 12.25 | 3-Z-[1-(4-(N-(4-methylpiperazin-1-ylmethylcarbonyl)-N-methylamino)anilino)-1-(3-cyclohexylmethylcarbonylaminomethylphenyl)methylene]-6-fluoro-2-indolinone |
| 12.26 | 3-Z-[1-(4-(N-(4-methylpiperazin-1-ylmethylcarbonyl)-N-methylamino)anilino)-1-(3-methoxyacetylaminomethylphenyl)-methylene]-6-fluoro-2-indolinone |
| 12.27 | 3-Z-[1-(4-(N-(4-methylpiperazin-1-ylmethylcarbonyl)-N-methylamino)anilino)-1-(3-(2-methoxybenzoyl-aminomethyl)phenyl)methylene]-6-fluoro-2-indolinone |
| 12.28 | 3-Z-[1-(4-(N-(4-methylpiperazin-1-ylmethylcarbonyl)-N-methylamino)anilino)-1-(3-tert-butylacetylaminomethylphenyl)-methylene]-6-fluoro-2-indolinone |
| 12.29 | 3-Z-[1-(4-(N-(4-methylpiperazin-1-ylmethylcarbonyl)-N-methylamino)anilino)-1-(3-(2-thiophen-carbonylaminomethyl)phenyl)methylene]-6-fluoro-2-indolinone |
| 12.30 | 3-Z-[1-(4-(N-(4-methylpiperazin-1-ylmethylcarbonyl)-N-methylamino)anilino)-1-(3-pivaloylaminomethylphenyl)methylene]-6-fluoro-2-indolinone |
| 12.31 | 3-Z-[1-(4-(N-(4-methylpiperazin-1-ylmethylcarbonyl)-N-methylamino)anilino)-1-(3-(2-furoylaminomethyl)phenyl)methylene]-6-fluoro-2-indolinone |
| 12.32 | 3-Z-[1-(4-(N-(4-methylpiperazin-1-ylmethylcarbonyl)-N-methylamino)anilino)-1-(3-acetylaminomethylphenyl)methylene]-6-fluoro-2-indolinone |
| 12.33 | 3-Z-[1-(4-(N-(4-methylpiperazin-1-ylmethylcarbonyl)-N-methylamino)anilino)-1-(3-propionylaminomethylphenyl)methylene]-6-fluoro-2-indolinone |
| 12.34 | 3-Z-[1-(4-(N-(4-methylpiperazin-1-ylmethylcarbonyl)-N-methylamino)anilino)-1-(3-benzoylaminomethylphenyl)methylene]-6-fluoro-2-indolinone |
| 12.35 | 3-Z-[1-(4-(N-(4-methylpiperazin-1-ylmethylcarbonyl)-N-methylamino)anilino)-1-(3-phenylacetylaminomethylphenyl)-methylene]-6-fluoro-2-indolinone |
| 12.36 | 3-Z-[1-(4-dimethylaminomethylanilino)-1-(3-cyclopropylcarbonylaminomethylphenyl)methylene]-6-fluoro-2-indolinone |
| 12.37 | 3-Z-[1-(4-dimethylaminomethylanilino)-1-(3-cyclobutylcarbonylaminomethylphenyl)methylene]-6-fluoro-2-indolinone |
| 12.38 | 3-Z-[1-(4-dimethylaminomethylanilino)-1-(3-(pyridin-2-yl-carbonylaminomethyl)phenyl)methylene]-6-fluoro-2-indolinone |
| 12.39 | 3-Z-[1-(4-dimethylaminomethylanilino)-1-(3-cyclohexylcarbonylaminomethylphenyl)methylene]-6-fluoro-2-indolinone |
| 12.40 | 3-Z-[1-(4-dimethylaminomethylanilino)-1-(3-(pyridin-3-yl-carbonylaminomethyl)phenyl)methylene]-6-fluoro-2-indolinone |
| 12.41 | 3-Z-[1-(4-dimethylaminomethylanilino)-1-(3-isobutyrylaminomethylphenyl)methylene]-6-fluoro-2-indolinone |
| 12.42 | 3-Z-[1-(4-dimethylaminomethylanilino)-1-(3-(3-methylbutyryl-aminomethylphenyl)methylene]-6-fluoro-2-indolinone |
| 12.43 | 3-Z-[1-(4-dimethylaminomethylanilino)-1-(3-cyclohexylmethylcarbonylaminomethylphenyl)methylene]-6-fluoro-2-indolinone |
| 12.44 | 3-Z-[1-(4-dimethylaminomethylanilino)-1-(3-methoxyacetylaminomethylphenyl)methylene]-6-fluoro-2-indolinone |
| 12.45 | 3-Z-[1-(4-dimethylaminomethylanilino)-1-(3-(2-methoxybenzoyl-aminomethyl)phenyl)methylene]-6-fluoro-2-indolinone |
| 12.46 | 3-Z-[1-(4-dimethylaminomethylanilino)-1-(3-tert-butylacetylaminomethylphenyl)methylene]-6-fluoro-2-indolinone |

-continued

| Example | Name |
|---------|------|
| 12.47 | 3-Z-[1-(4-dimethylaminomethylanilino)-1-(3-(2-thiophenecarbonylaminomethyl)phenyl)methylene-6-fluoro-2-indolinone |
| 12.48 | 3-Z-[1-(4-dimethylaminomethylanilino)-1-(3-pivaloylaminomethylphenyl)methylene]-6-fluoro-2-indolinone |
| 12.49 | 3-Z-[1-(4-dimethylaminomethylanilino)-1-(3-(2-furoylaminomethyl)phenyl)methylene]-6-fluoro-2-indolinone |
| 12.50 | 3-Z-[1-(4-dimethylaminomethylanilino)-1-(3-(pyridin-4-yl-carbonylaminomethyl)phenyl)methylene]-6-fluoro-2-indolinone |
| 13.0 | 3-Z-[1-(4-trimethylammoniummethylanilino)-1-(4-(2-carboxyethyl)phenyl)methylene]-6-fluoro-2-indolinone iodide |
| 13.1 | 3-Z-[1-(4-trimethylammoniummethylanilino)-1-(3-(2-carboxyethyl)phenyl)methylene]-6-fluoro-2-indolinone iodide |
| 14.0 | 3-Z-[1-(4-guanidinomethylanilino)-1-(4-(2-carboxyethyl)phenyl)methylene]-6-fluoro-2-indolinone |
| 14.1 | 3-Z-[1-(4-guanidinomethylanilino)-1-(3-(2-carboxyethyl)phenyl)methylene]-6-fluoro-2-indolinone |

Abbreviations used:
HOBt=1-hydroxy-1H-benzotriazole
TBTU=O-benzotriazol-1-yl-N,N,N',N'-tetramethyluronium tetrafluoroborate Preparation of the Starting Materials:

EXAMPLE I

Dimethyl 2-(4-fluoro-2-nitrophenyl)malonate

With ice-cooling, 185 g of potassium tert-butoxide are added to a solution of 188 ml of dimethyl malonate in 970 ml of N-methylpyrrolidone, and the mixture is stirred for 2 hours. Over a period of 30 minutes, 150 ml of 2,5-difluoronitrobenzene are added dropwise to the resulting slurry, and the mixture is then stirred at 85° C. for 6 hours. The mixture is poured into 4 liters of ice-water and 250 ml of concentrated hydrochloric acid and extracted with 2 liters of ethyl acatate. The organic phase is dried with sodium sulphate and concentrated. The oily residue is triturated twice with water and then taken up in 600 ml of ethyl acetate. The solution is dried with sodium sulphate and concentrated to dryness. The resulting crude product is recrystallized from 600 ml of ethyl acetate/hexane=2:8 and dried.

Yield: 222 g (59% of theory)
$R_f$ value: 0.40 (silica gel, cyclohexane/ethyl acetate=5:1)
$C_{11}H_{10}FNO_6$
Mass spectrum: m/z=270 [M–H]⁻

The following compounds are prepared analogously to Example I:
(I.1) Diethyl 2-(4-bromo-2-nitrophenyl)malonate from 2,5-dibromonitrobenzene and diethyl malonate
$R_f$ value: 0.40 (silica gel, petroleum ether/ethyl acetate=5:1)
$C_{13}H_{14}BrNO_6$
Mass spectrum: m/z=359/361 [M]⁺
(I.2) Dimethyl 2-(4-cyano-2-nitrophenyl)malonate from 4-chloro-3-nitrobenzonitrile and dimethyl malonate
$R_f$ value: 0.50 (silica gel, methylene chloride/methanol=50:1)
$C_{12}H_{10}N_2O_6$
Mass spectrum: m/z=277 [M–H]⁻

EXAMPLE II

Methyl 4-cyano-2-nitrophenylacetate 14.2 g of dimethyl 2-(4-cyano-2-nitrophenyl)malonate (starting material 1.2) are dissolved in 200 ml of dimethyl sulphoxide, and 4.5 g of lithium chloride and 1.0 ml of water are added. The solution is stirred at 100° C. for 3.5 hours, 300 ml of ice-water are then added and the mixture is allowed to stand for 12 hours. The resulting precipitate is filtered off with suction, taken up in methylene chloride and washed with water. The organic phase is dried over sodium sulphate, concentrated using a rotary evaporator and dried.

Yield: 7.7 g (68% of theory)
$R_f$ value: 0.40 (silica gel, methylene chloride/methanol) =50:1
$C_{10}H_8N_2O_4$
Mass spectrum: m/z=219 [M–H]⁻

EXAMPLE III

4-Fluoro-2-nitrophenylacetic acid

At 100° C., 50.0 g of dimethyl 2-(4-fluoro-2-nitrophenyl) malonate (starting material I) are stirred in 400 ml of 6 molar hydrochloric acid for 20 hours, 400 ml of water are then added and the mixture is cooled to 0° C. The resulting precipitate is filtered off with suction, washed with water and 100 ml of petroleum ether and dried.

Yield: 34.5 g (94% of theory)
$R_f$ value: 0.30 (silica gel, cyclohexane/ethyl acetate)=5:2
$C_8H_6FNO_4$
Mass spectrum: m/z=154 [M-COO—H]⁻

EXAMPLE IV

6-Fluoro-2-indolinone

With addition of 20 g of palladium on activated carbon (10%), 119 g of 4-fluoro-2-nitrophenylacetic acid (starting material III) are hydrogenated in 600 ml of acetic acid under a hydrogen pressure of 50 psi. The catalyst is filtered off with suction and the solvent is distilled off. The crude product is triturated with 500 ml of petroleum ether, filtered off with suction, washed with water and dried.

Yield: 82.5 g (91% of theory)

R$_f$ value: 0.30 (silica gel, petroleum ether/ethyl acetate 1:1)

C$_8$H$_6$FNO

Mass spectrum: m/z=150 [M−H]$^-$

The following compounds are prepared analogously to Example IV:

(IV.1) 6-Bromo-2-indolinone from diethyl 2-(4-bromo-2-nitrophenyl)malonate (starting material I.1) using Raney nickel as hydrogenation catalyst R$_f$ value: 0.45 (silica gel, petroleum ether/ethyl acetate=1:1)

C$_8$H$_6$BrNO

Mass spectrum: m/z=210/212 [M−H]$^-$ (IV.2) 6-Cyano-2-indolinone from methyl 4-cyano-2-nitrophenylacetate (starting material II) using palladium/calcium carbonate as hydrogenation catalyst R$_f$ value: 0.45 (silica gel, methylene chloride/methanol=9:1)

C$_9$H$_6$N$_2$O

Mass spectrum: m/z=157 [M−H]$^-$

EXAMPLE V 1-acetyl-6-fluoro-2-indolinone

At 130° C., 82.5 g of 6-fluoro-2-indolinone (starting material IV) are stirred in 180 ml acetic anhydride for 3 hours. After cooling to room temperature, the precipitate is filtered off with suction, washed with 100 ml of petroleum ether and dried.

Yield: 64.8 g (61% of theory)

R$_f$ value: 0.75 (silica gel, petroleum ether/ethyl acetate=1:1)

C$_{10}$H$_8$FNO$_2$

Mass spectrum: m/z=192 [M−H]$^-$

The following compounds are prepared analogously to Example V:

(V.1) 1-acetyl-6-chloro-2-indolinone from 6-chloro-2-indolinone and acetic anhydride R$_f$ value: 0.55 (silica gel, petroleum ether/ethyl acetate=2:3)

C$_{11}$H$_{10}$ClNO$_6$

Mass spectrum: m/z=208/210 [M−H]$^-$ (V.2) 1-acetyl-6-bromo-2-indolinone from 6-bromo-2-indolinone (starting material IV.1) and acetic anhydride R$_f$ value: 0.60 (silica gel, petroleum ether/ethyl acetate=2:1)

C$_{10}$H$_8$BrNO$_2$

Mass spectrum: m/z=253/255 [M]$^+$ (V.3) 1-acetyl-6-cyano-2-indolinone from 6-cyano-2-indolinone (starting material IV.2) and acetic anhydride R$_f$ value: 0.60 (silica gel, methylene chloride/methanol=50:1)

C$_{11}$H$_8$N$_2$O$_2$

Mass spectrum: m/z=199 [M−H]$^-$

EXAMPLE VI 1-acetyl-3-[1-hydroxy-1-(3-iodophenyl)methylene]-6-chloro-2-indolinone 10.5 g of 1-acetyl-6-chloro-2-indolinone (starting material V.1), 13.6 g of 3-iodobenzoic acid and 17.7 g of TBTU are initially charged in 100 ml of dimethylformamide, 35 ml of triethylamine are added and the mixture is stirred at room temperature for 12 hours. After this time, the solvent is removed under reduced pressure, water is added to the residue and the residue is filtered off with suction, washed with a little water, methanol and ether and dried at 100° C. under reduced pressure.

Yield: 12.9 g (59% of theory)

R$_f$ value: 0.80 (silica gel, methylene chloride/methanol=9:1)

C$_{17}$H$_{11}$ClINO$_3$

Mass spectrum: m/z=438/440 [M−H]$^-$

The following compounds are prepared analogously to Example VI:

(VI.1) 1-acetyl-3-[1-hydroxy-1-(4-methoxycarbonylmethylphenyl)methylene]-6-fluoro-2-indolinone from 1-acetyl-6-fluoro-2-indolinone (starting material V) and methyl (4-carboxyphenyl)acetate (preparation according to Tetrahedron 1997, 53, 7335–7340)

(VI.2) 1-acetyl-3-[1-hydroxy-1-(4-chlorophenyl)methylene]-6-chloro-2-indolinone from 1-acetyl-6-chloro-2-indolinone (starting material V.1) and 4-chlorobenzoic acid (VI.3) 1-acetyl-3-[1-hydroxy-1-(3,4-dimethoxyphenyl)methylene]-6-chloro-2-indolinone from 1-acetyl-6-chloro-2-indolinone (starting material V.1) and 3,4-dimethoxybenzoic acid (VI.4) 1-acetyl-3-[1-hydroxy-1-(3,4-dimethoxyphenyl)methylene]-6-cyano-2-indolinone from 1-acetyl-6-cyano-2-indolinone (starting material V.3) and 3,4-dimethoxybenzoic acid (VI.5) 1-acetyl-3-[1-hydroxy-1-(3-fluorophenyl)methylene]-6-fluoro-2-indolinone from 1-acetyl-6-fluoro-2-indolinone (starting material V) and 3-fluorobenzoic acid (VI.6) 1-acetyl-3-[1-hydroxy-1-(4-(2-acetylaminoethyl)phenyl)methylene]-6-fluoro-2-indolinone from 1-acetyl-6-fluoro-2-indolinone (starting material V) and 4-(2-acetylaminoethyl)-benzoic acid (preparation according to J. Am. Chem. Soc. 1943, 65, 2377)

(VI.7) 1-acetyl-3-[1-hydroxy-1-(3-methoxycarbonylmethylphenyl)methylene]-6-fluoro-2-indolinone from 1-acetyl-6-fluoro-2-indolinone (starting material V) and methyl (3-carboxyphenyl)acetate (preparation analogously to Tetrahedron 1997, 53, 7335–7340)

(VI.8) 1-acetyl-3-[1-hydroxy-1-(3-(N-tert-butoxycarbonylaminomethyl)phenyl)-methylene]-6-fluoro-2-indolinone from 1-acetyl-6-fluoro-2-indolinone (starting material V) and 3-(N-tert-butoxycarbonyl-aminomethyl)benzoic acid (preparation according to Tetrahedron 1997, 53, 7335–7340)

(VI.9) 1-acetyl-3-[1-hydroxy-1-(3-cyanomethylphenyl)methylene]-6-fluoro-2-indolinone from 1-acetyl-6-fluoro-2-indolinone (starting material V) and (3-carboxyphenyl)-acetonitrile (preparation according to J. Prakt. Chem. 1998, 340, 367–374)

(VI.10) 1-acetyl-3-[1-hydroxy-1-(4-(N-tert-butoxycarbonylaminomethyl)phenyl)-methylene]-6-fluoro-2-indolinone from 1-acetyl-6-fluoro-2-indolinone (starting material V) and 4-(N-tert-butoxycarbonyl-aminomethyl)benzoic acid (preparation according to Bioorg. Med. Chem. Lett 2000, 10, 553–557)
(VI.11) 1-acetyl-3-[1-hydroxy-1-(4-iodophenyl)methylene]-6-fluoro-2-indolinone from 1-acetyl-6-fluoro-2-indolinone (starting material V) and 4-iodobenzoic acid
(VI.12) 1-acetyl-3-[1-hydroxy-1-(4-iodophenyl)methylene]-6-chloro-2-indolinone from 1-acetyl-6-chloro-2-indolinone (starting material V.1) and 4-iodobenzoic acid
(VI.13) 1-acetyl-3-[1-hydroxy-1-(3-iodophenyl)methylene]-6-fluoro-2-indolinone from 1-acetyl-6-fluoro-2-indolinone (starting material V) and 3-iodobenzoic acid
(VI.14) 1-acetyl-3-[1-hydroxy-1-(4-(2-methoxycarbonylethyl)phenyl)methylene]-6-fluoro-2-indolinone from 1-acetyl-6-fluoro-2-indolinone (starting material V) and 4-(2-methoxycarbonylethyl)benzoic acid (preparation analogously to Tetrahedron 1997, 53, 7335–7340)
(VI.15) 1-acetyl-3-[1-hydroxy-1-(3-(2-methoxycarbonylethyl)phenyl)methylene]-6-fluoro-2-indolinone from 1-acetyl-6-fluoro-2-indolinone (starting material V) and 3-(2-methoxycarbonylethyl)benzoic acid (preparation analogously to Tetrahedron 1997, 53, 7335–7340)
(VI.16) 1-acetyl-3-[1-hydroxy-1-(3-(N-tert-butoxycarbonyl-2-aminoethyl)phenyl)methylene]-6-fluoro-2-indolinone from 1-acetyl-6-fluoro-2-indolinone (starting material V) and 3-(N-tert-butoxycarbonyl-2-aminoethyl)benzoic acid (preparation analogously to Bioorg. Med. Chem. Lett 2000, 10, 553–557)
(VI.17) 1-acetyl-3-[1-hydroxy-1-(4-(N-tert-butoxycarbonyl-2-aminoethyl)phenyl)methylene]-6-fluoro-2-indolinone from 1-acetyl-6-fluoro-2-indolinone (starting material V) and 4-(N-tert-butoxycarbonyl-2-aminoethyl)benzoic acid (preparation analogously to Bioorg. Med. Chem. Lett 2000, 10, 553–557)
(VI.18) 1-acetyl-3-[1-hydroxy-1-(4-cyanophenyl)methylene]-6-chloro-2-indolinone from 1-acetyl-6-chloro-2-indolinone (starting material V.1) and 4-cyanobenzoic acid
(VI.19) 1-acetyl-3-[1-hydroxy-1-(3-acetylaminomethylphenyl)methylene]-6-fluoro-2-indolinone from 1-acetyl-6-fluoro-2-indolinone (starting material V) and 3-acetylaminomethyl-benzoic acid (prepared according to J. Med. Chem. 1997, 40, 4030–4052)
(VI.20) 1-acetyl-3-[1-hydroxy-1-(3-(2-ethoxycarbonylethyl)phenyl)methylene]-6-fluoro-2-indolinone from 1-acetyl-6-fluoro-2-indolinone (starting material V) and 3-(2-ethoxycarbonylethyl)benzoic acid (preparation analogously to Tetrahedron 1997, 53, 7335–7340)
(VI.21) 1-acetyl-3-[1-hydroxy-1-(4-(2-methoxycarbonylethyl)phenyl)methylene]-6-chloro-2-indolinone from 1-acetyl-6-chloro-2-indolinone (starting material V.1) and 4-(2-methoxycarbonylethyl)benzoic acid (preparation analogously to Tetrahedron 1997, 53, 7335–7340)

(VI.22) 1-acetyl-3-[1-hydroxy-1-(4-(2-ethoxycarbonylethyl)phenyl)methylene]-6-fluoro-2-indolinone from 1-acetyl-6-fluoro-2-indolinone (starting material V) and 4-(2-ethoxycarbonylethyl)benzoic acid (preparation analogously to Tetrahedron 1997, 53, 7335–7340)
(VI.23) 1-acetyl-3-[1-hydroxy-1-(3-methoxycarbonylmethyloxy-phenyl)methylene]-6-fluoro-2-indolinone from 1-acetyl-6-fluoro-2-indolinone (starting material V) and 3-methoxycarbonylmethyloxybenzoic acid (preparation see Tetrahedron Letters 1998, 39, 8563–8566)
(VI.24) 1-acetyl-3-[1-hydroxy-1-(4-methoxycarbonylmethyloxyphenyl)methylene]-6-fluoro-2-indolinone from 1-acetyl-6-fluoro-2-indolinone (starting material V) and 4-methoxycarbonylmethyloxybenzoic acid (preparation analogously to Tetrahedron Letters 1998, 39, 8563–8566)
(VI.25) 1-acetyl-3-[1-hydroxy-1-(3-(2-ethoxycarbonylethyloxy)phenyl)methylene]-6-fluoro-2-indolinone from 1-acetyl-6-fluoro-2-indolinone (starting material V) and 3-(2-ethoxycarbonylethyloxy)benzoic acid (preparation see PCT Int. Appl. WO9620173, 60)
(VI.26) 1-acetyl-3-[1-hydroxy-1-(4-(2-ethoxycarbonylethyloxy)phenyl)methylene]-6-fluoro-2-indolinone from 1-acetyl-6-fluoro-2-indolinone (starting material V) and 4-(2-ethoxycarbonylethyloxy)benzoic acid (preparation see PCT Int. Appl. WO9620173, 58)
(VI.27) 1-acetyl-3-[1-hydroxy-1-(4-(2-methoxycarbonylethyl)phenyl)methylene]-6-bromo-2-indolinone from 1-acetyl-6-bromo-2-indolinone (starting material V.2) and 4-(2-methoxycarbonylethyl)-benzoic acid (preparation analogously to Tetrahedron 1997, 53, 7335–7340)

EXAMPLE VII 1-acetyl-3-[1-methoxy-1-(3-iodophenyl)methylene]-6-chloro-2-indolinone A little at a time, 2.36 g of trimethyloxonium tetrafluoroborate are added to a solution of 3.52 g of 1-acetyl-3-[1-hydroxy-1-(3-iodophenyl)methylene]-6-chloro-2-indolinone (starting material VI) and 2.72 ml of ethyldiisopropylamine in 80 ml of dichloromethane, and the mixture is stirred at room temperature for one hour. Another 1.4 ml of ethyldiisopropylamine and 1.2 g of trimethyloxonium tetrafluoroborate are added, and the mixture is stirred at room temperature for another two hours. The mixture is then extracted with water and the organic phase is dried over magnesium sulphate and evaporated to dryness. The residue is recrystallized from ether and dried at 80° C. under reduced pressure.

Yield: 2.40 g (66% of theory)

$R_f$ value: 0.60 (silica gel, petroleum ether/dichloromethane/ethyl acetate=5:4:1)

$C_{18}H_{13}ClINO_3$

Mass spectrum: m/z=438/440 [M–H]$^-$ m.p. 185–187° C.

The following compounds are prepared analogously to Example VII:
(VII.1) 1-acetyl-3-[1-methoxy-1-(4-methoxycarbonylmethylphenyl)methylene]-6-fluoro-2-indolinone from 1-acetyl-3-[1-hydroxy-1-(4-methoxycarbonylmethylphenyl)methylene]-6-fluoro-2-indolinone (starting material VI.1)

(VII.2) 1-acetyl-3-[1-methoxy-1-(4-chlorophenyl)methylene]-6-chloro-2-indolinone from 1-acetyl-3-[1-hydroxy-1-(4-chlorophenyl)methylene]-6-chloro-2-indolinone (starting material VI.2)

(VII.3) 1-acetyl-3-[1-methoxy-1-(3,4-dimethoxyphenyl)methylene]-6-chloro-2-indolinone from 1-acetyl-3-[1-hydroxy-1-(3,4-dimethoxyphenyl)methylene]-6-chloro-2-indolinone (starting material VI.3)

(VII.4) 1-acetyl-3-[1-methoxy-1-(3,4-dimethoxyphenyl)methylene]-6-cyano-2-indolinone from 1-acetyl-3-[1-hydroxy-1-(3,4-dimethoxyphenyl)-methylene]-6-cyano-2-indolinone (starting material VI.4)

(VII.5) 1-acetyl-3-[1-methoxy-1-(3-fluorophenyl)methylene]-6-fluoro-2-indolinone from 1-acetyl-3-[1-hydroxy-1-(3-fluorophenyl)methylene]-6-fluoro-2-indolinone (starting material VI.5)

(VII.6) 1-acetyl-3-[1-methoxy-1-(4-(2-acetylaminoethyl)phenyl)methylene]-6-fluoro-2-indolinone from 1-acetyl-3-[1-hydroxy-1-(4-(2-acetylaminoethyl)phenyl)methylene]-6-fluoro-2-indolinone (starting material VI.6)

(VII.7) 1-acetyl-3-[1-methoxy-1-(3-methoxycarbonylmethylphenyl)methylene]-6-fluoro-2-indolinone from 1-acetyl-3-[1-hydroxy-1-(3-methoxycarbonylmethylphenyl)methylene]-6-fluoro-2-indolinone (starting material VI.7)

(VII.8) 1-acetyl-3-[1-methoxy-1-(3-(N-tert-butoxycarbonylaminomethyl)phenyl)-methylene]-6-fluoro-2-indolinone from 1-acetyl-3-[1-hydroxy-1-(3-(N-tert-butoxycarbonylaminomethyl)phenyl)methylene]-6-fluoro-2-indolinone (starting material VI.8)

(VII.9) 1-acetyl-3-[1-methoxy-1-(3-cyanomethylphenyl)methylene]-6-fluoro-2-indolinone from 1-acetyl-3-[1-hydroxy-1-(3-cyanomethyl phenyl)methylene]-6-fluoro-2-indolinone (starting material VI.9)

(VII.10) 1-acetyl-3-[1-methoxy-1-(4-(N-tert-butoxycarbonyl-aminomethyl)phenyl)methylene]-6-fluoro-2-indolinone from 1-acetyl-3-[1-hydroxy-1-(4-(N-tert-butoxycarbonyl-aminomethyl)phenyl)methylene]-6-fluoro-2-indolinone (starting material VI.10)

(VII.11) 1-acetyl-3-[1-methoxy-1-(4-iodophenyl)methylene]-6-fluoro-2-indolinone from 1-acetyl-3-[1-hydroxy-1-(4-iodophenyl)methylene]-6-fluoro-2-indolinone (starting material VI.11)

(VII.12) 1-acetyl-3-[1-methoxy-1-(4-iodophenyl)methylene]-6-chloro-2-indolinone from 1-acetyl-3-[1-hydroxy-1-(4-iodophenyl)methylene]-6-chloro-2-indolinone (starting material VI.12)

(VII.13) 1-acetyl-3-[1-methoxy-1-(3-iodophenyl)methylene]-6-fluoro-2-indolinone from 1-acetyl-3-[1-hydroxy-1-(3-iodophenyl)methylene]-6-fluoro-2-indolinone (starting material VI.13)

(VII.14) 1-acetyl-3-[1-methoxy-1-(3-(2-methoxycarbonylethyl)phenyl)methylene]-6-fluoro-2-indolinone from 1-acetyl-3-[1-hydroxy-1-(3-(2-methoxycarbonylethyl)phenyl)methylene]-6-fluoro-2-indolinone (starting material VI.14)

(VII.15) 1-acetyl-3-[1-methoxy-1-(4-(2-methoxycarbonylethyl)phenyl)methylene]-6-fluoro-2-indolinone from 1-acetyl-3-[1-hydroxy-1-(4-(2-methoxycarbonylethyl)phenyl)methylene]-6-fluoro-2-indolinone (starting material VI.15)

(VII.16) 1-acetyl-3-[1-methoxy-1-(4-(N-tert-butoxycarbonyl-2-aminoethyl)phenyl)methylene]-6-fluoro-2-indolinone from 1-acetyl-3-[1-hydroxy-1-(4-(N-tert-butoxycarbonyl-2-aminoethyl)phenyl)methylene]-6-fluoro-2-indolinone (starting material VI.17)

(VII.17) 1-acetyl-3-[1-methoxy-1-(3-(N-tert-butoxycarbonyl-2-aminoethyl)phenyl)methylene]-6-fluoro-2-indolinone from 1-acetyl-3-[1-hydroxy-1-(3-(N-tert-butoxycarbonyl-2-aminoethyl)phenyl)methylene]-6-fluoro-2-indolinone (starting material VI.16)

(VII.18) 1-acetyl-3-[1-methoxy-1-(3-acetylaminomethylphenyl)methylene]-6-fluoro-2-indolinone from 1-acetyl-3-[1-hydroxy-1-(3-acetylaminomethylphenyl)methylene]-6-fluoro-2-indolinone (starting material VI.19)

(VII.19) 1-acetyl-3-[1-methoxy-1-(3-(2-ethoxycarbonylethyl)phenyl)methylene]-6-fluoro-2-indolinone from 1-acetyl-3-[1-hydroxy-1-(3-(2-ethoxycarbonylethyl)phenyl)methylene]-6-fluoro-2-indolinone (starting material VI.20)

(VII.20) 1-acetyl-3-[1-methoxy-1-(4-(2-methoxycarbonylethyl)phenyl)methylene]-6-chloro-2-indolinone from 1-acetyl-3-[1-hydroxy-1-(4-(2-methoxycarbonylethyl)phenyl)methylene]-6-chloro-2-indolinone (starting material VI.21)

(VII.21) 1-acetyl-3-[f-methoxy-1-(4-(2-ethoxycarbonylethyl)phenyl)methylene]-6-fluoro-2-indolinone from 1-acetyl-3-[1-hydroxy-1-(4-(2-ethoxycarbonylethyl)phenyl)methylene]-6-fluoro-2-indolinone (starting material VI.22)

(VII.22) 1-acetyl-3-[1-methoxy-1-(4-methoxycarbonylmethyloxyphenyl)-methylene]-6-fluoro-2-indolinone from 1-acetyl-3-[1-hydroxy-1-(4-methoxycarbonylmethyloxyphenyl)methylene]-6-fluoro-2-indolinone (starting material VI.23)

(VII.23) 1-acetyl-3-[1-methoxy-1-(3-methoxycarbonylmethyloxyphenyl)methylene]-6-fluoro-2-indolinone from 1-acetyl-3-[1-hydroxy-1-(3-methoxycarbonylmethyloxyphenyl)methylene]-6-fluoro-2-indolinone (starting material VI.24)

(VII.24) 1-acetyl-3-[1-methoxy-1-(3-(2-ethoxycarbonylethyloxy)phenyl)methylene]-6-fluoro-2-indolinone from 1-acetyl-3-[1-hydroxy-1-(3-(2-ethoxycarbonylethyloxy)phenyl)methylene]-6-fluoro-2-indolinone (starting material VI.25)

(VII.25) 1-acetyl-3-[1-methoxy-1-(4-(2-ethoxycarbonylethyloxy)phenyl)methylene]-6-fluoro-2-indolinone from 1-acetyl-3-[1-hydroxy-1-(4-(2-ethoxycarbonylethyloxy)phenyl)methylene]-6-fluoro-2-indolinone (starting material VI.26)

(VII.26) 1-acetyl-3-[1-methoxy-1-(4-(2-methoxycarbonylethyl)phenyl)methylene]-6-bromo-2-indolinone from 1-acetyl-3-[1-hydroxy-1-(4-(2-methoxycarbonylethyl)phenyl)methylene]-6-bromo-2-indolinone (starting material VI.27)

EXAMPLE VIII

1-Acetyl-3-[1-chloro-1-(4-cyanophenyl)methylene]-6-chloro-2-indolinone

A suspension of 7.0 g of 1-acetyl-3-[1-hydroxy-1-(4-cyanophenyl)methylene]-6-chloro-2-indolinone (starting material VI.18) and 6.39 g of phosphorus pentachloride in 150 ml of dioxane is stirred at 100° C. for 6 hours. After addition of a further 1.0 g of phosphorus pentachloride, the mixture is stirred at 110° C. for another 4 hours. The solvent is then distilled off and the residue is washed with ethyl acetate.

Yield: 4.5 g (61% of theory)
$R_f$ value: 0.70 (silica gel, methylene chloride/methanol=50:1)
$C_{18}H_{10}Cl_2N_2O_2$

EXAMPLE IX

The syntheses of the following compounds have already been described in the international application WO 01/27081:
(IX.1) 4-(diethylaminomethyl)aniline
(IX.2) N-(2-dimethylaminoethyl)-N-methylsulphonyl-p-phenylenediamine
(IX.3) 3-(dimethylaminomethyl)aniline
(IX.4) 4-(dimethylaminomethyl)aniline
(IX.5) 4-(2-dimethylaminoethyl)aniline
(IX.6) 4-[N-(2-dimethylaminoethyl)-N-acetylamino]aniline
(IX.7) 4-[N-(3-dimethylaminopropyl)-N-acetylamino]aniline
(IX.8) 4-[(N-dimethylaminocarbonylmethyl-N-methylsulphonyl)amino]aniline
(IX.9) N-(4-aminophenyl)-N-methylmethanesulphonamide
(IX.10) N-(dimethylaminomethylcarbonyl)-N-methyl-p-phenylenediamine
(IX.11) N-[(2-dimethylaminoethyl)carbonyl]-N-methyl-p-phenylenediamine
(IX.12) 4-(N-tert-butoxycarbonylaminomethyl)aniline
(IX.13) 4-(N-ethyl-N-tert-butoxycarbonylaminomethyl)aniline
(IX.14) 4-[(4-methylpiperazin-1-yl)methyl]aniline
(IX.15) 4-(imidazol-1-ylmethyl)aniline
(IX.16) 4-(1-methylimidazol-2-yl)aniline
(IX.17) 4-[(N-(2-dimethylaminoethyl)-N-methylamino)methyl]aniline
(IX.18) 4-(N-methyl-N-tert-butoxycarbonylaminomethyl)aniline
(IX.19) N-[(4-methylpiperazin-1-yl)methylcarbonyl]-N-methyl-p-phenylenediamine
(IX.20) 4-(4-tert-butoxycarbonylpiperazin-1-ylmethyl)aniline
(IX.21) 4-(thiomorpholin-4-ylmethyl)aniline
(IX.22) 4-(pyrrolidin-1-ylmethyl)aniline
(IX.23) 4-(morpholin-4-yl-methyl)aniline
(IX.24) 4-(N-benzyl-N-methylaminomethyl)aniline
(IX.25) 4-(N-ethyl-N-methylaminomethyl)aniline
(IX.26) 4-[N-(2-dimethylaminoethyl)-N-methylamino]aniline
(IX.27) 4-[(N-propyl-N-methylamino)methyl]aniline The following compounds are prepared analogously to Example IX:
(IX.28) 4-[N-(2-(N-benzyl-N-methylamino)ethyl)-N-acetylamino]aniline
(IX.29) 4-amino-N-(2-dimethylaminoethyl)-N-methylbenzamide
(IX.30) 4-(4-methylpiperazin-1-ylcarbonyl)aniline
(IX.31) 4-(2-dimethylaminoethoxy)aniline
(IX.32) N-(4-dimethylaminobutylcarbonyl)-N-methyl-p-phenylenediamine
(IX.33) N-[(3-dimethylaminopropyl)carbonyl]-N-methyl-p-phenylenediamine Preparation of the End Products:

EXAMPLE 1.0

3-Z-[1-(4-(N-Methyl-N-methylsulphonylamino)anilino)-1-(3-iodophenyl)methylene]-6-chloro-2-indolinone 0.9 g of 1-acetyl-3-(1-methoxy-1-(3-iodophenyl)methylene)-6-chloro-2-indolinone (starting material VII) and 0.5 g of N-methyl-N-methylsulphonyl-p-phenylenediamine (starting material IX.9) are dissolved in 10 ml of dimethylformamide and stirred at 120° C. for 3 hours. After cooling, 1.5 ml of piperidine are added and the mixture is stirred at room temperature for another hour. Water is added and the resulting precipitate is filtered off with suction, washed with a little water, methanol and ether and finally dried under reduced pressure at 100° C.

Yield: 0.9 g (74% of theory), $R_f$ value: 0.6 (silica gel, methylene chloride/methanol=9:1)
m.p. 292–294° C.
$C_{23}H_{19}ClIN_3O_3S$
Mass spectrum: m/z=578/580 [M–H]⁻

The following compounds of the formula I-1 are prepared analogously to Example 1.0:

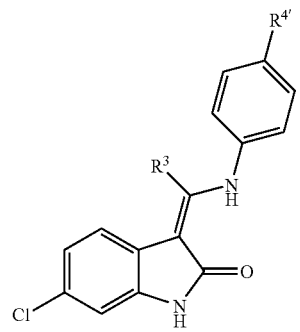

(I-1)

| Example | R³ | R⁴' | Starting materials | Empirical formula | Mass spectrum | m.p. [°C.] | $R_f$ value* |
|---|---|---|---|---|---|---|---|
| 1.1 | 3-iodophenyl | —CH₂—NMe₂ | VII IX.4 | $C_{24}H_{21}ClIN_3O$ | 529/531 [M+H]⁺ | 238–240 | 0.30(A) |
| 1.2 | 4-chlorophenyl | —N(Me)—(CO)—CH₂—NMe₂ | VII.2 IX.10 | $C_{26}H_{24}Cl_2N_4O_2$ | 495/497 [M+H]⁺ | 277–279 | 0.20(B) |
| 1.3 | 4-chlorophenyl | —N(COMe)—(CH₂)₂—NMe₂ | VII.2 IX.6 | $C_{27}H_{26}Cl_2N_4O_2$ | 507/509 [M−H]⁻ | 241–243 | 0.10(B) |
| 1.4 | 4-chlorophenyl | N-Me-piperazinyl-CH₂-C(O)-N(Me)- | VII.2 IX.19 | $C_{29}H_{29}Cl_2N_5O_2$ | 548/550 [M−H]⁻ | 266–268 | 0.10(B) |
| 1.5 | 4-chlorophenyl | —N(COMe)—(CH₂)₃—NMe₂ | VII.2 IX.7 | $C_{28}H_{28}Cl_2N_4O_2$ | 521/523 [M−H]⁻ | 241–242 | 0.10(B) |
| 1.6 | 4-chlorophenyl | —CH₂—NMe₂ | VII.2 IX.4 | $C_{24}H_{21}Cl_2N_3O$ | 438/440 [M+H]⁺ | 243–244 | 0.10(B) |

-continued

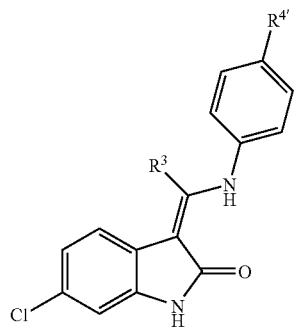
(I-1)

| Example | R³ | R⁴' | Starting materials | Empirical formula | Mass spectrum | m.p. [°C.] | R_f value* |
|---|---|---|---|---|---|---|---|
| 1.7 | MeO, OMe (3,4-dimethoxyphenyl) | —N(COMe)—(CH₂)₂—NMe₂ | VII.3 IX.6 | $C_{29}H_{31}ClN_4O_4$ | 533/535 [M−H]⁻ | 128–130 | 0.75(C) |
| 1.8 | MeO, OMe (3,4-dimethoxyphenyl) | Me-N-C(=O)-CH₂-piperazine-N-Me | VII.3 IX.19 | $C_{31}H_{34}ClN_5O_4$ | 574/576 [M−H]⁻ | 208–210 | 0.65(C) |
| 1.9 | MeO, OMe (3,4-dimethoxyphenyl) | —N(SO₂Me)—(CH₂)₂—NMe₂ | VII.3 IX.2 | $C_{28}H_{31}ClN_4O_5S$ | 569/571 [M−H]⁻ | 198–200 | 0.75(C) |
| 1.10 | MeO, OMe (3,4-dimethoxyphenyl) | —CH₂—NMe₂ | VII.3 IX.4 | $C_{26}H_{26}ClN_3O_3$ | 462/464 [M−H]⁻ | 239–240 | 0.70(C) |
| 1.11 | MeO, OMe (3,4-dimethoxyphenyl) | C(=O)-N(Me)-CH₂CH₂-NMe₂ | VII.3 IX.29 | $C_{29}H_{31}ClN_4O_4$ | 533/535 [M−H]⁻ | 147–149 | 0.70(C) |

*Eluent mixtures:
(A): silica gel, methylene chloride/methanol 9:1
(B): silica gel, methylene chloride/ethanol 10:1
(C): silica gel, methylene chloride/methanol 4:1

EXAMPLE 2.0

3-Z-[1-(4-(Dimethylaminomethyl)anilino)-1-(4-cyanophenyl)methylene]-6-chloro-2-indolinone 1.07 g of 1-acetyl-3-[1-chloro-1-(4-cyanophenyl)methylene]-6-chloro-2-indolinone (starting material VII) and 0.54 g of 4-(dimethylaminomethyl)aniline (starting material IX.4) are dissolved in 10 ml of dimethylformamide and stirred at 80° C. for 3 hours. After cooling, 1 ml of 6N aqueous sodium hydroxide is added, and the mixture is stirred at room temperature for 30 minutes. Water is added and the mixture is extracted three times with methylene chloride. The combined organic phases are washed twice with water, dried over sodium sulphate and concentrated using a rotary evaporator, and the product is recrystallized from diethyl ether.

Yield: 0.92 g (72% of theory), $R_f$ value: 0.1 (silica gel, methylene chloride/methanol=9:1)

$C_{25}H_{21}ClN_4O$

Mass spectrum: m/z=427/429 [M–H]$^-$

EXAMPLE 3.0

3-Z-[1-(4-(dimethylaminomethyl)anilino)-1-(4-iodophenyl)methylene]-6-fluoro-2-indolinone 3.5 g of 1-acetyl-3-(1-methoxy-1-(4-iodophenyl)methylene)-6-fluoro-2-indolinone (starting material VII.11) and 1.6 g of 4-(dimethylaminomethyl)aniline (starting material IX.4) are dissolved in 30 ml of dimethylformamide and stirred at 120° C. for 2 hours. After cooling, the solvent is removed under reduced pressure, the residue is taken up in 30 ml of methanol and 2 spatula tips of sodium methoxide are added. Once a yellow precipitate has formed, this is filtered off with suction from the solvent and the residue is washed with a little methanol and ether and finally dried under reduced pressure at 100° C.

Yield: 1.9 g (46% of theory), $R_f$ value: 0.3 (silica gel, methylene chloride/methanol=9:1)

m.p. 243–246° C.

$C_{24}H_{21}FIN_3O$

Mass spectrum: m/z=514 [M+H]$^+$

The following compounds of the formula I-3a are prepared analogously to Example 3.0:

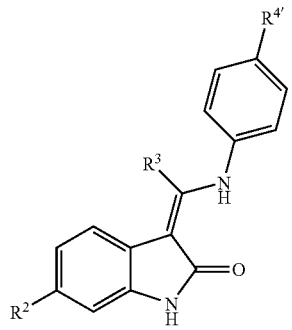

(I-3a)

| Example | R² | R³ | R⁴' | Starting materials | Empirical formula | Mass spectrum | m.p. [° C.] | $R_f$ value* |
|---|---|---|---|---|---|---|---|---|
| 3.1 | -F | 3-F-phenyl | —CH₂—NMe₂ | VII.5 IX.4 | $C_{24}H_{21}F_2N_3O$ | 404 [M–H]$^-$ | 225–227 | 0.20(A) |
| 3.2 | -F | 3-F-phenyl | —N(COMe)—(CH₂)₃—NMe₂ | VII.5 IX.7 | $C_{28}H_{28}F_2N_4O_2$ | 491 [M+H]$^+$ | 160–163 | 0.20(A) |
| 3.3 | -F | 3-F-phenyl | piperazinyl-CH₂-C(O)-N(Me)—, N'-Me | VII.5 IX.19 | $C_{29}H_{29}F_2N_5O_2$ | 518 [M+H]$^+$ | 218–220 | 0.40(A) |

-continued

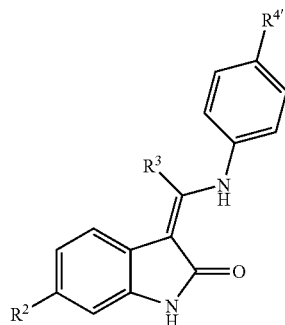

(I-3a)

| Example | $R^2$ | $R^3$ | $R^{4'}$ | Starting materials | Empirical formula | Mass spectrum | m.p. [°C.] | $R_f$ value* |
|---|---|---|---|---|---|---|---|---|
| 3.4 | -F | H₃C-C(=O)-N(H)-CH₂CH₂-C₆H₄-C(CH₃)₃ | —CH₂—NMe₂ | VII.6 IX.4 | $C_{28}H_{29}FN_4O_2$ | 471 [M−H]⁻ | 106–110 | 0.25(A) |
| 3.5 | -F | H₃C-C(=O)-N(H)-CH₂CH₂-C₆H₄-C(CH₃)₃ | —N(COMe)—(CH₂)₃—NMe₂ | VII.6 IX.7 | $C_{32}H_{36}FN_5O_3$ | 558 [M+H]⁺ | 194–196 | 0.25(A) |
| 3.6 | -F | H₃C-C(=O)-N(H)-CH₂CH₂-C₆H₄-C(CH₃)₃ | Me-N-C(=O)-CH₂-N(piperazine)N-Me (t-Bu) | VII.6 IX.19 | $C_{33}H_{37}FN_6O_3$ | 583 [M−H]⁻ | 238–240 | 0.25(A) |
| 3.7 | -F | MeO-C(=O)-CH₂-C₆H₄-C(CH₃)₃ | —CH₂—NMe₂ | VII.1 IX.4 | $C_{27}H_{26}FN_3O_3$ | 460 [M+H]⁺ | 173–176 | 0.30(A) |

-continued

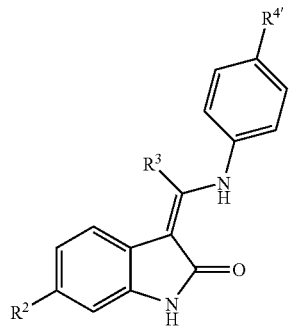

(I-3a)

| Example | R² | R³ | R⁴' | Starting materials | Empirical formula | Mass spectrum | m.p. [° C.] | R_f value* |
|---|---|---|---|---|---|---|---|---|
| 3.8 | -F | 3-iodophenyl | —CH₂—NMe₂ | VII.13 IX.4 | $C_{24}H_{21}FIN_3O$ | 514 [M+H]⁺ | 198–200 | 0.30(B) |
| 3.9 | -F | 3-(methoxycarbonylmethyl)phenyl | —CH₂—NMe₂ | VII.7 IX.4 | $C_{27}H_{26}FN_3O_3$ | 458 [M−H]⁻ | 195–198 | 0.25(A) |
| 3.10 | -F | 3-(tBuO-C(O)-NH-CH₂)phenyl | —CH₂—NMe₂ | VII.8 IX.4 | $C_{30}H_{33}FN_4O_3$ | 517 [M+H]⁺ | 230–240 | 0.30(A) |
| 3.11 | -F | 4-(methoxycarbonylmethyl)phenyl | —N(SO₂Me)— (CH₂)₂—NMe₂ | VII.1 IX.2 | $C_{29}H_{31}FN_4O_5S$ | 567 [M+H]⁺ | 188–189 | 0.40(A) |
| 3.12 | -F | 4-(methoxycarbonylmethyl)phenyl | 4-(4-methylpiperazin-1-yl)-N-methyl-N-tBu-acetamide | VII.1 IX.19 | $C_{32}H_{34}FN_5O_4$ | 572 [M+H]⁺ | 200–203 | 0.35(C) |

-continued
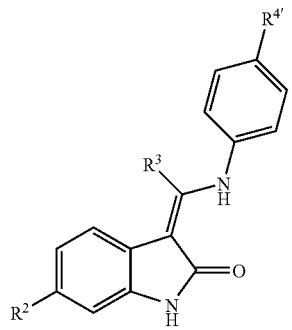
(I-3a)
| Example | R² | R³ | R⁴' | Starting materials | Empirical formula | Mass spectrum | m.p. [° C.] | R_f value* |
|---|---|---|---|---|---|---|---|---|
| 3.13 | -F | 3-(t-Bu)benzyl-CN | —CH₂—NMe₂ | VII.9 IX.4 | $C_{26}H_{23}FN_4O$ | 427 [M+H]⁺ | 130–135 | 0.25(A) |
| 3.14 | -F | 4-(t-Bu)benzyl-NHC(O)OtBu | N-Me,N-(t-Bu)-CH₂-C(O)-piperazine-N-Me | VII.10 IX.19 | $C_{35}H_{41}FN_6O_4$ | 629 [M+H]⁺ | 215–220 | 0.35(A) |
| 3.15 | -F | 4-(t-Bu)benzyl-NHC(O)OtBu | —CH₂—NMe₂ | VII.10 IX.4 | $C_{30}H_{33}FN_4O_3$ | 517 [M+H]⁺ | 186–190 | 0.35(A) |
| 3.16 | -F | 3-(t-Bu)phenethyl-NHC(O)OtBu | —CH₂—NMe₂ | VII.17 IX.4 | $C_{31}H_{35}FN_4O_3$ | 531 [M+H]⁺ | n.d | 0.40(A) |

-continued (I-3a)

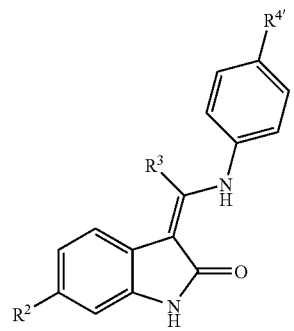

| Example | R² | R³ | R⁴' | Starting materials | Empirical formula | Mass spectrum | m.p. [° C.] | R_f value* |
|---|---|---|---|---|---|---|---|---|
| 3.17 | -F | OMe, methyl 3-(4-...)propanoate | —NMe—(COMe) | VII.15 — | C₂₈H₂₆FN₃O₄ | 488 [M+H]⁺ | 166–170 | 0.40(A) |
| 3.18 | -F | OMe, methyl 3-(4-...)propanoate | Me-N(tBu)-C(O)-CH₂-N(piperazine)-N-Me | VII.15 IX.19 | C₃₃H₃₆FN₅O₄ | 586 [M+H]⁺ | 176–180 | 0.30(A) |
| 3.19 | -F | OMe, methyl 3-(4-...)propanoate | —N(SO₂Me)— (CH₂)₂—NMe₂ | VII.15 IX.2 | C₃₀H₃₃FN₄O₅S | 581 [M+H]⁺ | 195–198 | 0.45(A) |
| 3.20 | -F | OMe, methyl 3-(4-...)propanoate | —N(COMe)— (CH₂)₃—NMe₂ | VII.15 IX.7 | C₃₂H₃₅FN₄O₄ | 559 [M+H]⁺ | 100–104 | 0.50(A) |

-continued

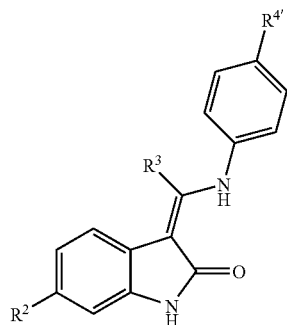

(I-3a)

| Example | $R^2$ | $R^3$ | $R^{4'}$ | Starting materials | Empirical formula | Mass spectrum | m.p. [° C.] | $R_f$ value* |
|---|---|---|---|---|---|---|---|---|
| 3.21 | -F | OMe, methyl propanoate with 4-substituted phenyl | N-Me, neopentyl, C(O)OtBu | VII.15 IX.18 | $C_{32}H_{34}FN_3O_5$ | 558 [M−H]⁻ | 132–137 | 0.80(D) |
| 3.22 | -F | OMe, methyl propanoate with 4-substituted phenyl | isobutyryl-(4-methylpiperazine) | VII.15 IX.30 | $C_{31}H_{31}FN_4O_4$ | 543 [M+H]⁺ | 234–236 | 0.60(A) |
| 3.23 | -F | OMe, methyl propanoate with 4-substituted phenyl | 1-methyl-2-(isopropyl)imidazole | VII.15 IX.16 | $C_{29}H_{25}FN_4O_3$ | 497 [M+H]⁺ | 110–115 | 0.40(A) |
| 3.24 | -F | OMe, methyl propanoate with 4-substituted phenyl | —SO₂Me | VII.15 — | $C_{26}H_{23}FN_2O_5S$ | 495 [M+H]⁺ | 130–137 | 0.60(A) |

-continued

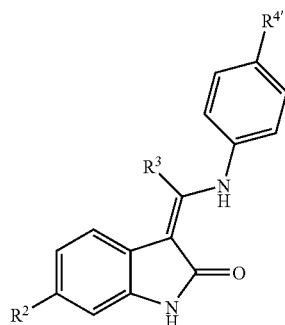

(I-3a)

| Example | R² | R³ | R⁴' | Starting materials | Empirical formula | Mass spectrum | m.p. [° C.] | $R_f$ value* |
|---|---|---|---|---|---|---|---|---|
| 3.25 | -F | methyl 3-(substituted)phenylacetate | piperazine-N-Me with CH₂C(O)N(Me)tBu | VII.7 IX.19 | $C_{32}H_{34}FN_5O_4$ | 572 [M+H]⁺ | 189 | 0.60(B) |
| 3.26 | -F | methyl 3-(substituted)phenylacetate | —N(SO₂Me)—(CH₂)₂—NMe₂ | VII.7 IX.2 | $C_{29}H_{31}FN_4O_5S$ | 567 [M+H]⁺ | n.d | 0.60(B) |
| 3.27 | -F | methyl 3-(substituted)phenylacetate | C(Me)₂-C(O)-piperazine-N-Me | VII.7 IX.30 | $C_{30}H_{29}FN_4O_4$ | 529 [M+H]⁺ | 201–203 | 0.60(B) |
| 3.28 | -F | methyl 3-(substituted)phenylacetate | —N(Me)—(CO)—CH₂—NMe₂ | VII.7 IX.10 | $C_{29}H_{29}FN_4O_4$ | 517 [M+H]⁺ | 126 | 0.60(B) |
| 3.29 | -F | methyl 3-(substituted)phenylacetate | —N(COMe)—(CH₂)₂—NMe₂ | VII.7 IX.6 | $C_{30}H_{31}FN_4O_4$ | 531 [M+H]⁺ | 179 | 0.50(B) |

-continued

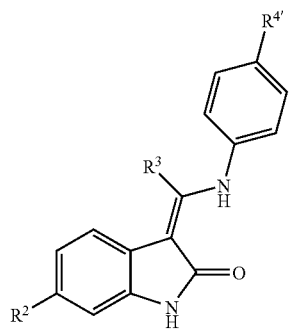

(I-3a)

| Example | R² | R³ | R⁴' | Starting materials | Empirical formula | Mass spectrum | m.p. [° C.] | R_f value* |
|---|---|---|---|---|---|---|---|---|
| 3.30 | -F | (methyl 2-(3-substituted phenyl)acetate) | —N(COMe)—(CH₂)₃—NMe₂ | VII.7 IX.7 | C₃₁H₃₃FN₄O₄ | 545 [M+H]⁺ | 123 | 0.20(B) |
| 3.31 | -F | (methyl 2-(3-substituted phenyl)acetate) | —N(Me)—(CO)—(CH₂)₄—NMe₂ | VII.7 IX.32 | C₃₂H₃₅FN₄O₄ | 559 [M+H]⁺ | 201 | 0.20(B) |
| 3.32 | -F | (methyl 2-(4-substituted phenyl)acetate) | -H | VII.1 — | C₂₄H₁₉FN₂O₃ | 403 [M+H]⁺ | 198–206 | 0.80(A) |
| 3.33 | -F | (methyl 2-(4-substituted phenyl)acetate) | (1-methyl-2-substituted imidazole) | VII.1 IX.16 | C₂₈H₂₃FN₄O₃ | 483 [M+H]⁺ | 223–226 | 0.75(A) |
| 3.34 | -F | (methyl 2-(4-substituted phenyl)acetate) | (4-methylpiperazin-1-yl)(2-substituted-2-methylpropan-1-one) | VII.1 IX.30 | C₃₀H₂₉FN₄O₄ | 529 [M+H]⁺ | 215–220 | 0.30(A) |

-continued

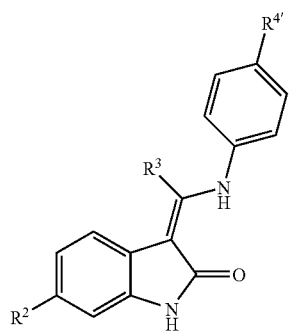
(I-3a)

| Example | R² | R³ | R⁴' | Starting materials | Empirical formula | Mass spectrum | m.p. [° C.] | $R_f$ value* |
|---|---|---|---|---|---|---|---|---|
| 3.35 | -F | ![MeO2C-CH2-C6H4-] methyl 4-substituted phenylacetate | —N(SO₂Me)—(CH₂)—(CO)—NMe₂ | VII.1 IX.8 | $C_{29}H_{29}FN_4O_6S$ | 581 [M+H]⁺ | 227–230 | 0.65(A) |
| 3.36 | -F | methyl 4-substituted phenylacetate | —N(Me)—(CO)—CH₂—NMe₂ | VII.1 IX.10 | $C_{29}H_{29}FN_4O_4$ | 517 [M+H]⁺ | 128–130 | 0.45(A) |
| 3.37 | -F | methyl 4-substituted phenylacetate | —N(COMe)—CH₃ | VII.1 — | $C_{27}H_{24}FN_3O_4$ | 474 [M+H]⁺ | 218–223 | 0.40(A) |
| 3.38 | -F | methyl 4-substituted phenylacetate | —N(Me)—(CO)—(CH₂)₂—NMe₂ | VII.1 IX.11 | $C_{30}H_{31}FN_4O_4$ | 531 [M+H]⁺ | 192–194 | 0.40(A) |
| 3.39 | -F | methyl 4-substituted phenylacetate | —SO₂Me | VII.1 — | $C_{25}H_{21}FN_2O_5S$ | 481 [M+H]⁺ | 205–214 | 0.65(A) |

-continued

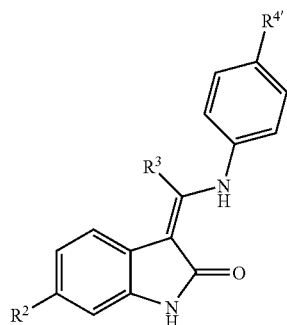

(I-3a)

| Example | R² | R³ | R⁴' | Starting materials | Empirical formula | Mass spectrum | m.p. [° C.] | $R_f$ value* |
|---|---|---|---|---|---|---|---|---|
| 3.40 | -F | (methyl 4-substituted phenylacetate) | —N(Me)—(CO)—(CH₂)₃—NMe₂ | VII.1 IX.33 | $C_{31}H_{33}FN_4O_4$ | 545 [M+H]⁺ | 190–193 | 0.15(A) |
| 3.41 | -F | (methyl 4-substituted phenylacetate) | —N(COMe)—(CH₂)₃—NMe₂ | VII.1 IX.7 | $C_{31}H_{33}FN_4O_4$ | 545 [M+H]⁺ | 184–188 | 0.50(A) |
| 3.42 | -F | (methyl 3-substituted phenylacetate) | -H | VII.7 — | $C_{24}H_{19}FN_2O_3$ | 403 [M+H]⁺ | 114 | 0.70(B) |
| 3.43 | -F | (methyl 3-substituted phenylacetate) | —SO₂Me | VII.7 — | $C_{25}H_{21}FN_2O_5S$ | 481 [M+H]⁺ | 129 | 0.60(B) |
| 3.44 | -F | (methyl 3-substituted phenylacetate) | (1-methyl-imidazol-2-yl) | VII.7 IX.16 | $C_{28}H_{23}FN_4O_3$ | 483 [M+H]⁺ | 125 | 0.60(B) |

-continued

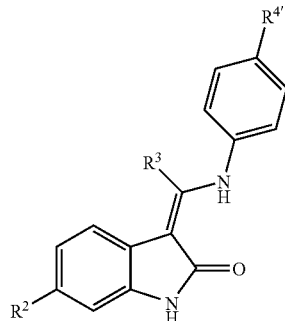

(I-3a)

| Example | R² | R³ | R⁴' | Starting materials | Empirical formula | Mass spectrum | m.p. [° C.] | $R_f$ value* |
|---|---|---|---|---|---|---|---|---|
| 3.45 | -F | methyl 3-phenylacetate (methyl ester) | —N(SO₂Me)—(CH₂)—(CO)—NMe₂ | VII.7 IX.8 | $C_{29}H_{29}FN_4O_6S$ | 581 [M+H]⁺ | 163 | 0.60(B) |
| 3.46 | -F | methyl 3-phenylacetate (methyl ester) | —N(Me)—(CO)—(CH₂)₃—NMe₂ | VII.7 IX.33 | $C_{31}H_{33}FN_4O_4$ | 545 [M+H]⁺ | 101 | 0.10(B) |
| 3.47 | -F | methyl 3-phenylacetate (methyl ester) | —N(Me)—(CO)—(CH₂)₂—NMe₂ | VII.7 IX.11 | $C_{30}H_{31}FN_4O_4$ | 531 [M+H]⁺ | 161 | 0.20(B) |
| 3.48 | -F | methyl 3-phenylpropanoate | N-methylpiperazinyl-CH₂-C(O)-N(Me)— | VII.14 IX.19 | $C_{30}H_{31}FN_4O_4$ | 586 [M+H]⁺ | 181–183 | 0.20(B) |

(I-3a)
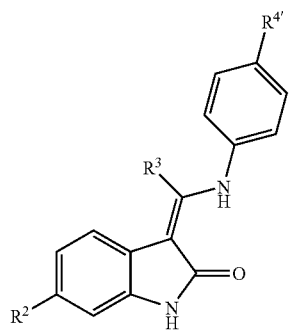
| Example | R² | R³ | R⁴' | Starting materials | Empirical formula | Mass spectrum | m.p. [° C.] | $R_f$ value* |
|---|---|---|---|---|---|---|---|---|
| 3.49 | -F | MeO-C(=O)-CH₂CH₂-C₆H₄-tBu | —N(SO₂Me)—(CH₂)₂—NMe₂ | VII.14 IX.2 | $C_{30}H_{33}FN_4O_5S$ | 581 [M+H]⁺ | 158–160 | 0.35(B) |
| 3.50 | -F | MeO-C(=O)-CH₂CH₂-C₆H₄-tBu | —N(Me)—(CO)—CH₂—NMe₂ | VII.14 IX.10 | $C_{30}H_{31}FN_4O_4$ | 531 [M+H]⁺ | n.d. | 0.40(B) |
| 3.51 | -F | MeO-C(=O)-CH₂CH₂-C₆H₄-tBu | —N(COMe)—(CH₂)₃—NMe₂ | VII.14 IX.7 | $C_{32}H_{35}FN_4O_4$ | 559 [M+H]⁺ | n.d. | 0.50(E) |
| 3.52 | -F | tBuO-C(=O)-NH-CH₂-C₆H₄-tBu | Me-N(tBu)-C(=O)-CH₂-N(piperazine)-N-Me | VII.8 IX.19 | $C_{35}H_{41}FN_6O_4$ | 629 [M+H]⁺ | n.d. | 0.35(A) |

-continued
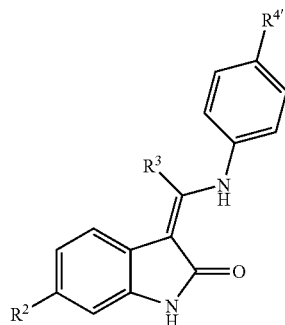
(I-3a)
| Example | R² | R³ | R⁴′ | Starting materials | Empirical formula | Mass spectrum | m.p. [°C.] | $R_f$ value* |
|---|---|---|---|---|---|---|---|---|
| 3.53 | -F | -C(O)CH₃, NH-CH₂-(3-tBu-phenyl) | —NMe—(CO)—CH₃ | VII.26 | $C_{27}H_{25}FN_4O_3$ | 473 [M+H]⁺ | 122–126 | 0.50(F) |
| 3.54 | -F | -C(O)CH₃, NH-CH₂-(3-tBu-phenyl) | —N(COMe)—(CH₂)₃—NMe₂ | VII.26 IX.7 | $C_{31}H_{34}FN_5O_3$ | 544 [M+H]⁺ | 80–83 | 0.25(A) |
| 3.55 | -F | -C(O)CH₃, NH-CH₂-(3-tBu-phenyl) | —N(SO₂Me)—(CH₂)₂—NMe₂ | VII.18 IX.2 | $C_{29}H_{32}FN_5O_4S$ | 566 [M+H]⁺ | 190–195 | 0.30(A) |
| 3.56 | -F | -C(O)CH₃, NH-CH₂-(3-tBu-phenyl) | —N(Me)—(CO)—CH₂—NMe₂ | VII.18 IX.10 | $C_{29}H_{30}FN_5O_3$ | 516 [M+H]⁺ | 238–241 | 0.30(G) |

-continued

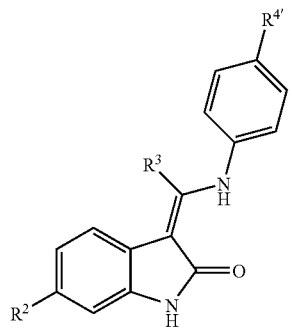

(I-3a)

| Example | $R^2$ | $R^3$ | $R^{4'}$ | Starting materials | Empirical formula | Mass spectrum | m.p. [° C.] | $R_f$ value* |
|---|---|---|---|---|---|---|---|---|
| 3.57 | -F | (methyl 3-(4-phenyl)propanoate, OMe ester) | —(CH$_2$)$_2$—NMe$_2$ | VII.15 IX.5 | $C_{29}H_{30}FN_3O_3$ | 488 [M+H]$^+$ | 205–208 | 0.55(G) |
| 3.58 | -F | (methyl 3-(4-phenyl)propanoate) | —N(Me)—(CO)—(CH$_2$)$_2$—NMe$_2$ | VII.15 IX.11 | $C_{31}H_{31}FN_4O_4$ | 543 [M−H]$^−$ | 196–202 | 0.20(A) |
| 3.59 | -F | (methyl 3-(4-phenyl)propanoate) | —N(Me)—(CO)—CH$_2$—NMe$_2$ | VII.15 IX.10 | $C_{30}H_{31}FN_4O_4$ | 531 [M+H]$^+$ | 177–182 | 0.30(A) |
| 3.60 | -F | (ethyl 3-(3-phenyl)propanoate) | —(CH$_2$)$_2$—NMe$_2$ | VII.19 IX.5 | $C_{30}H_{32}FN_3O_3$ | 500 [M−H]$^−$ | 100–105 | 0.35(B) |

-continued

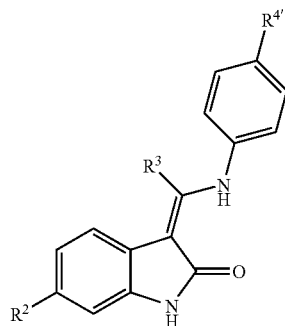

(I-3a)

| Example | $R^2$ | $R^3$ | $R^{4'}$ | Starting materials | Empirical formula | Mass spectrum | m.p. [° C.] | $R_f$ value* |
|---|---|---|---|---|---|---|---|---|
| 3.61 | -F | OMe, (structure: methyl 3-(4-tert-butylphenyl)propanoate) | —N(COMe)—(CH$_2$)$_2$—NMe$_2$ | VII.15 IX.6 | $C_{31}H_{33}FN_4O_4$ | 545 [M+H]$^+$ | 167–169 | 0.40(A) |
| 3.62 | -F | EtO, (structure: ethyl 3-(3-tert-butylphenyl)propanoate) | —N(Me)—(CO)—(CH$_2$)$_3$—NMe$_2$ | VII.19 IX.33 | $C_{33}H_{37}FN_4O_4$ | 571 [M−H]$^-$ | n.d. | 0.35(A) |
| 3.63 | -F | EtO, (structure: ethyl 3-(3-tert-butylphenyl)propanoate) | —N(Me)—(CO)—(CH$_2$)$_4$—NMe$_2$ | VII.19 IX.32 | $C_{34}H_{39}FN_4O_4$ | 585 [M−H]$^-$ | n.d. | 0.40(A) |
| 3.64 | -F | EtO, (structure: ethyl 3-(3-tert-butylphenyl)propanoate) | (2-tert-butyl-1-methylimidazol-4-yl) | VII.19 IX.16 | $C_{30}H_{27}FN_4O_3$ | 511 [M+H]$^+$ | 95–105 | 0.25(B) |

-continued
(I-3a)
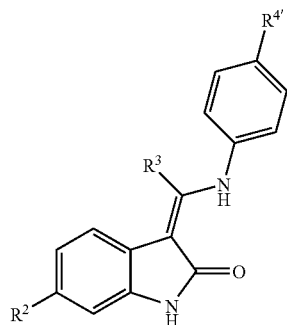
| Example | $R^2$ | $R^3$ | $R^{4'}$ | Starting materials | Empirical formula | Mass spectrum | m.p. [° C.] | $R_f$ value* |
|---|---|---|---|---|---|---|---|---|
| 3.65 | -F | OMe, methyl 3-(4-...)propanoate | —N(Me)—(CO)—(CH$_2$)$_4$—NMe$_2$ | VII.15 IX.32 | $C_{33}H_{37}FN_4O_4$ | 573 [M+H]$^+$ | 173–175 | 0.20(A) |
| 3.66 | -F | OMe, methyl 3-(4-...)propanoate | -H | VII.15 — | $C_{25}H_{21}FN_2O_3$ | 417 [M+H]$^+$ | 168–174 | 0.65(A) |
| 3.67 | -F | OMe, methyl 3-(4-...)propanoate | neopentyl-pyrrolidine | VII.15 IX.22 | $C_{30}H_{30}FN_3O_3$ | 500 [M+H]$^+$ | 168–173 | 0.40(B) |
| 3.68 | -F | OMe, methyl 3-(4-...)propanoate | —CH$_2$—NEt$_2$ | VII.15 IX.1 | $C_{30}H_{32}FN_3O_3$ | 502 [M+H]$^+$ | n.d. | 0.45(B) |

-continued
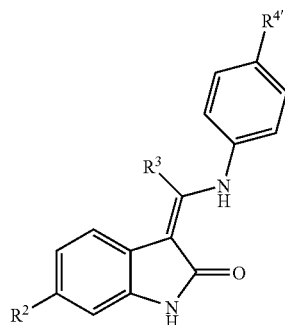
(I-3a)
| Example | R² | R³ | R⁴' | Starting materials | Empirical formula | Mass spectrum | m.p. [° C.] | $R_f$ value* |
|---|---|---|---|---|---|---|---|---|
| 3.69 | -F | (methyl 3-(4-yl)propanoate, OMe ester) | NH-C(=O)-OtBu on neopentyl | VII.15 IX.12 | $C_{31}H_{32}FN_3O_5$ | 544 [M−H]⁻ | n.d. | 0.30(G) |
| 3.70 | -F | (methyl 2-(3-yl)acetate, OMe) | —(CH₂)₂—NMe₂ | VII.7 IX.5 | $C_{28}H_{28}FN_3O_3$ | 472 [M−H]⁻ | 165–170 | 0.25(B) |
| 3.71 | -F | (methyl 2-(4-yl)acetate, OMe) | —(CH₂)₂—NMe₂ | VII.1 IX.5 | $C_{28}H_{28}FN_3O_3$ | 472 [M−H]⁻ | 193–197 | 0.25(B) |
| 3.72 | -F | (ethyl 3-(3-yl)propanoate, EtO) | —CH₂—NMe₂ | VII.19 IX.4 | $C_{29}H_{30}FN_3O_3$ | 488 [M+H]⁺ | 48–52 | 0.45(B) |

-continued
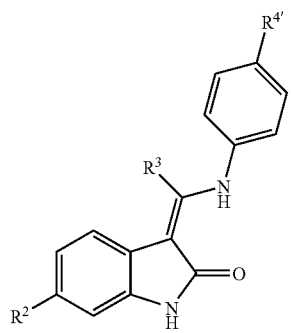
(I-3a)
| Example | R² | R³ | R⁴' | Starting materials | Empirical formula | Mass spectrum | m.p. [° C.] | $R_f$ value* |
|---|---|---|---|---|---|---|---|---|
| 3.73 | -Cl | ![OMe ester with phenyl-tBu] | —(CH₂)₂—NMe₂ | VII.20 IX.5 | $C_{29}H_{30}ClN_3O_3$ | 504/506 [M+H]⁺ | 156–160 | 0.30(H) |
| 3.74 | -Cl | ![OMe ester with phenyl-tBu] | ![2-methylimidazole] | VII.20 IX.16 | $C_{29}H_{25}ClN_4O_3$ | 513/515 [M+H]⁺ | 110 | 0.40(H) |
| 3.75 | -Cl | ![OMe ester with phenyl-tBu] | —CH₂—NMe₂ | VII.20 IX.4 | $C_{28}H_{28}ClN_3O_3$ | 490/492 [M+H]⁺ | 173–175 | 0.70(I) |
| 3.76 | -F | ![OEt ester with phenyl-tBu] | —CH₂—NMe₂ | VII.21 IX.4 | $C_{29}H_{30}FN_3O_3$ | 488 [M+H]⁺ | 158–161 | 0.35(B) |

-continued

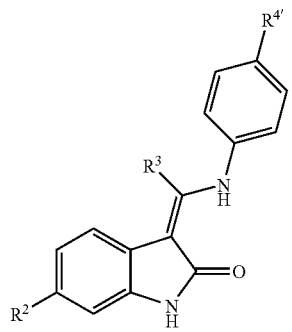

(I-3a)

| Example | R² | R³ | R⁴' | Starting materials | Empirical formula | Mass spectrum | m.p. [° C.] | R_f value* |
|---|---|---|---|---|---|---|---|---|
| 3.77 | -F | MeO-C(=O)-CH₂CH₂-(3-tBu-C₆H₄) | -CH₂-C(Me)₂-N(piperazine-N-Me) | VII.14 IX.14 | $C_{31}H_{33}FN_4O_3$ | 529 [M+H]⁺ | 147–105 | 0.50(I) |
| 3.78 | -F | MeO-C(=O)-CH₂CH₂-(3-tBu-C₆H₄) | -CH₂-C(Me)₂-(imidazol-1-yl) | VII.14 IX.15 | $C_{29}H_{25}FN_4O_3$ | 497 [M+H]⁺ | 182–185 | 0.60(K) |
| 3.79 | -F | OMe-C(=O)-CH₂CH₂-(4-tBu-C₆H₄) | -CH₂-C(Me)₂-N(piperazine-N-Me) | VII.15 IX.14 | $C_{31}H_{33}FN_4O_3$ | 529 [M+H]⁺ | 184 | 0.35(B) |
| 3.80 | -F | OMe-C(=O)-CH₂CH₂-(4-tBu-C₆H₄) | -CH₂-C(Me)₂-(imidazol-1-yl) | VII.15 IX.15 | $C_{29}H_{25}FN_4O_3$ | 497 [M+H]⁺ | 233 | 0.45(B) |

-continued

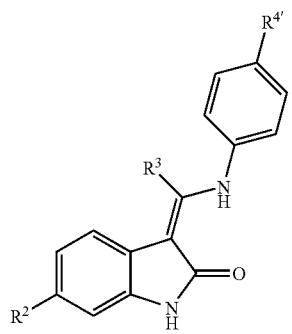

(I-3a)

| Example | $R^2$ | $R^3$ | $R^{4'}$ | Starting materials | Empirical formula | Mass spectrum | m.p. [° C.] | $R_f$ value* |
|---|---|---|---|---|---|---|---|---|
| 3.81 | -F | ![](OMe, 4-position, C(CH3)2 linker with propanoate) | —CH$_2$—NMe—(CH$_2$)$_2$—NMe$_2$ | VII.15 IX.17 | $C_{31}H_{35}FN_4O_3$ | 531 [M+H]$^+$ | 120 | 0.40(B) |
| 3.82 | -F | ![](EtO, 3-position propanoate) | —CH$_2$—NMe—(CH$_2$)$_2$—NMe$_2$ | VII.19 IX.17 | $C_{32}H_{37}FN_4O_3$ | 545 [M+H]$^+$ | n.d. | 0.40(K) |
| 3.83 | -Cl | ![](OMe, 4-position propanoate) | ![](pyrrolidinylmethyl-gem-dimethyl) | VII.20 IX.22 | $C_{30}H_{30}ClN_3O_3$ | 516/518 [M+H]$^+$ | 195–197 | 0.30(H) |
| 3.84 | -F | ![](EtO, 3-position propanoate) | -H | VII.19 — | $C_{26}H_{23}FN_2O_3$ | 431 [M+H]$^+$ | 156–160 | 0.80(M) |

-continued
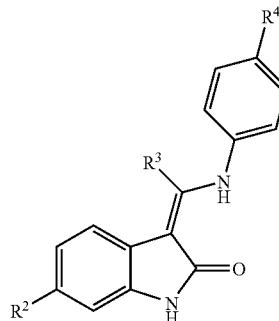
(I-3a)
| Example | R² | R³ | R⁴' | Starting materials | Empirical formula | Mass spectrum | m.p. [° C.] | R_f value* |
|---|---|---|---|---|---|---|---|---|
| 3.85 | -F | EtO-C(=O)-CH₂CH₂-(3-tBu-C₆H₄) | -CH₂-C(Me)₂-NH-C(=O)-OtBu | VII.19 IX.12 | $C_{32}H_{34}FN_3O_5$ | 560 [M+H]⁺ | n.d. | 0.50(L) |
| 3.86 | -F | EtO-C(=O)-CH₂CH₂-(3-tBu-C₆H₄) | -CH₂-C(Me)₂-N(Me)-C(=O)-OtBu | VII.19 IX.18 | $C_{33}H_{36}FN_3O_5$ | 574 [M+H]⁺ | n.d. | 0.60(L) |
| 3.87 | -F | MeO-C(=O)-CH₂-O-(3-tBu-C₆H₄) | —CH₂—NMe₂ | VII.22 IX.4 | $C_{27}H_{26}FN_3O_4$ | 476 [M+H]⁺ | 129 | 0.25(B) |

-continued
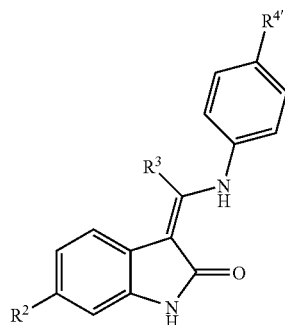
(I-3a)
| Example | R² | R³ | R⁴' | Starting materials | Empirical formula | Mass spectrum | m.p. [° C.] | R_f value* |
|---|---|---|---|---|---|---|---|---|
| 3.88 | -F | ![OMe ester phenoxy] | —CH₂—NMe₂ | VII.23 IX.4 | $C_{27}H_{26}FN_3O_4$ | 476 [M+H]⁺ | 155 | 0.25(B) |
| 3.89 | -F | ![OEt ester phenoxy] | —CH₂—NMe₂ | VII.24 IX.4 | $C_{29}H_{30}FN_3O_4$ | 504 [M+H]⁺ | n.d. | 0.20(B) |
| 3.90 | -Br | ![OMe ester phenyl] | ![pyrrolidinyl-CMe2] | VII.26 IX.22 | $C_{30}H_{30}BrN_3O_3$ | 560/562 [M+H]⁺ | 230–235 | 0.45(B) |

-continued

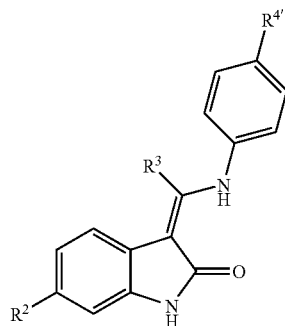

(I-3a)

| Example | R² | R³ | R⁴' | Starting materials | Empirical formula | Mass spectrum | m.p. [° C.] | R_f value* |
|---|---|---|---|---|---|---|---|---|
| 3.91 | -Br | 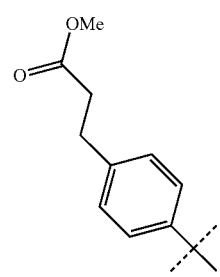 | —CH₂—NMe₂ | VII.26 IX.4 | $C_{28}H_{28}BrN_3O_3$ | 534/536 [M+H]⁺ | 178–180 | 0.35(B) |
| 3.92 | -Br | 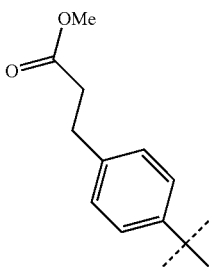 | —CH₂—NEt₂ | VII.26 IX.1 | $C_{30}H_{32}BrN_3O_3$ | 562/564 [M+H]⁺ | 173–176 | 0.40(B) |

*Eluent mixtures:
(A): silica gel, methylene chloride/methanol/ammonia 9:1:0.1
(B): silica gel, methylene chloride/methanol 9:1
(C): silica gel, methylene chloride/methanol/ammonia 8:1:0.1
(D): silica gel, methylene chloride/methanol/ammonia 10:1:0.1
(E): silica gel, methylene chloride/methanol/ammonia 5:1:0.01
(F): silica gel, ethyl acetate/methanol/ammonia = 9:1:0,1
(G): alumina, methylene chloride/methanol = 19:1
(H): silica gel, methylene chloride/methanol/ammonia 9:1:0.01
(I): silica gel, methylene chloride/methanol 5:1
(K): alumina, methylene chloride/ethanol = 20:1
(L): silica gel, petroleum ether/ethyl acetate 1:1
(M): silica gel, petroleum ether/ethyl acetate 1:2

The following compounds of the formula I-3b are prepared analogously to Example 3.0:

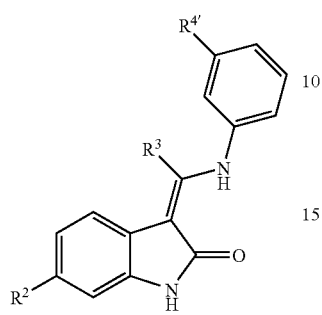
(I-3b)

| Example | R² | R³ | R⁴' | Starting materials | Empirical formula | Mass spectrum | m.p. [°C.] | R_f value* |
|---|---|---|---|---|---|---|---|---|
| 3.93 | -F | OMe, with 4-substituted phenylpropanoate ester group | —CH₂—NMe₂ | VII.15 IX.3 | $C_{28}H_{28}FN_3O_3$ | 474 [M+H]⁺ | 179–179 | 0.40(A) |
| 3.94 | -F | EtO, with 3-substituted phenylpropanoate ester group | —CH₂—NMe₂ | VII.19 IX.3 | $C_{29}H_{30}FN_3O_3$ | 486 [M−H]⁻ | n.d. | 0.45(B) |
| 3.95 | -Cl | OMe, with 4-substituted phenylpropanoate ester group | —CH₂—NMe₂ | VII.20 IX.3 | $C_{28}H_{28}ClN_3O_3$ | 490/492 [M+H]⁺ | 163–165 | 0.40(A) |

*Eluent mixtures:
(A): silica gel, methylene chloride/methanol 9:1
(B): silica gel, methylene chloride/methanol/ammonia 9:1:0.1

EXAMPLE 4.0

3-Z-[1-(4-(Dimethylaminomethyl)anilino)-1-(3,4-dimethoxyphenyl)methylene]-6-cyano-2-indolinone 130 mg of 1-acetyl-3-(1-methoxy-1-(3,4-dimethoxyphenyl)methylene)-6-cyano-2-indolinone (starting material VII.4) and 58 mg of 4-(dimethylaminomethyl)aniline (starting material IX.4) are dissolved in 5 ml of dimethylformamide and stirred at 80° C. for 2 hours. After cooling, the solvent is removed under reduced pressure and the residue is purified on a silica gel column using the mobile phase methylene chloride/methanol 9:1.

Yield: 21 mg (12% of theory),
$R_f$ value: 0.35 (silica gel, methylene chloride/methanol=9:1)
m.p. 265° C.
$C_{27}H_{26}N_4O_3$

EXAMPLE 5.0

3-Z-[1-(4-(N-Methyl-N-methylsulphonylamino)anilino)-1-(3-(2-methoxycarbonyl-vinyl)phenyl)methylene]6-chloro-2-indolinone 580 mg of 3-Z-[1-(4-(N-methyl-N-methylsulphonylamino)anilino)-1-(3-iodophenyl)-methylene]-6-chloro-2-indolinone (starting material 1.0) and 140 ml of methyl acrylate are dissolved in 20 ml of acetonitrile and 11 ml of dimethylformamide, and 11 mg of palladium(II) acetate, 2 ml of triethylamine and 30 mg of tri-ortho-tolylphosphine are added. Under nitrogen as protective gas, the solution is stirred at 90° C. for 10 hours. After cooling, the solution is filtered through Celite, the solvent is removed under reduced pressure and the residue is purified on a silica gel column using the mobile phase methylene chloride/methanol 20:1.

Yield: 450 mg (84% of theory),
$R_f$ value: 0.30 (silica gel, toluene/ethyl acetate=1:1)
m.p. 228–232° C.
$C_{27}H_{24}ClN_3O_5S$
Mass spectrum: m/z=537/539 [M]$^+$ The following compounds of the formula I-5 are prepared analogously to Example 5.0:

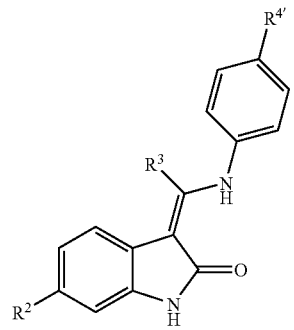

(I-5)

| Example | $R^2$ | $R^3$ | $R^{4'}$ | Starting materials | Empirical formula | Mass spectrum | m.p. [° C.] | $R_f$ value* |
|---|---|---|---|---|---|---|---|---|
| 5.1 | -Cl | 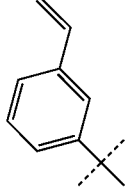 | —CH$_2$—NMe$_2$ | 1.1 | $C_{28}H_{26}ClN_3O_3$ | 486/488 [M–H]$^-$ | 150–155 | 0.50(A) |
| 5.2 | -F | 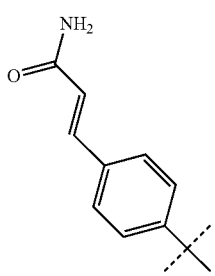 | —CH$_2$—NMe$_2$ | 3.0 | $C_{27}H_{25}FN_4O_2$ | 455 [M–H]$^-$ | 269–270 | 0.20(B) |

-continued (I-5)

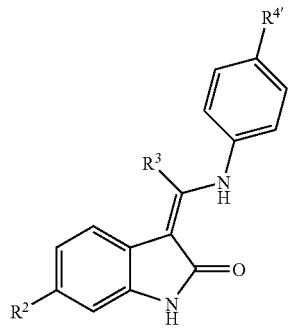

| Example | R² | R³ | R⁴' | Starting materials | Empirical formula | Mass spectrum | m.p. [° C.] | $R_f$ value* |
|---------|----|----|-----|---------------------|-------------------|---------------|-------------|--------------|
| 5.3 | -F | 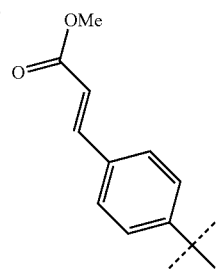 | —CH₂—NMe₂ | 3.0 | $C_{28}H_{26}FN_3O_3$ | 470 [M−H]⁻ | 205–208 | 0.65(A) |
| 5.4 | -F | 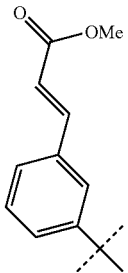 | —CH₂—NMe₂ | 1.1 | $C_{28}H_{26}FN_3O_3$ | 472 [M+H]⁺ | 138–140 | 0.45(A) |

*Eluent mixtures:
(A): silica gel, methylene chloride/methanol 5:1
(B): silica gel, methylene chloride/methanol/ammonia 9:1:0.01

EXAMPLE 6.0

3-Z-[1-(4-Dimethylaminomethylanilino)-1-(3-(2-methoxycarbonylethyl)phenyl)methylene]-6-chloro-2-indolinone 1.0 g of 3-Z-[1-(4-(dimethylaminomethyl)anilino)-1-(3-(2-methoxycarbonyl-vinyl)phenyl)methylene]-6-chloro-2-indolinone (starting material 5.1) is dissolved in 100 ml of methanol, and 200 mg of 10 percent palladium/carbon as catalyst are added. The mixture is then hydrogenated at room temperature and a hydrogen pressure of 50 psi for 6 hours. After the reaction has ended, the catalyst is filtered off, the solvent is removed under reduced pressure and the residue is dried under reduced pressure at 100° C.

Yield: 900 mg (90% of theory), $R_f$ value: 0.40 (silica gel, methylene chloride/methanol=9:1)

m.p. 160° C.

$C_{28}H_{28}ClN_3O_3$

Mass spectrum: m/z=490/492 [M+H]⁺

The following compounds of the formula I-6 are prepared analogously to Example 6.0:

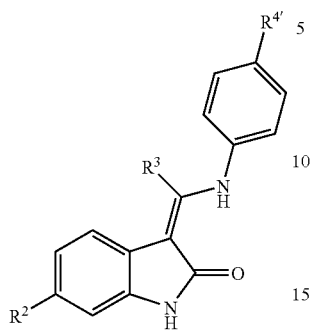

(I-6)

| Example | R² | R³ | R⁴' | Starting materials | Empirical formula | Mass spectrum | m.p. [°C.] | R_f value* |
|---|---|---|---|---|---|---|---|---|
| 6.1 | -Cl | ![methyl 3-phenylpropanoate, meta-substituted] | —N(Me)—SO₂Me | 5.0 | $C_{27}H_{26}ClN_3O_5S$ | 538/540 [M−H]⁻ | 148–150 | 0.50(A) |
| 6.2 | -F | ![3-phenylpropanamide, para-substituted] | —CH₂—NMe₂ | 5.2 | $C_{27}H_{27}FN_4O_2$ | 459 [M+H]⁺ | 150 | 0.70(B) |
| 6.3 | -F | ![methyl 3-phenylpropanoate, para-substituted] | —CH₂—NMe₂ | 5.3 | $C_{28}H_{28}FN_3O_3$ | 474 [M+H]⁺ | 140 | 0.35(A) |
| 6.4 | -F | ![methyl 3-phenylpropanoate, meta-substituted] | —CH₂—NMe₂ | 5.4 | $C_{28}H_{28}FN_3O_3$ | 474 [M+H]⁺ | 140–142 | 0.30(A) |

*Eluent mixtures:
(A): silica gel, methylene chloride/methanol 9:1
(B): silica gel, methylene chloride/methanol/ammonia 5:1:0.01

EXAMPLE 7.0

3-Z-[1-(4-Dimethylaminomethylanilino)-1-(4-aminomethylphenyl)methylene]-6-chloro-2-indolinone 900 mg of 3-Z-[1-(4-dimethylaminomethylanilino)-1-(4-cyanophenyl)methylene]-6-chloro-2-indolinone (starting material 2.0) are dissolved in 20 ml of methylene chloride and 30 ml of methanolic ammonia and, as catalyst, 200 mg of Raney nickel are added. The mixture is then hydrogenated at room temperature and a hydrogen pressure of 50 psi for 2 hours and 15 minutes. After the reaction has ended, the catalyst is filtered off, the solvent is removed under reduced pressure and the residue is washed with a little methanol and diethyl ether. To liberate the base, the residue is taken up in 1N aqueous sodium hydroxide solution and extracted four times with methylene chloride/methanol 9:1. The combined organic phases are washed with water and dried over sodium sulphate. The product is washed with a little diethyl ether and dried under reduced pressure.

Yield: 680 mg (75% of theory), $R_f$ value: 0.60 (silica gel, methylene chloride/methanol/ammonia=9:1:0.1)

m.p. 211–214° C.

$C_{25}H_{25}ClN_4O$

Mass spectrum: m/z=433/435 [M+H]$^+$

EXAMPLE 8.0

3-Z-[1-(4-(N-((4-Methylpiperazin-1-yl)methylcarbonyl)-N-methylamino)anilino)-1-(4-aminomethylphenyl)methylene]-6-chloro-2-indolinone 1.39 g of 1-acetyl-3-Z-[1-(4-(N-((4-methylpiperazin-1-yl)methylcarbonyl)-N-methylamino)anilino)-1-(4-cyanophenyl)methylene]-6-chloro-2-indolinone are dissolved in 20 ml of methylene chloride and 30 ml of methanolic ammonia and, as catalyst, 200 mg of Raney nickel are added. The mixture is then hydrogenated at room temperature at a hydrogen pressure of 50 psi for 2 hours. After the reaction has ended, the catalyst is filtered, the solvent is removed under reduced pressure and the residue is washed with a little methanol and diethyl ether. To liberate the base, the residue is taken up in 1N aqueous sodium hydroxide solution and extracted four times with methylene chloride/methanol 9:1. The combined organic phases are washed with water and dried over sodium sulphate. The product is purified on a silica gel column using, as mobile phase, a gradient of methylene chloride and methylene chloride/methanol/ammonia 8:1:0.1. The product is washed with a little diethyl ether and dried under reduced pressure.

Yield: 700 mg (54% of theory), $R_f$ value: 0.15 (silica gel, methylene chloride/methanol/ammonia=9:1:0.1)

m.p. 232–235° C.

$C_{30}H_{33}ClN_6O_2$

Mass spectrum: m/z=544/546 [M]$^+$

EXAMPLE 9.0

3-Z-[1-(4-(Dimethylaminomethyl)anilino)-1-(3-aminomethylphenyl)methylene]-6-fluoro-2-indolinone 2.72 g of 3-Z-[1-(4-(dimethylaminomethyl)anilino)-1-(3-(N-tert-butoxycarbonyl-aminomethyl)phenyl)methylene]-6-fluoro-2-indolinone (starting material 3.10) are dissolved in 50 ml of methylene chloride, and 10 ml of trifluoroacetic acid are added. The mixture is stirred at room temperature for 3 hours. After this time, most of the solvent is removed under reduced pressure and the residue is taken up in ethyl acetate and washed twice with 1N aqueous sodium hydroxide solution. The organic phase is dried over sodium sulphate, the solvent is removed using a rotary evaporator and the residue is purified on a silica gel column using the mobile phase methylene chloride/methanol/ammonia 9:1:0.1. The product is washed with a little diethyl ether and dried under reduced pressure.

Yield: 1.77 g (81% of theory), $R_f$ value: 0.25 (silica gel, methylene chloride/methanol/ammonia 9:1:0.1)

m.p. 168–175° C.

$C_{25}H_{25}FN_4O$

Mass spectrum: m/z=415 [M−H]$^−$

The following compounds of the formula I-9 are prepared analogously to Example 9.0:

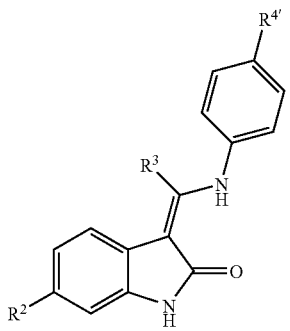

(I-9)

| Example | R² | R³ | R⁴' | Starting materials | Empirical formula | Mass spectrum | m.p. [°C.] | R_f value* |
|---|---|---|---|---|---|---|---|---|
| 9.1 | -F | 3-(tert-butyl)phenethylamine (NH₂) | —CH₂—NMe₂ | 3.16 | $C_{26}H_{27}FN_4O$ | 431 [M+H]⁺ | 155–160 | 0.45(C) |
| 9.2 | -F | 4-(tert-butyl)benzylamine (NH₂) | —CH₂—NMe₂ | 3.15 | $C_{25}H_{25}FN_4O$ | 417 [M+H]⁺ | 203–207 | 0.25(A) |
| 9.3 | -F | 4-(tert-butyl)benzylamine (NH₂) | N-methyl-N-(4-methylpiperazin-1-yl)acetamide linker | 3.14 | $C_{30}H_{33}FN_6O_2$ | 529 [M+H]⁺ | 170–175 | 0.15(A) |
| 9.4 | -F | 3-[4-(tert-butyl)phenyl]propanoic acid (OH, C=O) | —CH₂—NHMe | 10.11 | $C_{26}H_{24}FN_3O_3$ | 446 [M+H]⁺ | 245–251 | 0.20(D) |
| 9.5 | -F | N-methyl-3-[4-(tert-butyl)phenyl]propanamide (NHCH₃, C=O) | —CH₂—NHMe | 11.22 | $C_{26}H_{24}FN_3O_3$ | 459 [M+H]⁺ | 239–243 | 0.30(A) |

-continued (I-9)

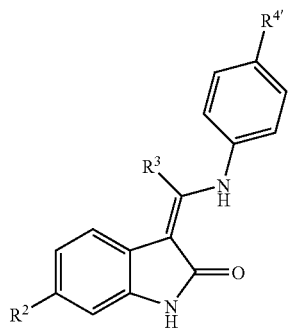

| Example | R² | R³ | R⁴' | Starting materials | Empirical formula | Mass spectrum | m.p. [° C.] | R_f value* |
|---|---|---|---|---|---|---|---|---|
| 9.6 | -F | 3-(aminomethyl)benzyl (NH₂-CH₂-C₆H₄-) | 4-(N-tBu-N-Me-carbamoylmethyl)piperazin-1-yl-CH₂- with NMe | 3.52 | C₃₀H₃₃FN₆O₂ | 529 [M+H]⁺ | n.d. | n.d. |
| 9.7 | -F | 4-(2-methoxycarbonylethyl)phenyl, OMe ester | —CH₂—NH₂ | 3.69 | C₂₆H₂₄FN₃O₃ | 444 [M−H]⁻ | 158–163 | 0.25(A) |
| 9.8 | -F | 3-(2-ethoxycarbonylethyl)phenyl, EtO ester | —CH₂—NH₂ | 3.85 | C₂₇H₂₆FN₃O₃ | 460 [M+H]⁺ | 205–210 | 0.30(B) |
| 9.9 | -F | 3-(2-ethoxycarbonylethyl)phenyl, EtO ester | —CH₂—NHMe | 3.86 | C₂₈H₂₈FN₃O₃ | 474 [M+H]⁺ | 148–150 | 0.30(B) |

*Eluent mixtures:
(A): silica gel, methylene chloride/methanol/ammonia 9:1:0.1
(B): silica gel, methylene chloride/methanol/ammonia 9:1:0.01
(C): silica gel, methylene chloride/methanol/ammonia 8:2:0.2
(D): Reversed phase RP8, methanol/sodium chloride solution(5%) = 3:2

EXAMPLE 10.0

3-Z-[1-(4-Dimethylaminomethylanilino)-1-(3-(2-carboxyethyl)phenyl)methylene]-6-chloro-2-indolinone 900 mg of 3-Z-[1-(4-dimethylaminomethylanilino)-1-(3-(2-methoxycarbonylethyl)phenyl)methylene]-6-chloro-2-indolinone (starting material 6.0) are dissolved in 10 ml of ethanol, and 5 ml of 1N aqueous sodium hydroxide solution are added. The mixture is stirred at room temperature for 5 hours. After cooling, 5 ml of 1N hydrochloric acid are added. The resulting precipitate is filtered off with suction and washed with water.

Yield: 830 mg (95% of theory),
$R_f$ value: 0.50 (reversed phase RP8, methanol/sodium chloride solution (5%)=4:1)
m.p. 210–215° C.
$C_{27}H_{26}ClN_3O_3$
Mass spectrum: m/z=476/478 [M+H]$^+$ The following compounds of the formula I-10a are prepared analogously to Example 10.0:

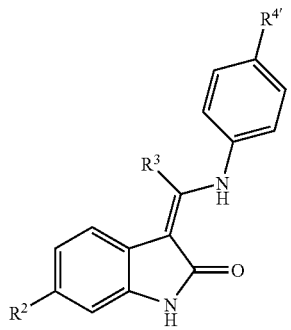

(I-10a)

| Example | R² | R³ | R⁴' | Starting materials | Empirical formula | Mass spectrum | m.p. [° C.] | $R_f$ value* |
|---|---|---|---|---|---|---|---|---|
| 10.1 | -F | (3-propanoic acid-phenyl, para) | —CH₂—NMe₂ | 6.3 | $C_{27}H_{26}FN_3O_3$ | 460 [M+H]⁺ | 250 | 0.65(A) |
| 10.2 | -F | (acetic acid-phenyl, meta) | —CH₂—NMe₂ | 3.9 | $C_{26}H_{24}FN_3O_3$ | 444 [M−H]⁻ | 278–282 | 0.10(B) |
| 10.3 | -F | (propanoic acid-phenyl, meta) | —CH₂—NMe₂ | 6.4 | $C_{27}H_{26}FN_3O_3$ | 458 [M−H]⁻ | 198–200 | 0.20(C) |

-continued

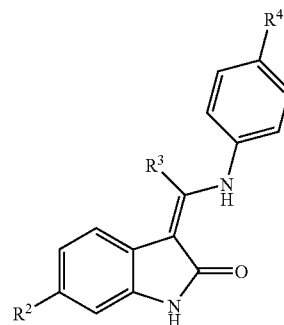

(I-10a)

| Example | $R^2$ | $R^3$ | $R^{4'}$ | Starting materials | Empirical formula | Mass spectrum | m.p. [° C.] | $R_f$ value* |
|---|---|---|---|---|---|---|---|---|
| 10.4 | -F | 4-(carboxymethyl)phenyl (CH₂COOH) | —CH₂—NMe₂ | 3.7 | $C_{26}H_{24}FN_3O_3$ | 444 [M−H]⁻ | 212–216 | 0.30(D) |
| 10.5 | -F | 4-(carboxymethyl)phenyl (CH₂COOH) | H₃C—N(—C(O)CH₂—N-piperazine-NMe) | 3.12 | $C_{31}H_{32}FN_5O_4$ | 558 [M+H]⁺ | 260–263 | 0.20(D) |
| 10.6 | -F | 4-(carboxymethyl)phenyl (CH₂COOH) | —N(SO₂Me)—(CH₂)₂—NMe₂ | 3.11 | $C_{28}H_{29}FN_4O_5S$ | 553 [M+H]⁺ | 246–249 | 0.30(D) |
| 10.7 | -F | 4-(2-carboxyethyl)phenyl (CH₂CH₂COOH) | —N(Me)—(CO)—CH₃ | 3.17 | $C_{27}H_{24}FN_3O_4$ | 474 [M+H]⁺ | 286–290 | 0.60(E) |

-continued

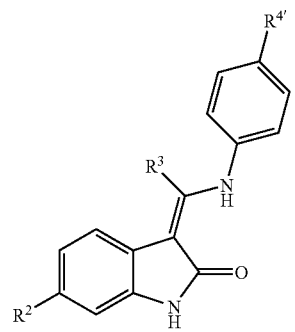

(I-10a)

| Example | R² | R³ | R⁴' | Starting materials | Empirical formula | Mass spectrum | m.p. [°C.] | $R_f$ value* |
|---|---|---|---|---|---|---|---|---|
| 10.8 | -F | ![](propanoic acid with 4-tBu-phenyl, OH) | H₃C-N(-)-C(O)-CH₂-N(piperazine)-NMe | 3.18 | $C_{32}H_{34}FN_5O_4$ | 570 [M−H]⁻ | 215–222 | 0.20(D) |
| 10.9 | -F | ![](propanoic acid with 4-tBu-phenyl, OH) | —N(SO₂Me)—(CH₂)₂—NMe₂ | 3.19 | $C_{29}H_{31}FN_4O_5S$ | 567 [M+H]⁺ | 160–165 | 0.20(D) |
| 10.10 | -F | ![](propanoic acid with 4-tBu-phenyl, OH) | —N(COMe)—(CH₂)₃—NMe₂ | 3.20 | $C_{31}H_{33}FN_4O_4$ | 545 [M+H]⁺ | 153–158 | 0.15(D) |
| 10.11 | -F | ![](propanoic acid with 4-tBu-phenyl, OH) | Me-N(-)-C(O)-OtBu | 3.21 | $C_{31}H_{32}FN_3O_5$ | 546 [M+H]⁺ | 215–219 | 0.60(E) |

-continued
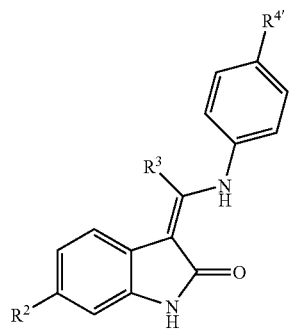
(I-10a)
| Example | R² | R³ | R⁴' | Starting materials | Empirical formula | Mass spectrum | m.p. [° C.] | R_f value* |
|---|---|---|---|---|---|---|---|---|
| 10.12 | -F | 3-(4-...phenyl)propanoic acid with OH | piperazine carbonyl with N-Me | 3.22 | $C_{30}H_{29}FN_4O_4$ | 529 [M+H]⁺ | 179–186 | 0.25(E) |
| 10.13 | -F | 3-(4-...phenyl)propanoic acid with OH | 1-Me-imidazol-2-yl | 3.23 | $C_{28}H_{23}FN_4O_3$ | 483 [M+H]⁺ | 264–267 | 0.65(E) |
| 10.14 | -F | 3-(4-...phenyl)propanoic acid with OH | —SO₂Me | 3.24 | $C_{25}H_{21}FN_2O_5S$ | 481 [M+H]⁺ | 146–155 | 0.70(E) |
| 10.15 | -F | (3-...phenyl)acetic acid with OH | piperazine carbonyl with N-Me | 3.27 | $C_{29}H_{27}FN_4O_4$ | 515 [M+H]⁺ | 251 | 0.70(E) |

-continued

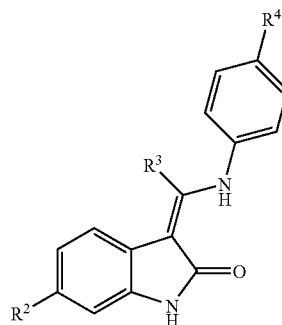

(I-10a)

| Example | $R^2$ | $R^3$ | $R^{4'}$ | Starting materials | Empirical formula | Mass spectrum | m.p. [° C.] | $R_f$ value* |
|---|---|---|---|---|---|---|---|---|
| 10.16 | -F | OH, C(=O), 3-substituted phenyl (acetic acid) | $H_3C-N(tBu)-C(=O)-CH_2-$ piperazine-NMe | 3.25 | $C_{31}H_{32}FN_5O_4$ | 558 [M+H]$^+$ | 234 | 0.10(E) |
| 10.17 | -F | OH, C(=O), 3-substituted phenyl (acetic acid) | —N(Me)—(CO)—CH$_2$—NMe$_2$ | 3.28 | $C_{28}H_{27}FN_4O_4$ | 503 [M+H]$^+$ | 203 | 0.60(E) |
| 10.18 | -F | OH, C(=O), 3-substituted phenyl (acetic acid) | —N(Me)—(CO)—(CH$_2$)$_4$—NMe$_2$ | 3.31 | $C_{31}H_{33}FN_4O_4$ | 545 [M+H]$^+$ | 251 | n.d. |
| 10.19 | -F | OH, C(=O), 3-substituted phenyl (acetic acid) | -H | 3.42 | $C_{23}H_{17}FN_2O_3$ | 387 [M−H]$^-$ | 130 | 0.60(E) |

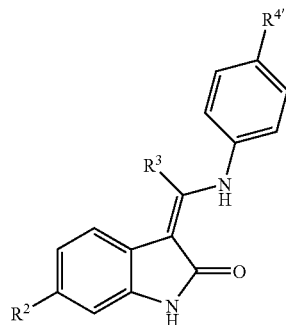

(I-10a)

| Example | R² | R³ | R⁴' | Starting materials | Empirical formula | Mass spectrum | m.p. [° C.] | $R_f$ value* |
|---|---|---|---|---|---|---|---|---|
| 10.20 | -F | OH, carboxylic acid on meta-substituted phenyl | —SO₂Me | 3.43 | $C_{24}H_{19}FN_2O_5S$ | 467 [M+H]⁺ | 139 | 0.55(E) |
| 10.21 | -F | OH, carboxylic acid on meta-substituted phenyl | N-methylimidazol-2-yl | 3.44 | $C_{27}H_{21}FN_4O_3$ | 469 [M+H]⁺ | 157 | 0.35(E) |
| 10.22 | -F | OH, carboxylic acid on meta-substituted phenyl | —N(SO₂Me)—(CH₂)—(CO)—NMe₂ | 3.45 | $C_{28}H_{27}FN_4O_6S$ | 567 [M+H]⁺ | 183 | 0.55(E) |
| 10.23 | -F | carboxylic acid on para-substituted phenyl | -H | 3.32 | $C_{23}H_{17}FN_2O_3$ | 389 [M+H]⁺ | 237–240 | 0.10(D) |

-continued

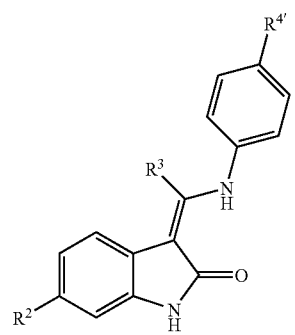
(I-10a)

| Example | R² | R³ | R⁴' | Starting materials | Empirical formula | Mass spectrum | m.p. [° C.] | R_f value* |
|---|---|---|---|---|---|---|---|---|
| 10.24 | -F | (4-carboxymethyl-phenyl) | 2-tert-butyl-1-methyl-imidazol-yl | 3.33 | C₂₇H₂₁FN₄O₃ | 469 [M+H]⁺ | 259–265 | 0.15(D) |
| 10.25 | -F | (4-carboxymethyl-phenyl) | —N(COMe)—(CH₂)₃—NMe₂ | 3.41 | C₃₀H₃₁FN₄O₄ | 531 [M+H]⁺ | 274–278 | 0.15(D) |
| 10.26 | -F | (4-carboxymethyl-phenyl) | —N(Me)—(CO)—CH₂—NMe₂ | 3.36 | C₂₈H₂₇FN₄O₄ | 503 [M+H]⁺ | 258–264 | 0.20(D) |
| 10.27 | -F | (4-carboxymethyl-phenyl) | 2-methyl-2-(4-methylpiperazin-1-yl-carbonyl) | 3.34 | C₂₉H₂₇FN₄O₄ | 515 [M+H]⁺ | 279–282 | 0.15(D) |
| 10.28 | -F | (4-carboxymethyl-phenyl) | —SO₂Me | 3.39 | C₂₄H₁₉FN₂O₅S | 467 [M+H]⁺ | 260–266 | 0.35(F) |

-continued
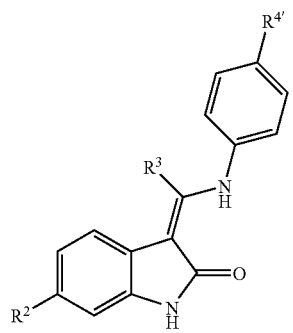
(I-10a)
| Example | R² | R³ | R⁴' | Starting materials | Empirical formula | Mass spectrum | m.p. [° C.] | $R_f$ value* |
|---|---|---|---|---|---|---|---|---|
| 10.29 | -F | (4-CH₂COOH-phenyl) | —N(COMe)—CH₃ | 3.37 | $C_{26}H_{22}FN_3O_4$ | 460 [M+H]⁺ | 290–294 | 0.30(F) |
| 10.30 | -F | (4-CH₂COOH-phenyl) | —N(SO₂Me)—CH₂—(CO)—NMe₂ | 3.35 | $C_{28}H_{27}FN_4O_6S$ | 567 [M+H]⁺ | 238–242 | 0.30(F) |
| 10.31 | -F | (4-CH₂COOH-phenyl) | —N(Me)—(CO)—(CH₂)₂—NMe₂ | 3.38 | $C_{29}H_{29}FN_4O_4$ | 517 [M+H]⁺ | 250–255 | 0.35(F) |
| 10.32 | -F | (4-CH₂COOH-phenyl) | —N(Me)—(CO)—(CH₂)₃—NMe₂ | 3.40 | $C_{30}H_{31}FN_4O_4$ | 531 [M+H]⁺ | 184–190 | 0.25(F) |
| 10.33 | -F | (3-CH₂CH₂COOH-phenyl) | —N(Me)—C(O)—CH₂—N(piperazinyl-NMe) | 3.48 | $C_{32}H_{34}FN_5O_4$ | 572 [M−H]⁻ | 170–175 | 0.40(C) |

-continued
(I-10a)
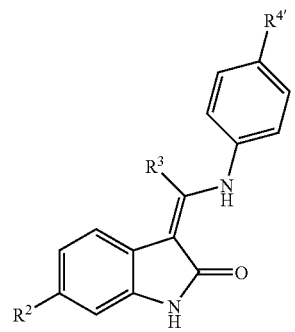
| Example | R² | R³ | R⁴' | Starting materials | Empirical formula | Mass spectrum | m.p. [° C.] | R_f value* |
|---|---|---|---|---|---|---|---|---|
| 10.34 | -F | (3-tert-butylphenyl)CH₂-C(=O)-OH | —N(SO₂Me)—(CH₂)₂—NMe₂ | 3.26 | $C_{28}H_{29}FN_4O_5S$ | 553 [M+H]⁺ | 180 | 0.60(C) |
| 10.35 | -F | (3-tert-butylphenyl)(CH₂)₂-C(=O)-OH | —N(SO₂Me)—(CH₂)₂—NMe₂ | 3.49 | $C_{29}H_{31}FN_4O_5S$ | 567 [M+H]⁺ | 196–199 | 0.30(C) |
| 10.36 | -F | (3-tert-butylphenyl)(CH₂)₂-C(=O)-OH | —N(Me)—(CO)—CH₂—NMe₂ | 3.50 | $C_{29}H_{29}FN_4O_4$ | 517 [M+H]⁺ | 150 | 0.20(C) |
| 10.37 | -F | (3-tert-butylphenyl)(CH₂)₂-C(=O)-OH | —N(COMe)—(CH₂)₃—NMe₂ | 3.51 | $C_{31}H_{33}FN_4O_4$ | 545 [M+H]⁺ | 206–210 | 0.30(A) |

-continued
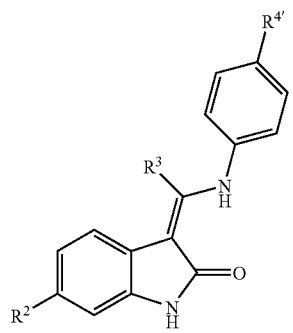
(I-10a)
| Example | R² | R³ | R⁴' | Starting materials | Empirical formula | Mass spectrum | m.p. [° C.] | $R_f$ value* |
|---|---|---|---|---|---|---|---|---|
| 10.38 | -F | 3-(4-carboxyethyl-phenyl)-propyl (OH, C=O) | —N(Me)—(CO)—CH₂—NMe₂ | 3.59 | $C_{29}H_{29}FN_4O_4$ | 517 [M+H]⁺ | 231–236 | 0.60(A) |
| 10.39 | -F | 3-(4-carboxyethyl-phenyl)-propyl (OH, C=O) | —(CH₂)₂—NMe₂ | 3.57 | $C_{28}H_{28}FN_3O_3$ | 474 [M+H]⁺ | 218–222 | 0.50(A) |
| 10.40 | -F | 3-(4-carboxyethyl-phenyl)-propyl (OH, C=O) | —N(Me)—(CO)—(CH₂)₂—NMe₂ | 3.58 | $C_{30}H_{31}FN_4O_4$ | 531 [M+H]⁺ | 215–218 | 0.50(A) |
| 10.41 | -F | 3-(3-carboxyethyl-phenyl)-propyl (O, OH) | —(CH₂)₂—NMe₂ | 3.60 | $C_{28}H_{28}FN_3O_3$ | 474 [M+H]⁺ | 172–177 | 0.15(G) |

-continued

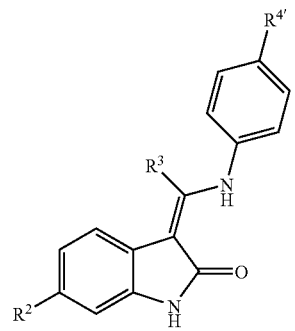
(I-10a)

| Example | $R^2$ | $R^3$ | $R^{4'}$ | Starting materials | Empirical formula | Mass spectrum | m.p. [° C.] | $R_f$ value* |
|---|---|---|---|---|---|---|---|---|
| 10.42 | -F | 3-(4-tert-butylphenyl)propanoic acid | —N(COMe)—(CH$_2$)$_2$—NMe$_2$ | 3.61 | $C_{30}H_{31}FN_4O_4$ | 531 [M+H]$^+$ | 230–234 | 0.50(A) |
| 10.43 | -F | 3-(3-tert-butylphenyl)propanoic acid | —N(Me)—(CO)—(CH$_2$)$_3$—NMe$_2$ | 3.62 | $C_{31}H_{33}FN_4O_4$ | 545 [M+H]$^+$ | 170–175 | 0.30(E) |
| 10.44 | -F | 3-(3-tert-butylphenyl)propanoic acid | —N(Me)—(CO)—(CH$_2$)$_4$—NMe$_2$ | 3.63 | $C_{32}H_{35}FN_4O_4$ | 559 [M+H]$^+$ | 142–146 | 0.10(G) |
| 10.45 | -F | 3-(3-tert-butylphenyl)propanoic acid | 2-tert-butyl-1-methylimidazole | 3.64 | $C_{28}H_{23}FN_4O_3$ | 483 [M+H]$^+$ | 262–269 | 0.20(E) |

-continued
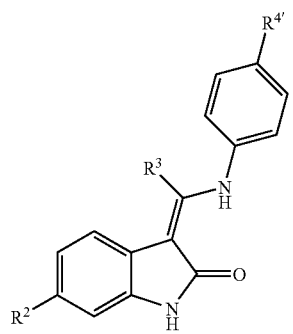
(I-10a)
| Example | R² | R³ | R⁴' | Starting materials | Empirical formula | Mass spectrum | m.p. [° C.] | R_f value* |
|---------|----|----|----|-----|---------|---------|------|------|
| 10.46 | -F | 3-(4-carboxyethyl-phenyl), OH | —N(Me)—(CO)—(CH₂)₄—NMe₂ | 3.65 | $C_{32}H_{35}FN_4O_4$ | 559 [M+H]⁺ | 234–236 | 0.30(A) |
| 10.47 | -F | 3-(4-carboxyethyl-phenyl), OH | -H | 3.66 | $C_{24}H_{19}FN_2O_3$ | 403 [M+H]⁺ | 231–233 | 0.20(A) |
| 10.48 | -F | 3-(4-carboxyethyl-phenyl), OH | pyrrolidinylmethyl | 3.67 | $C_{29}H_{28}FN_3O_3$ | 486 [M+H]⁺ | 205–210 | 0.10(E) |
| 10.49 | -F | 3-(4-carboxyethyl-phenyl), OH | —CH₂—NEt₂ | 3.68 | $C_{29}H_{30}FN_3O_3$ | 488 [M+H]⁺ | 145–150 | 0.15(E) |

-continued
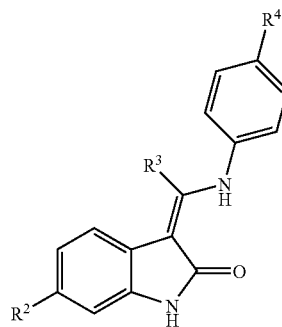
(I-10a)
| Example | $R^2$ | $R^3$ | $R^{4'}$ | Starting materials | Empirical formula | Mass spectrum | m.p. [° C.] | $R_f$ value* |
|---|---|---|---|---|---|---|---|---|
| 10.50 | -F | 3-(4-carboxyethylphenyl) with OH/C=O | —CH$_2$—NH$_2$ | 9.7 | $C_{25}H_{22}FN_3O_3$ | 430 [M−H]$^-$ | 280–285 | 0.05(H) |
| 10.51 | -F | 3-(carboxymethylphenyl) meta | —(CH$_2$)$_2$—NMe$_2$ | 3.70 | $C_{27}H_{26}FN_3O_3$ | 460 [M+H]$^+$ | 273–276 | 0.15(E) |
| 10.52 | -F | 4-(carboxymethylphenyl) para | —(CH$_2$)$_2$—NMe$_2$ | 3.71 | $C_{27}H_{26}FN_3O_3$ | 460 [M+H]$^+$ | 230–235 | 0.05(E) |
| 10.53 | -Cl | 4-(carboxyethylphenyl) | —(CH$_2$)$_2$—NMe$_2$ | 3.73 | $C_{28}H_{28}ClN_3O_3$ | 490/492 [M+H]$^+$ | 255–258 | 0.50(A) |

-continued

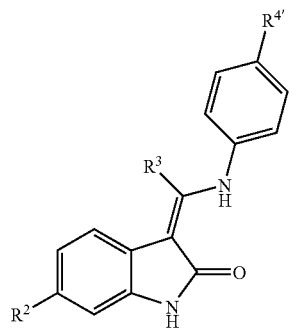
(I-10a)

| Example | $R^2$ | $R^3$ | $R^{4'}$ | Starting materials | Empirical formula | Mass spectrum | m.p. [° C.] | $R_f$ value* |
|---|---|---|---|---|---|---|---|---|
| 10.54 | -Cl | 3-(4-tert-butylphenyl)propanoic acid OH | 2-tert-butyl-1-methylimidazole | 3.74 | $C_{28}H_{23}ClN_4O_3$ | 499/501 $[M+H]^+$ | 296–300 | 0.50(A) |
| 10.55 | -Cl | 3-(4-tert-butylphenyl)propanoic acid OH | —$CH_2$—$NMe_2$ | 3.75 | $C_{27}H_{26}ClN_3O_3$ | 476/478 $[M+H]^+$ | 228–230 | 0.50(A) |
| 10.56 | -F | 3-(3-tert-butylphenyl)propanoic acid OH | 4-methylpiperazinylmethyl | 3.77 | $C_{30}H_{31}FN_4O_3$ | 515 $[M+H]^+$ | 210–215 | 0.40(A) |
| 10.57 | -F | 3-(3-tert-butylphenyl)propanoic acid OH | imidazol-1-ylmethyl | 3.78 | $C_{28}H_{23}FN_4O_3$ | 483 $[M+H]^+$ | 240–245 | 0.50(A) |

-continued

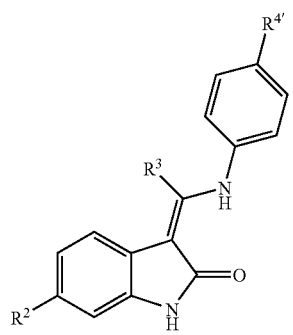

(I-10a)

| Example | R² | R³ | R⁴' | Starting materials | Empirical formula | Mass spectrum | m.p. [° C.] | $R_f$ value* |
|---|---|---|---|---|---|---|---|---|
| 10.58 | -F | 3-(tert-butyl)phenyl-CH₂CH₂-C(=O)OH | —CH₂NMe—(CH₂)₂—NMe₂ | 3.82 | $C_{30}H_{33}FN_4O_3$ | 517 [M+H]⁺ | n.d. | 0.30(I) |
| 10.59 | -F | 4-(tert-butyl)phenyl-CH₂CH₂-C(=O)OH | 4-methylpiperazinyl-CH₂- | 3.79 | $C_{30}H_{31}FN_4O_3$ | 515 [M+H]⁺ | 275 | 0.35(A) |
| 10.60 | -F | 4-(tert-butyl)phenyl-CH₂CH₂-C(=O)OH | imidazol-1-yl-CH₂- | 3.80 | $C_{28}H_{23}FN_4O_3$ | 483 [M+H]⁺ | 280 | 0.55(A) |
| 10.61 | -F | 4-(tert-butyl)phenyl-CH₂CH₂-C(=O)OH | pyrrolidin-1-yl-CH₂- | 3.83 | $C_{29}H_{28}ClN_3O_3$ | 502/504 [M+H]⁺ | 260–266 | 0.50(A) |

-continued

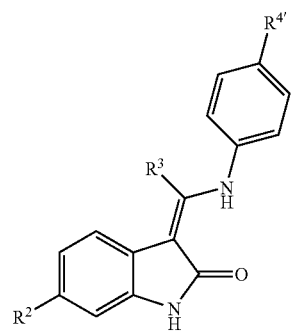
(I-10a)

| Example | $R^2$ | $R^3$ | $R^{4'}$ | Starting materials | Empirical formula | Mass spectrum | m.p. [° C.] | $R_f$ value* |
|---|---|---|---|---|---|---|---|---|
| 10.62 | -F | OH, O, phenyl with t-Bu (para) propanoic acid | —CH$_2$NMe—(CH$_2$)$_2$—NMe$_2$ | 3.81 | C$_{30}$H$_{33}$FN$_4$O$_3$ | 517 [M+H]$^+$ | n.d. | 0.05(E) |
| 10.63 | -F | HO, O, phenyl with t-Bu (meta) propanoic acid | -H | 3.84 | C$_{24}$H$_{19}$FN$_2$O$_3$ | 403 [M+H]$^+$ | 110–112 | 0.60(K) |
| 10.64 | -F | HO, O, phenyl with t-Bu (meta) propanoic acid | —CH$_2$—NH$_2$ | 9.8 | C$_{25}$H$_{22}$FN$_3$O$_3$ | 432 [M+H]$^+$ | 260–263 | 0.60(A) |
| 10.65 | -F | HO, O, phenyl with t-Bu (meta) propanoic acid | —CH$_2$—NHMe | 9.9 | C$_{26}$H$_{24}$FN$_3$O$_3$ | 446 [M+H]$^+$ | 265–270 | 0.60(A) |

-continued
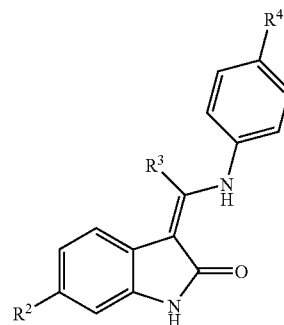
(I-10a)
| Example | $R^2$ | $R^3$ | $R^{4'}$ | Starting materials | Empirical formula | Mass spectrum | m.p. [° C.] | $R_f$ value* |
|---|---|---|---|---|---|---|---|---|
| 10.66 | -F | (3-tert-butylphenoxy)acetic acid | —CH$_2$—NMe$_2$ | 3.87 | C$_{26}$H$_{24}$FN$_3$O$_4$ | 462 [M+H]$^+$ | 250 | 0.10(M) |
| 10.67 | -F | (4-tert-butylphenoxy)acetic acid | —CH$_2$—NMe$_2$ | 3.88 | C$_{26}$H$_{24}$FN$_3$O$_4$ | 462 [M+H]$^+$ | 247 | 0.15(M) |
| 10.68 | -Br | 3-(4-tert-butylphenyl)propanoic acid | pyrrolidinylmethyl (neopentyl) | 3.90 | C$_{29}$H$_{28}$BrN$_3$O$_3$ | 546/548 [M+H]$^+$ | 290–293 | 0.30(E) |

-continued

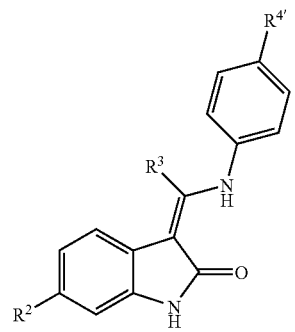

(I-10a)

| Example | $R^2$ | $R^3$ | $R^{4'}$ | Starting materials | Empirical formula | Mass spectrum | m.p. [° C.] | $R_f$ value* |
|---|---|---|---|---|---|---|---|---|
| 10.69 | -Br | (3-(4-substituted phenyl)propanoic acid) | —CH$_2$—NMe$_2$ | 3.91 | C$_{27}$H$_{26}$BrN$_3$O$_3$ | 520/522 [M+H]$^+$ | 243–246 | 0.25(E) |
| 10.70 | -Br | (3-(4-substituted phenyl)propanoic acid) | —CH$_2$—NEt$_2$ | 3.92 | C$_{29}$H$_{30}$BrN$_3$O$_3$ | 548/550 [M+H]$^+$ | 252–255 | 0.35(E) |

*Eluent mixtures:
(A): reversed phase RP8, methanol/sodium chloride solution (5%) = 4:1
(B): silica gel, methylene chloride/methanol = 8:2
(C): silica gel, methylene chloride/methanol = 5:1
(D): reversed phase RP8, methanol/sodium chloride solution (5%) = 3:2
(E): silica gel, methylene chloride/methanol = 9:1
(F): reversed phase RP8, methanol/sodium chloride solution (5%) = 7:3
(G): silica gel, methylene chloride/methanol/ammonia = 9:1:0.1
(H): alumina, methylene chloride/methanol = 19:1
(I): reversed phase RP8, methanol/sodium chloride solution (5%) = 4:2
(K): silica gel, petroleum ether/ethyl acetate = 1:1
(M): silica gel, methylene chloride/methanol = 4:1

The following compounds of the formula I-10b are prepared analogously to Example 10.0:

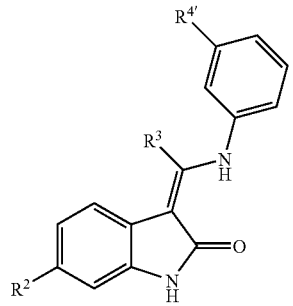

(I-10b)

| Example | R² | R³ | R⁴' | Starting materials | Empirical formula | Mass spectrum | m.p. [° C.] | R_f-value* |
|---------|-----|--------|-------------|------|--------------------------------|-----------------|---------|----------|
| 10.71 | —F | (3-carboxyethyl-4-substituted phenyl, para) OH | —CH₂—NMe₂ | 3.93 | $C_{27}H_{26}FN_3O_3$ | 460 [M + H]⁺ | 150 | 0.20 (A) |
| 10.72 | —F | (3-carboxyethyl-meta substituted phenyl) OH | —CH₂—NMe₂ | 3.94 | $C_{27}H_{26}FN_3O_3$ | 460 [M + H]⁺ | 105–109 | 0.30 (B) |
| 10.73 | —Cl | (3-carboxyethyl-para substituted phenyl) OH | —CH₂—NMe₂ | 3.95 | $C_{27}H_{26}ClN_3O_3$ | 476/478 [M + H]⁺ | 230–235 | 0.50 (C) |

*Eluent mixtures:
(A): silica gel, methylene chloride/methanol = 5:1
(B): silica gel, methylene chloride/methanol = 9:1
(C): reversed phase RP8, methanol/sodium chloride solution (5%) = 4:1

EXAMPLE 11.0

3-Z-[1-(4-Dimethylaminomethylanilino)-1-(3-(2-carbamoylethyl)phenyl)methylene]-6-chloro-2-indolinone 480 mg of 3-Z-[1-(4-dimethylaminomethylanilino)-1-(3-(2-carboxyethyl)phenyl)methylene]-6-chloro-2-indolinone (starting material 10.0), 350 mg of TBTU, 150 mg of HOBt and 420 ml of triethylamine are dissolved in 10 ml of dimethylformamide, and 620 mg of N-hydroxysuccinimide ammonium salt are added. The mixture is stirred at room temperature for 20 hours. After removal of the solvent under reduced pressure, the residue is suspended in a little ethyl acetate and water, filtered off and washed with water. The residue is purified on an alumina column (activity 2-3) using the mobile phase methylene chloride/ethanol 20:1. The product is recrystallized from diethyl ether and dried under reduced pressure at 100° C.

Yield: 370 mg (78% of theory), $R_f$ value: 0.40 (alumina, methylene chloride/ethanol=20:1)

m.p. 222–225° C.

$C_{27}H_{27}ClN_4O_2$

Mass spectrum: m/z=475/477 $[M+H]^+$

The following compounds of the formula I-11 are prepared analogously to Example 11.0:

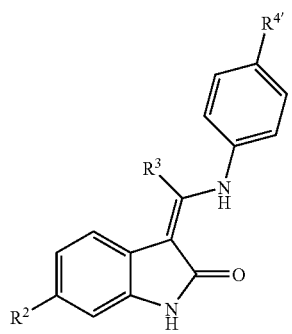

(I-11)

| Example | $R^2$ | $R^3$ | $R^{4'}$ | Starting materials | Empirical formula | Mass spectrum | m.p. [° C.] | $R_f$ value* |
|---------|-------|-------|----------|--------------------|--------------------|---------------|-------------|--------------|
| 11.1 | —Cl | 3-(tBu)C₆H₄CH₂CH₂C(O)NHCH₃ | —CH₂—NMe₂ | 10.0** | $C_{28}H_{29}ClN_4O_2$ | 489/491 $[M + H]^+$ | 223–225 | 0.50 (A) |
| 11.2 | —F | 4-(tBu)C₆H₄CH₂CH₂C(O)NHCH₃ | —CH₂—NMe₂ | 10.1** | $C_{28}H_{29}FN_4O_2$ | 473 $[M + H]^+$ | 148–150 | 0.40 (B) |
| 11.3 | —F | 3-(tBu)C₆H₄CH₂C(O)NMe₂ | —CH₂—NMe₂ | 10.2*** | $C_{28}H_{29}FN_4O_2$ | 473 $[M + H]^+$ | 98–103 | 0.30 (C) |

-continued
(I-11)
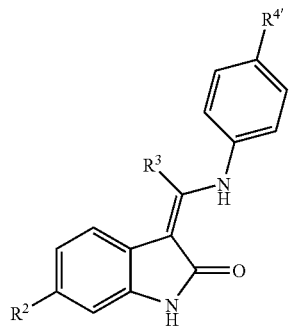
| Example | R² | R³ | R⁴' | Starting materials | Empirical formula | Mass spectrum | m.p. [° C.] | R_f value* |
|---|---|---|---|---|---|---|---|---|
| 11.4 | —F | (3-tBu-C₆H₄)CH₂CH₂C(O)NH₂ | —CH₂—NMe₂ | 10.3 | C₂₇H₂₇FN₄O₂ | 459 [M + H]⁺ | 223–225 | 0.50 (A) |
| 11.5 | —F | (3-tBu-C₆H₄)CH₂CH₂C(O)NHMe | —CH₂—NMe₂ | 10.3** | C₂₈H₂₉FN₄O₂ | 473 [M + H]⁺ | 210–213 | 0.70 (A) |
| 11.6 | —F | (3-tBu-C₆H₄)CH₂CH₂C(O)NMe₂ | —CH₂—NMe₂ | 10.3*** | C₂₉H₃₁FN₄O₂ | 487 [M + H]⁺ | 213–215 | 0.80 (A) |
| 11.7 | —F | (3-tBu-C₆H₄)CH₂C(O)NH₂ | —CH₂—NMe₂ | 10.2 | C₂₆H₂₅FN₄O₂ | 443 [M − H]⁻ | 115–120 | 0.25 (C) |

-continued
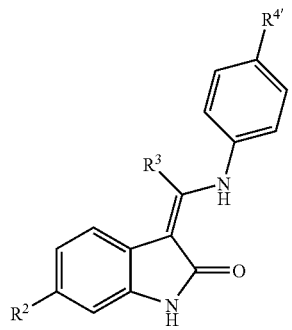
(I-11)
| Example | R² | R³ | R⁴' | Starting materials | Empirical formula | Mass spectrum | m.p. [° C.] | R_f value* |
|---|---|---|---|---|---|---|---|---|
| 11.8 | —F | NHMe-C(=O)-CH₂-(3-tBu-phenyl)- | —CH₂—NMe₂ | 10.2** | C₂₇H₂₇FN₄O₂ | 457 [M − H]⁻ | 222–225 | 0.25 (C) |
| 11.9 | —F | NH₂-C(=O)-CH₂-(4-tBu-phenyl)- | —CH₂—NMe₂ | 10.4 | C₂₆H₂₅FN₄O₂ | 443 [M − H]⁻ | 143–146 | 0.40 (D) |
| 11.10 | —F | NMe₂-C(=O)-CH₂CH₂-(4-tBu-phenyl)- | —CH₂—NMe₂ | 10.1*** | C₂₉H₃₁FN₄O₂ | 487 [M + H]⁺ | 198–200 | 0.60 (B) |
| 11.11 | —F | (4-Me-piperazin-1-yl)-C(=O)-CH₂CH₂-(4-tBu-phenyl)- | —CH₂—NMe₂ | 10.1**** | C₃₂H₃₆FN₅O₂ | 542 [M + H]⁺ | 175 | 0.60 (B) |

-continued
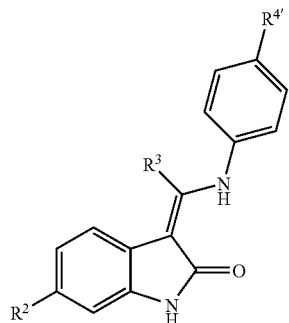
(I-11)
| Example | R² | R³ | R⁴' | Starting materials | Empirical formula | Mass spectrum | m.p. [° C.] | R_f value* |
|---|---|---|---|---|---|---|---|---|
| 11.12 | —F | NH₂-phenyl) | -CH₂-N-piperazine-NMe) | 10.5 | $C_{31}H_{33}FN_6O_3$ | 557 [M + H]⁺ | 150–156 | 0.40 (E) |
| 11.13 | —F | NH₂-phenyl) | —N(SO₂Me)—(CH₂)₂—NMe₂ | 10.6 | $C_{28}H_{30}FN_5O_4S$ | 552 [M + H]⁺ | 197–199 | 0.50 (D) |
| 11.14 | —F | NMe₂-phenyl) | —CH₂—NMe₂ | 10.4*** | $C_{28}H_{29}FN_4O_2$ | 473 [M + H]⁺ | 147–152 | 0.35 (D) |
| 11.15 | —F | NHMe-phenyl) | —CH₂—NMe₂ | 10.4** | $C_{27}H_{27}FN_4O_2$ | 459 [M + H]⁺ | 208–214 | 0.35 (D) |

-continued
(I-11)
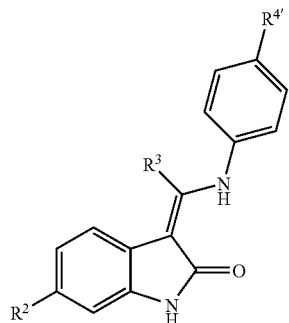
| Example | R² | R³ | R⁴' | Starting materials | Empirical formula | Mass spectrum | m.p. [° C.] | R_f value* |
|---------|----|----|-----|--------------------|-------------------|---------------|-------------|------------|
| 11.16 | —F | 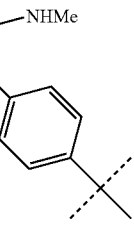 | —N(SO₂Me)—(CH₂)₂—NMe₂ | 10.6** | C₂₉H₃₂FN₅O₄S | 566 [M + H]⁺ | 218–222 | 0.70 (F) |
| 11.17 | —F | 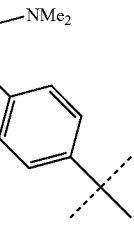 | —N(SO₂Me)—(CH₂)₂—NMe₂ | 10.6*** | C₃₀H₃₄FN₅O₄S | 580 [M + H]⁺ | 199–205 | 0.40 (C) |
| 11.18 | —F | 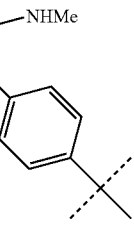 | 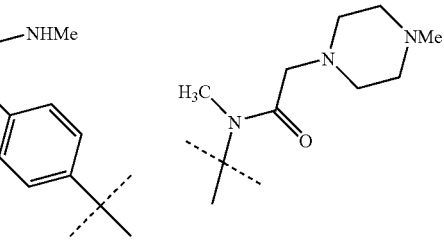 | 10.5** | C₃₂H₃₅FN₆O₃ | 571 [M + H]⁺ | 155–160 | 0.20 (C) |
| 11.19 | —F | 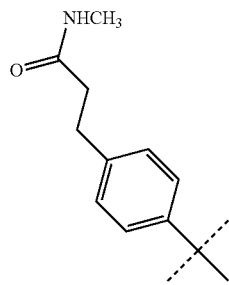 | —N(Me)—(CO)—CH₃ | 10.7** | C₂₈H₂₇FN₄O₃ | 487 [M + H]⁺ | 137–145 | 0.50 (C) |

-continued
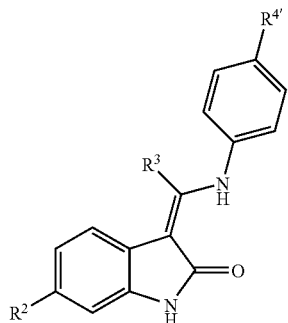
(I-11)
| Example | R² | R³ | R⁴' | Starting materials | Empirical formula | Mass spectrum | m.p. [° C.] | R_f value* |
|---|---|---|---|---|---|---|---|---|
| 11.20 | —F | 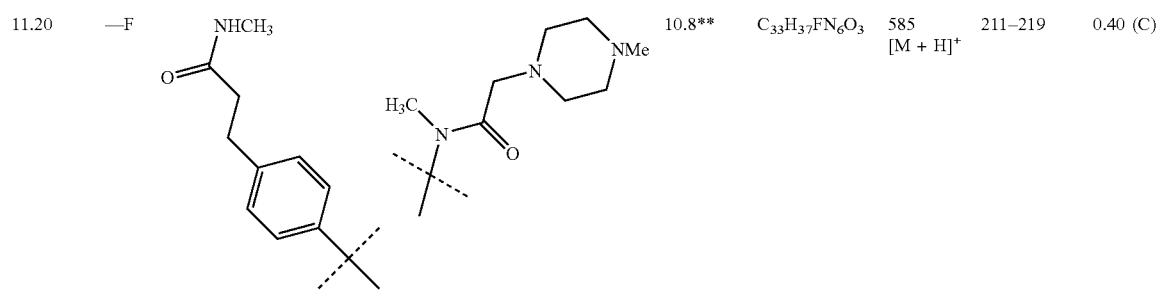 | | 10.8** | C₃₃H₃₇FN₆O₃ | 585 [M + H]⁺ | 211–219 | 0.40 (C) |
| 11.21 | —F | 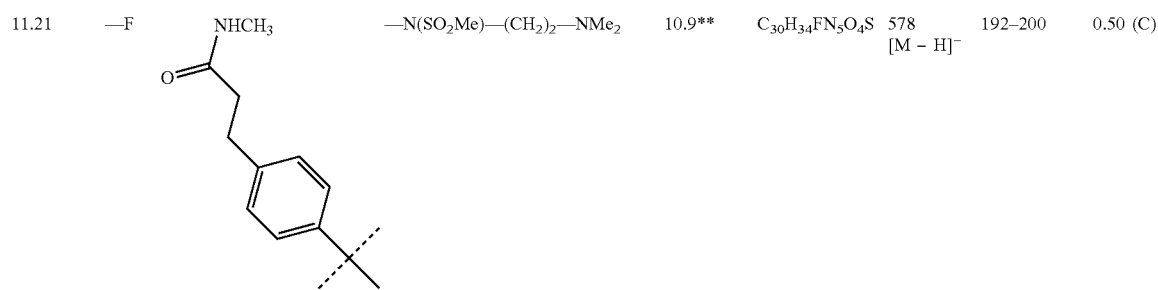 | —N(SO₂Me)—(CH₂)₂—NMe₂ | 10.9** | C₃₀H₃₄FN₅O₄S | 578 [M − H]⁻ | 192–200 | 0.50 (C) |
| 11.22 | —F | 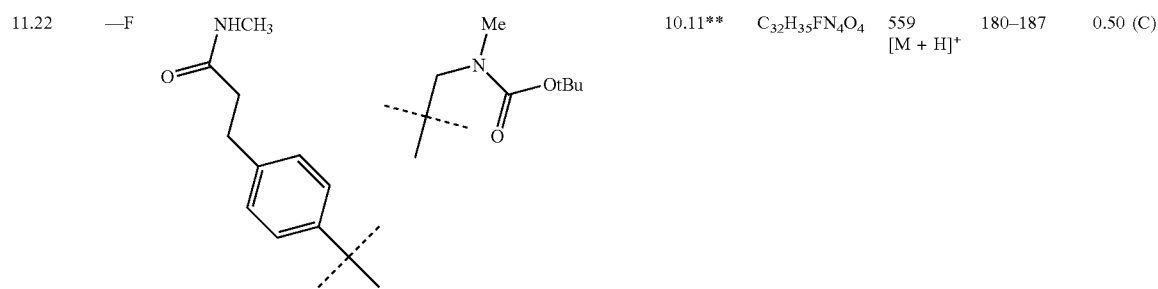 | | 10.11** | C₃₂H₃₅FN₄O₄ | 559 [M + H]⁺ | 180–187 | 0.50 (C) |

-continued
(I-11)
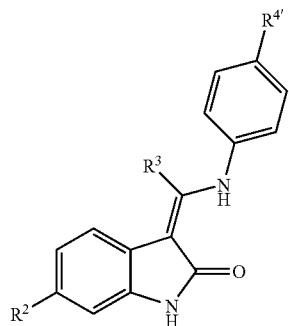
| Example | R² | R³ | R⁴' | Starting materials | Empirical formula | Mass spectrum | m.p. [° C.] | R_f value* |
|---|---|---|---|---|---|---|---|---|
| 11.23 | —F | NHCH₃ (propanamide with p-tBu-phenyl) | 1-Me-2-tBu-imidazolyl | 10.13** | C₂₉H₂₆FN₅O₂ | 496 [M + H]⁺ | 262–266 | 0.40 (C) |
| 11.24 | —F | NHCH₃ (propanamide with p-tBu-phenyl) | —SO₂Me | 10.14** | C₂₆H₂₄FN₃O₄S | 494 [M + H]⁺ | 180–188 | 0.60 (C) |
| 11.25 | —F | NHCH₃ (propanamide with p-tBu-phenyl) | C(Me)₂-C(O)-N(4-Me-piperazinyl) | 10.12** | C₃₁H₃₂FN₅O₃ | 542 [M + H]⁺ | 226–230 | 0.50 (C) |
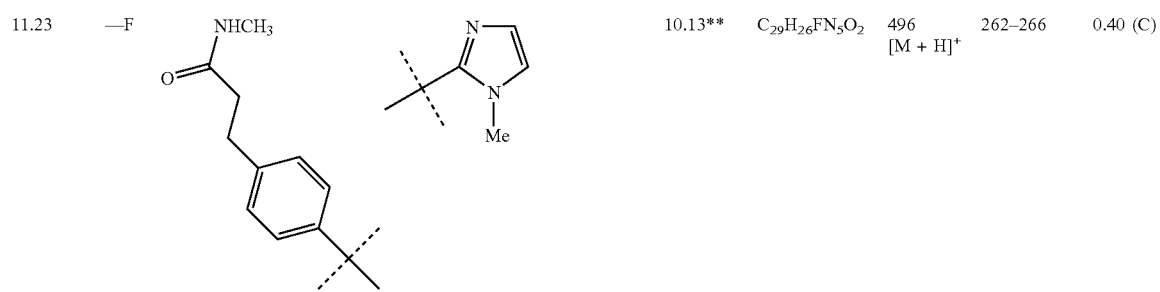
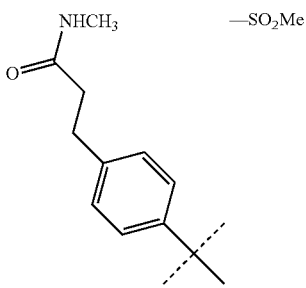
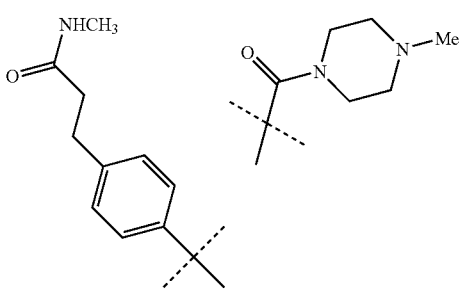

-continued

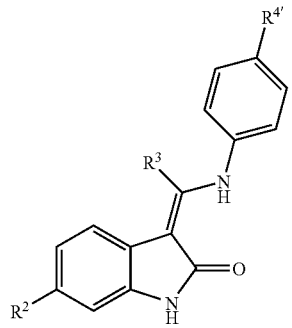
(I-11)

| Example | R² | R³ | R⁴' | Starting materials | Empirical formula | Mass spectrum | m.p. [° C.] | $R_f$ value* |
|---|---|---|---|---|---|---|---|---|
| 11.26 | —F | NHMe (with phenyl acetyl group, tBu substituent) | piperazine-NMe with H₃C-N-tBu acetyl linker | 10.16** | $C_{32}H_{35}FN_6O_3$ | 571 [M + H]⁺ | 213 | 0.10 (G) |
| 11.27 | —F | NHMe (with phenyl acetyl group, tBu substituent) | N-Me piperazine carbonyl with gem-dimethyl linker | 10.15** | $C_{30}H_{30}FN_5O_3$ | 528 [M + H]⁺ | 245 | 0.40 (G) |

*Eluent mixtures:
(A): silica gel, methylene chloride/methanol/ammonia = 5:1:0.01
(B): alumina, methylene chloride/ethanol = 20:1
(C): silica gel, methylene chloride/methanol/ammonia = 9:1:0.1
(D): silica gel, methylene chloride/methanol/ammonia = 6:1:0.1
(E): silica gel, methylene chloride/methanol/ammonia = 5:1:0.1
(F): silica gel, methylene chloride/methanol/ammonia = 7:1:0.1
(G): silica gel, methylene chloride/methanol = 9:1
**using methylammonium chloride as base equivalent
***using dimethylammonium chloride as base equivalent
****using piperidine hydrochloride as base equivalent

EXAMPLE 12.0

3-Z-[1-(4-Dimethylaminomethylanilino)-1-(4-acetylaminomethylphenyl)methylene]-6-chloro-2-indolinone 100 mg of 3-Z-[1-(4-dimethylaminomethylanilino)-1-(4-aminomethylphenyl)-methylene]-6-chloro-2-indolinone (starting material 7.0) are dissolved in 5 ml of methylene chloride and 5 ml of pyridine, and 20 µl of acetyl chloride are added at 0° C. The mixture is stirred at 0° C. for 10 minutes and at room temperature for a further 4 hours. Another 20 µl of acetyl chloride are then added, and the mixture is stirred at room temperature for 12 hours. After this time, the solvent is removed under reduced pressure and the residue is taken up in methylene chloride and washed with water. The aqueous phase is extracted twice with methylene chloride and the combined organic phases are dried over sodium sulphate. The solvent is removed using a rotary evaporator and the residue is washed with ether.

Yield: 51 mg (47% of theory),
$R_f$ value: 0.30 (silica gel, methylene chloride/methanol/ammonia=9:1:0.01)
m.p. 219–220° C.
$C_{27}H_{27}ClN_4O_2$
Mass spectrum: m/z=473/475 [M–H]⁻

The following compounds of the formula I-12 are prepared analogously to Example 12.0:

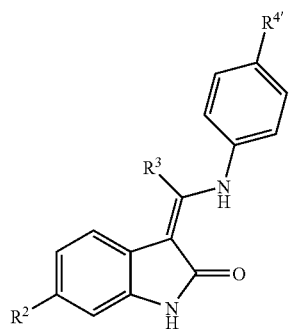
(I-12)
| Example | R² | R³ | R⁴' | Starting materials | Empirical formula | Mass spectrum | m.p. [° C.] | R_f-value* |
|---|---|---|---|---|---|---|---|---|
| 12.1 | —Cl | 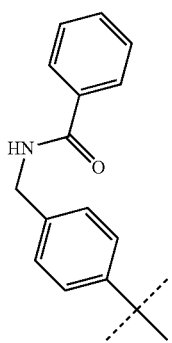 |  | 8.0 | $C_{32}H_{35}ClN_6O_3$ | 585/587 [M − H]⁻ | 252–255 | 0.25 (B) |
| 12.2 | —Cl |  | —CH₂—NMe₂ | 7.0 | $C_{32}H_{29}ClN_4O_2$ | 535/537 [M − H]⁻ | 238 (decomp.) | 0.45 (B) |
| 12.3 | —Cl | 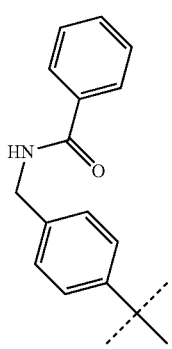 |  | 8.0 | $C_{37}H_{37}ClN_6O_3$ | 647/649 [M − H]⁻ | 282–284 | 0.40 (B) |

-continued
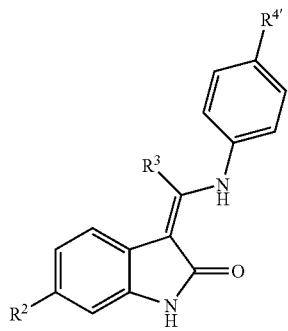
(I-12)
| Example | R² | R³ | R⁴' | Starting materials | Empirical formula | Mass spectrum | m.p. [° C.] | R_f-value* |
|---|---|---|---|---|---|---|---|---|
| 12.4 | —F | 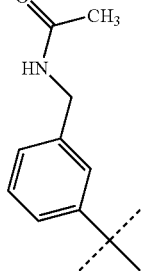 | —CH₂—NMe₂ | 9.0 | $C_{27}H_{27}FN_4O_2$ | 457 [M − H]⁻ | 245–250 | 0.40 (C) |
| 12.5 | —F | 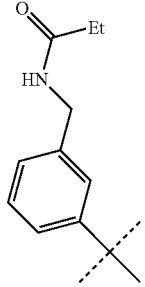 | —CH₂—NMe₂ | 9.0 | $C_{28}H_{29}FN_4O_2$ | 471 [M − H]⁻ | 212–214 | 0.35 (D) |
| 12.6 | —F | 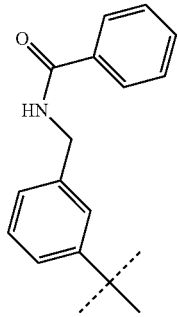 | —CH₂—NMe₂ | 9.0 | $C_{32}H_{29}FN_4O_2$ | 519 [M − H]⁻ | 237–240 | 0.40 (D) |

-continued
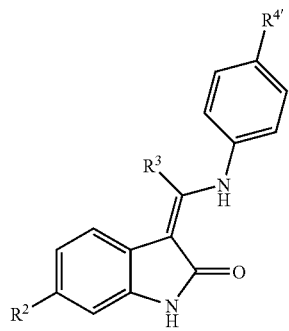
(I-12)
| Example | R² | R³ | R⁴' | Starting materials | Empirical formula | Mass spectrum | m.p. [° C.] | R_f-value* |
|---|---|---|---|---|---|---|---|---|
| 12.7 | —F | (N-benzyl 3-tert-butylphenylacetamide group) | —CH₂—NMe₂ | 9.0 | $C_{33}H_{31}FN_4O_2$ | 533 [M − ]⁻ | 187–190 | 0.30 (D) |
| 12.8 | —F | (N-(2-(3-tert-butylphenyl)ethyl)acetamide group, CH₃) | —CH₂—NMe₂ | 9.1 | $C_{28}H_{29}FN_4O_2$ | 471 [M − H]⁻ | 234–237 | 0.30 (D) |
| 12.9 | —F | (N-(2-(3-tert-butylphenyl)ethyl)benzamide group) | —CH₂—NMe₂ | 9.1 | $C_{33}H_{31}FN_4O_2$ | 533 [M − H]⁻ | 144–150 | 0.45 (C) |

-continued
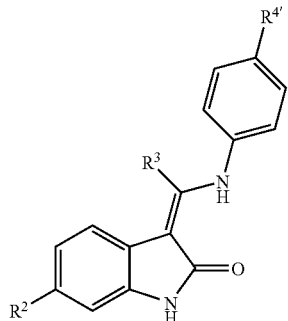
(I-12)
| Example | R² | R³ | R⁴' | Starting materials | Empirical formula | Mass spectrum | m.p. [° C.] | R_f-value* |
|---|---|---|---|---|---|---|---|---|
| 12.10 | —F | Et-C(=O)-NH-CH₂CH₂-(3-C₆H₄)- | —CH₂—NMe₂ | 9.1 | $C_{29}H_{31}FN_4O_2$ | 485 [M − H]⁻ | 235–237 | 0.25 (D) |
| 12.11 | —F | PhCH₂-C(=O)-NH-CH₂CH₂-(3-C₆H₄)- | —CH₂—NMe₂ | 9.1 | $C_{34}H_{33}FN_4O_2$ | 547 [M − H]⁻ | 217–220 | 0.30 (D) |
| 12.12 | —F | CH₃-C(=O)-NH-CH₂-(4-C₆H₄)- | —CH₂—NMe₂ | 9.2 | $C_{27}H_{27}FN_4O_2$ | 457 [M − H]⁻ | 112–120 | 0.25 (D) |

-continued
(I-12)
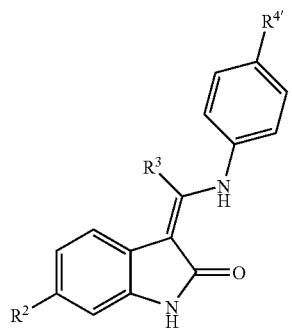
| Example | R² | R³ | R⁴' | Starting materials | Empirical formula | Mass spectrum | m.p. [° C.] | R_f-value* |
|---|---|---|---|---|---|---|---|---|
| 12.13 | —F | Et-C(O)-NH-CH₂-C₆H₄-C(CH₃)₃ | —CH₂—NMe₂ | 9.2 | C₂₈H₂₉FN₄O₂ | 586 [M + H]⁺ | 176–180 | 0.30 (D) |
| 12.14 | —F | PhCH₂-C(O)-NH-CH₂-C₆H₄-C(CH₃)₃ | —CH₂—NMe₂ | 9.2 | C₃₃H₃₁FN₄O₂ | 535 [M + H]⁺ | 80–85 | 0.35 (D) |
| 12.15 | —F | CH₃-C(O)-NH-CH₂-C₆H₄-C(CH₃)₃ | H₃C-N(CH₃)-C(O)-CH₂-N(piperazine)-NCH₃ | 9.3 | C₃₂H₃₅FN₆O₃ | 569 [M − H]⁻ | 230–235 | 0.35 (D) |
| 12.16 | —F | Et-C(O)-NH-CH₂-C₆H₄-C(CH₃)₃ | H₃C-N(CH₃)-C(O)-CH₂-N(piperazine)-NCH₃ | 9.3 | C₃₃H₃₇FN₆O₃ | 583 [M − H]⁻ | 205–210 | 0.30 (D) |

-continued (I-12)

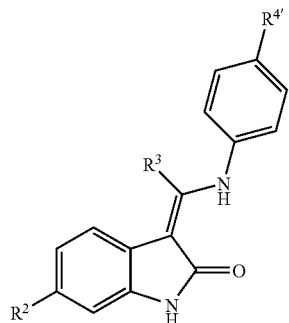

| Example | R² | R³ | R⁴' | Starting materials | Empirical formula | Mass spectrum | m.p. [° C.] | R_f-value* |
|---|---|---|---|---|---|---|---|---|
| 12.17 | —F | (phenylacetamide-N-CH₂-C₆H₄-4-tBu) | (H₃C-N(tBu)-C(O)-CH₂-N(piperazine)-NCH₃) | 9.3 | C₃₈H₃₉FN₆O₃ | 645 [M − H]⁻ | 217–220 | 0.35 (D) |
| 12.18 | —F | (cyclopropanecarboxamide-N-CH₂-C₆H₄-3-tBu) | (H₃C-N(tBu)-C(O)-CH₂-N(piperazine)-NCH₃) | 9.6 | C₃₄H₃₇FN₆O₃ | 597 [M + H]⁺ | 209–212 | 0.30 (D) |
| 12.19 | —F | (cyclobutanecarboxamide-N-CH₂-C₆H₄-3-tBu) | (H₃C-N(tBu)-C(O)-CH₂-N(piperazine)-NCH₃) | 9.6 | C₃₅H₃₉FN₆O₃ | 611 [M + H]⁺ | 190–193 | 0.30 (D) |

-continued
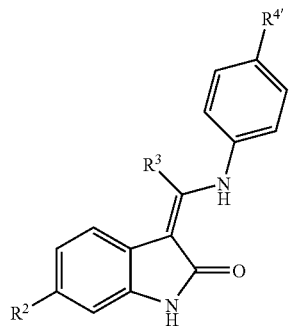
(I-12)
| Example | R² | R³ | R⁴' | Starting materials | Empirical formula | Mass spectrum | m.p. [° C.] | R_f-value* |
|---|---|---|---|---|---|---|---|---|
| 12.20 | —F | (pyridin-2-yl-C(O)NH-CH₂-3-phenyl-) | (4-methylpiperazin-1-yl-CH₂-C(O)-N(CH₃)-C(CH₃)₂-) | 9.6 | $C_{36}H_{36}FN_7O_3$ | 634 [M + H]⁺ | 160–163 | 0.30 (D) |
| 12.21 | —F | (cyclohexyl-C(O)NH-CH₂-3-phenyl-) | (4-methylpiperazin-1-yl-CH₂-C(O)-N(CH₃)-C(CH₃)₂-) | 9.6 | $C_{37}H_{43}FN_6O_3$ | 639 [M + H]⁺ | 223–227 | 0.30 (D) |
| 12.22 | —F | (pyridin-3-yl-C(O)NH-CH₂-3-phenyl-) | (4-methylpiperazin-1-yl-CH₂-C(O)-N(CH₃)-C(CH₃)₂-) | 9.6 | $C_{36}H_{36}FN_7O_3$ | 634 [M + H]⁺ | 170–175 | 0.25 (D) |

-continued

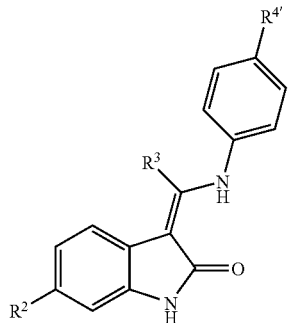

(I-12)

| Example | R² | R³ | R⁴' | Starting materials | Empirical formula | Mass spectrum | m.p. [° C.] | R_f-value* |
|---|---|---|---|---|---|---|---|---|
| 12.23 | —F | isobutyramide-N-(3-tert-butylbenzyl) | N-methyl-N-tert-butyl-2-(4-methylpiperazin-1-yl)acetamide | 9.6 | C₃₄H₃₉FN₆O₃ | 599 [M + H]⁺ | 194–196 | 0.20 (D) |
| 12.24 | —F | 3-methylbutyramide-N-(3-tert-butylbenzyl) | N-methyl-N-tert-butyl-2-(4-methylpiperazin-1-yl)acetamide | 9.6 | C₃₅H₄₁FN₆O₃ | 613 [M + H]⁺ | 197–200 | 0.70 (E) |
| 12.25 | —F | 2-cyclohexylacetamide-N-(3-tert-butylbenzyl) | N-methyl-N-tert-butyl-2-(4-methylpiperazin-1-yl)acetamide | 9.6 | C₃₈H₄₅FN₆O₃ | 653 [M + H]⁺ | 130–135 | 0.75 (E) |

-continued

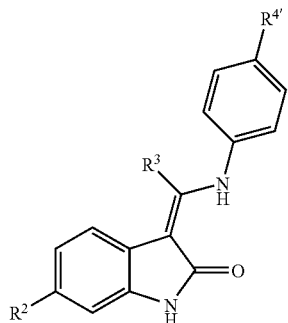
(I-12)

| Example | R² | R³ | R⁴' | Starting materials | Empirical formula | Mass spectrum | m.p. [° C.] | R_f-value* |
|---|---|---|---|---|---|---|---|---|
| 12.26 | —F | (structure: OMe-CH₂-C(O)-NH-CH₂-C₆H₄-C(CH₃)₃) | (structure: piperazine-NCH₃ with N(CH₃)-C(O)-CH₂- linker to C(CH₃)₃) | 9.6 | C₃₃H₃₇FN₆O₄ | 601 [M + H]⁺ | 155–159 | 0.60 (E) |
| 12.27 | —F | (structure: 2-MeO-C₆H₄-C(O)-NH-CH₂-C₆H₄-C(CH₃)₃) | (same piperazine linker) | 9.6 | C₃₈H₃₉FN₆O₄ | 663 [M + H]⁺ | 168–172 | 0.35 (C) |
| 12.28 | —F | (structure: (CH₃)₃C-CH₂-C(O)-NH-CH₂-C₆H₄-C(CH₃)₃) | (same piperazine linker) | 9.6 | C₃₆H₄₃FN₆O₃ | 627 [M + H]⁺ | 85–90 | 0.35 (C) |

-continued (I-12)

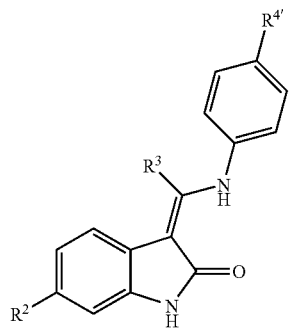

| Example | R² | R³ | R⁴' | Starting materials | Empirical formula | Mass spectrum | m.p. [° C.] | R_f-value* |
|---|---|---|---|---|---|---|---|---|
| 12.29 | —F | (thiophene-2-carboxamide-N-(3-tert-butylbenzyl)) | (H₃C-N(tBu)-C(=O)-CH₂-N(piperazine)-NCH₃) | 9.6 | C₃₅H₃₅FN₆O₃S | 639 [M + H]⁺ | 170–175 | 0.25 (C) |
| 12.30 | —F | (CH₃)₃C-C(=O)-NH-CH₂-(3-tert-butylphenyl) | (H₃C-N(tBu)-C(=O)-CH₂-N(piperazine)-NCH₃) | 9.6 | C₃₅H₄₁FN₆O₃ | 613 [M + H]⁺ | 242–245 | 0.30 (C) |
| 12.31 | —F | (furan-2-carboxamide-N-(3-tert-butylbenzyl)) | (H₃C-N(tBu)-C(=O)-CH₂-N(piperazine)-NCH₃) | 9.6 | C₃₅H₃₅FN₆O₄ | 623 [M + H]⁺ | 155–160 | 0.65 (F) |

-continued (I-12)

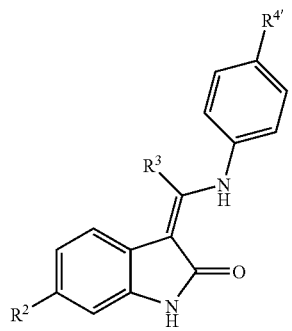

| Example | R² | R³ | R⁴' | Starting materials | Empirical formula | Mass spectrum | m.p. [° C.] | R_f-value* |
|---|---|---|---|---|---|---|---|---|
| 12.32 | —F | CH₃C(O)NH-CH₂-(3-tBu-C₆H₄)- | 4-[(N-methyl-N-tert-butyl)aminocarbonylmethyl-N'-methylpiperazinyl]- | 9.6 | C₃₂H₃₅FN₆O₃ | 571 [M + H]⁺ | 190–195 | 0.60 (F) |
| 12.33 | —F | EtC(O)NH-CH₂-(3-tBu-C₆H₄)- | 4-[(N-methyl-N-tert-butyl)aminocarbonylmethyl-N'-methylpiperazinyl]- | 9.6 | C₃₃H₃₇FN₆O₃ | 585 [M + H]⁺ | 203–209 | 0.65 (E) |
| 12.34 | —F | PhC(O)NH-CH₂-(3-tBu-C₆H₄)- | 4-[(N-methyl-N-tert-butyl)aminocarbonylmethyl-N'-methylpiperazinyl]- | 9.6 | C₃₇H₃₇FN₆O₃ | 633 [M + H]⁺ | 145–150 | 0.60 (F) |

(I-12)
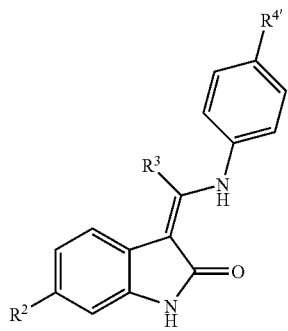
| Example | R² | R³ | R⁴' | Starting materials | Empirical formula | Mass spectrum | m.p. [° C.] | $R_f$-value* |
|---|---|---|---|---|---|---|---|---|
| 12.35 | —F | 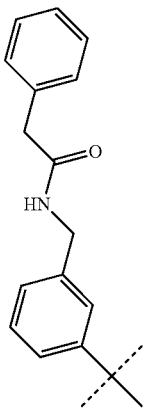 | 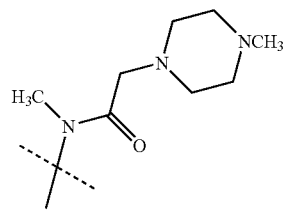 | 9.6 | $C_{38}H_{39}FN_6O_3$ | 647 [M + H]⁺ | 148–151 | 0.65 (F) |
| 12.36 | —F | 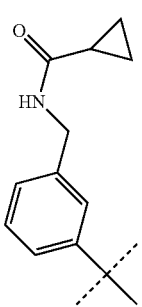 | —CH₂—NMe₂ | 9.0 | $C_{29}H_{29}FN_4O_2$ | 485 [M + H]⁺ | 216–220 | 0.35 (D) |
| 12.37 | —F | 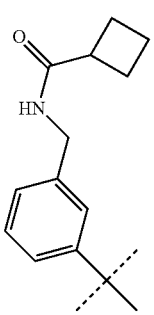 | —CH₂—NMe₂ | 9.0 | $C_{30}H_{31}FN_4O_2$ | 499 [M + H]⁺ | 214–217 | 0.35 (D) |

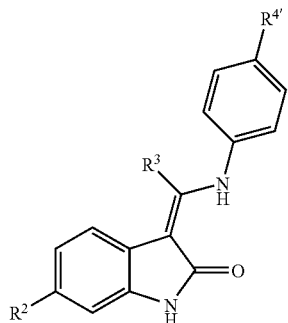
(I-12)
| Example | R² | R³ | R⁴' | Starting materials | Empirical formula | Mass spectrum | m.p. [° C.] | R_f-value* |
|---|---|---|---|---|---|---|---|---|
| 12.38 | —F | 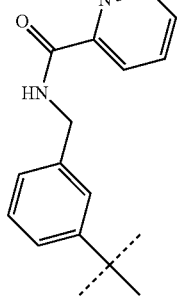 | —CH₂—NMe₂ | 9.0 | $C_{31}H_{28}FN_5O_2$ | 522 [M + H]⁺ | 205–210 | 0.35 (D) |
| 12.39 | —F | 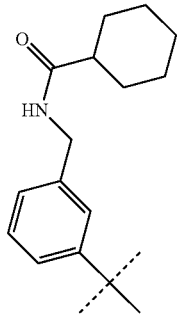 | —CH₂—NMe₂ | 9.0 | $C_{32}H_{35}FN_4O_2$ | 527 [M + H]⁺ | 235–237 | 0.35 (D) |
| 12.40 | —F | 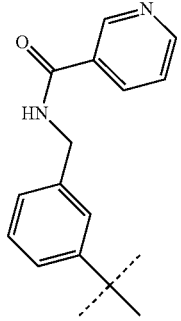 | —CH₂—NMe₂ | 9.0 | $C_{31}H_{28}FN_5O_2$ | 520 [M − H]⁻ | 135–140 | 0.20 (D) |

-continued
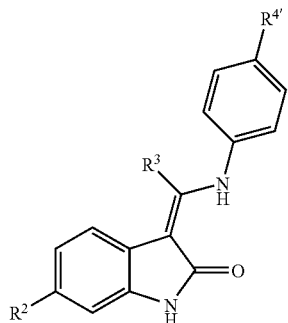
(I-12)
| Example | R² | R³ | R⁴′ | Starting materials | Empirical formula | Mass spectrum | m.p. [° C.] | R_f-value* |
|---|---|---|---|---|---|---|---|---|
| 12.41 | —F | (isobutyramide-CH₂-3-phenyl) | —CH₂—NMe₂ | 9.0 | C₂₉H₃₁FN₄O₂ | 487 [M + H]⁺ | 210–215 | 0.20 (D) |
| 12.42 | —F | (isovaleramide-CH₂-3-phenyl) | —CH₂—NMe₂ | 9.0 | C₃₀H₃₃FN₄O₂ | 501 [M + H]⁺ | 202–206 | 0.25 (D) |
| 12.43 | —F | (cyclohexylacetamide-CH₂-3-phenyl) | —CH₂—NMe₂ | 9.0 | C₃₃H₃₇FN₄O₂ | 541 [M + H]⁺ | 198–203 | 0.35 (D) |

-continued
(I-12)
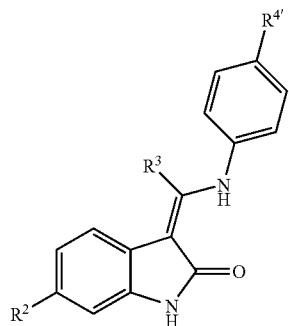
| Example | R² | R³ | R⁴' | Starting materials | Empirical formula | Mass spectrum | m.p. [° C.] | R_f-value* |
|---|---|---|---|---|---|---|---|---|
| 12.44 | —F | 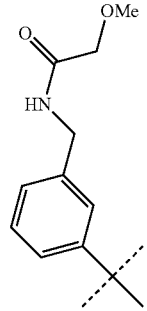 | —CH₂—NMe₂ | 9.0 | $C_{28}H_{29}FN_4O_3$ | 489 [M + H]⁺ | 173–177 | 0.35 (D) |
| 12.45 | —F | 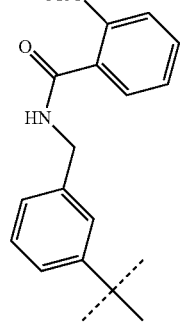 | —CH₂—NMe₂ | 9.0 | $C_{33}H_{31}FN_4O_3$ | 549 [M − H]⁻ | 202–207 | 0.50 (C) |
| 12.46 | —F | 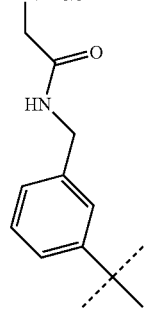 | —CH₂—NMe₂ | 9.0 | $C_{31}H_{35}FN_4O_2$ | 513 [M − H]⁻ | 203–209 | 0.45 (C) |

-continued
(I-12)
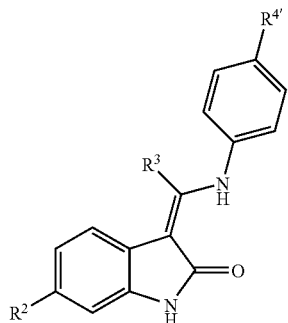
| Example | $R^2$ | $R^3$ | $R^{4'}$ | Starting materials | Empirical formula | Mass spectrum | m.p. [° C.] | $R_f$-value* |
|---|---|---|---|---|---|---|---|---|
| 12.47 | —F | 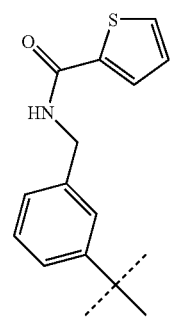 | —CH$_2$—NMe$_2$ | 9.0 | C$_{30}$H$_{27}$FN$_4$O$_2$S | 527 [M + H]$^+$ | 245–250 | 0.35 (C) |
| 12.48 | —F | 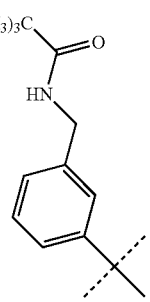 | —CH$_2$—NMe$_2$ | 9.0 | C$_{30}$H$_{33}$FN$_4$O$_2$ | 501 [M + H]$^+$ | 248–252 | 0.45 (C) |

-continued

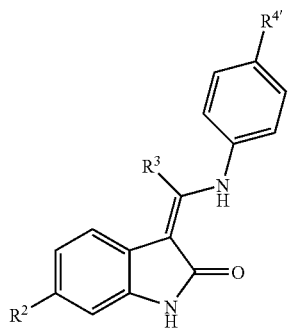
(I-12)

| Example | R² | R³ | R⁴' | Starting materials | Empirical formula | Mass spectrum | m.p. [° C.] | R_f-value* |
|---|---|---|---|---|---|---|---|---|
| 12.49 | —F | 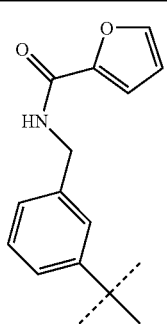 | —CH₂—NMe₂ | 9.0 | $C_{30}H_{27}FN_4O_3$ | 511 [M + H]⁺ | 216–219 | 0.30 (C) |
| 12.50 | —F | 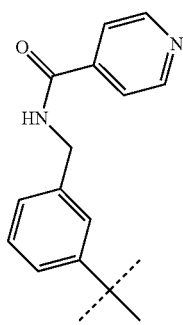 | —CH₂—NMe₂ | 9.0 | $C_{31}H_{28}FN_5O_2$ | 522 [M + H]⁺ | 167–170 | 0.20 (D) |

*Eluent mixtures:
(A): silica gel, methylene chloride/ethanol/ammonia = 20:1:0.01
(B): silica gel, methylene chloride/methanol/ammonia = 9:1:0.01
(C): alumina, methylene chloride/methanol = 19:1
(D): silica gel, methylene chloride/methanol/ammonia = 9:1:0.1
(E): silica gel, methylene chloride/methanol/ammonia = 8:2:0.2
(F): alumina, methylene chloride/methanol = 9:1

Alternatively, the following acylating agents were used:

benzoyl chloride, propionyl chloride, phenylacetyl chloride, cyclopropanecarbonyl chloride, cyclobutanecarbonyl chloride, pyridin-2-ylcarbonyl chloride, pyridin-3-ylcarbonyl chloride, pyridin-4-ylcarbonyl chloride, cyclohexylcarbonyl chloride, isobutyryl chloride, 3-methylbutyryl chloride, cyclohexylmethylcarbonyl chloride, methoxyacetyl chloride, 2-methoxybenzoyl chloride, tert-butylacetyl chloride, thiophene-2-carbonyl chloride, pivaloyl chloride, 2-furoyl chloride

EXAMPLE 13.0

3-Z-[1-(4-Trimethylammoniummethylanilino)-1-(4-(2-carboxyethyl)phenyl)methylene]-6-fluoro-2-indolinone iodide 200 mg of 3-Z-[1-(4-dimethylaminomethylanilino)-1-(4-(2-carboxyethyl)phenyl)methylene]-6-fluoro-2-indolinone (starting material 10.1) are dissolved in 40 ml of acetone, and 250 ml of methyl iodide are added. The mixture is stirred at room temperature for 20 hours. After this time, the resulting residue is filtered off with suction. The product is dried at 80° C. under reduced pressure.

Yield: 200 mg (83% of theory), $R_f$ value: 0.50 (reversed phase RP8, methanol/sodium chloride solution (5%)=4:1)

m.p. 210° C.

$C_{28}H_{29}FN_3O_3I$

Mass spectrum: m/z=474 [M+H]$^+$

The following compound of the formula I-13 is prepared analogously to Example 13.0:

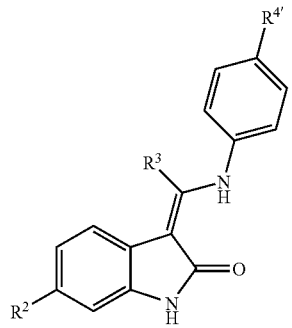

(I-13)

| Example | $R^2$ | $R^3$ | $R^{4'}$ | Starting materials | Empirical formula | Mass spectrum | m.p. [° C.] | $R_f$ value* |
|---|---|---|---|---|---|---|---|---|
| 13.1 | —F | | | 10.3 | $C_{28}H_{29}FN_3O_3I$ | 474 [M + H]$^+$ | 150 | 0.50 (A) |

*Eluent mixture:
(A): reversed phase RP8, methanol/sodium chloride solution (5%) = 4:1

EXAMPLE 14.0

3-Z-[1-(4-Guanidinomethylanilino)-1-(4-(2-carboxyethyl)phenyl)methylene]-6-fluoro-2-indolinone iodide 170 mg of 3-Z-[1-(4-aminomethylanilino)-1-(4-(2-carboxyethyl)phenyl)methylene]-6-fluoro-2-indolinone (starting material 10.50) are dissolved in 20 ml of tetrahydrofuran, and 390 mg of 3,5-dimethylpyrazole-1-carboxamidine nitrate and 330 ml of diethylisopropylamine are added. The mixture is stirred under reflux for 10 hours. After this time, the solvent is concentrated, water is added and the resulting residue is filtered off with suction. The product is dried at 80° C.

Yield: 150 mg (81% of theory), $R_f$ value: 0.40 (silica gel, methylene chloride/methanol/acetic acid=5:1:0.1)

m.p. 290° C.

$C_{26}H_{24}FN_5O_3$

Mass spectrum: m/z=474 [M+H]$^+$

The following compound of the formula I-14 is prepared analogously to Example 14.0:

(I-14)

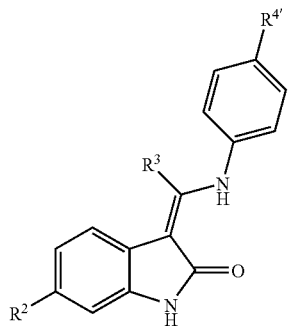

| Example | R² | R³ | R⁴' | Starting materials | Empirical formula | Mass spectrum | m.p. [° C.] | $R_f$ value* |
|---|---|---|---|---|---|---|---|---|
| 14.1 | —F | (propanoic acid with meta-substituted phenyl group) | (guanidinyl-methyl group) | 10.64 | $C_{26}H_{24}FN_5O_3$ | 474 [M + H]⁺ | 305 | 0.70 (A) |

*Eluent mixture:
(A): reversed phase RP8, methanol/sodium chloride solution (5%) = 4:1

EXAMPLE 15

Dry vial with 75 mg of active compound per 10 ml
Composition:

| | |
|---|---|
| Active compound | 75.0 mg |
| Mannitol | 50.0 mg |
| Water for injection | ad 10.0 ml |

Preparation:

Active compound and mannitol were dissolved in water. After filling, the product is freeze-dried. The ready-to-use solution is obtained by dissolving the product in water for injection.

EXAMPLE 16

Dry vial with 35 mg of active compound per 2 ml
Composition:

| | |
|---|---|
| Active compound | 35.0 mg |
| Mannitol | 100.0 mg |
| Water for injection | ad 2.0 ml |

Preparation:

Active compound and mannitol were dissolved in water. After filling, the product is freeze-dried. The ready-to-use solution is obtained by dissolving the product in water for injection.

EXAMPLE 17

Tablet with 50 mg of active compound
Composition:

| | |
|---|---|
| (1) Active compound | 50.0 mg |
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Preparation:

(1), (2) and (3) are mixed and granulated using an aqueous solution of (4). (5) is added to the dried granules. From this mixture, biplanar tablets having a facet on both sides and being partially scored on one side are pressed.

Diameter of the tablets: 9 mm.

EXAMPLE 18

Tablet with 350 mg of active compound
Composition:

| | |
|---|---|
| (1) Active compound | 350.0 mg |
| (2) Lactose | 136.0 mg |
| (3) Maize starch | 80.0 mg |

-continued

| | |
|---|---|
| (4) Polyvinylpyrrolidone | 30.0 mg |
| (5) Magnesium stearate | 4.0 mg |
| | 600.0 mg |

Preparation:

(1), (2) and (3) are mixed and granulated using an aqueous solution of (4). (5) is added to the dried granules. From this mixture, biplanar tablets having a facet on both sides and being partially scored on one side are pressed.

Diameter of the tablets: 12 mm.

EXAMPLE 19

Capsules with 50 mg of active compound

Composition:

| | |
|---|---|
| (1) Active compound | 50.0 mg |
| (2) Maize starch, dried | 58.0 mg |
| (3) Lactose, powdered | 50.0 mg |
| (4) Magnesium stearate | 2.0 mg |
| | 160.0 mg |

Preparation:

(1) is ground with (3). This ground material is, with vigorous mixing, added to the mixture of (2) and (4).

This powder mixture is, in a capsule filling machine, filled into hard gelatin capsules size 3.

EXAMPLE 20

Capsules with 350 mg of active compound

Composition:

| | |
|---|---|
| (1) Active compound | 350.0 mg |
| (2) Maize starch, dried | 46.0 mg |
| (3) Lactose, powdered | 30.0 mg |
| (4) Magnesium stearate | 4.0 mg |
| | 430.0 mg |

Preparation:

(1) is ground with (3). This ground material is, with vigorous mixing, added to the mixture of (2) and (4).

This powder mixture is, in a capsule filling machine, filled into hard gelatin capsules size 0.

EXAMPLE 21

Suppositories with 100 mg of active compound 1 suppository contains:

| | |
|---|---|
| Active compound | 100.0 mg |
| Polyethylene glycol (MW 1500) | 600.0 mg |

-continued

| | |
|---|---|
| Polyethylene glycol (MW 6000) | 460.0 mg |
| Polyethylene sorbitan monostearate | 840.0 mg |
| | 2000.0 mg |

Preparation:

The polyethylene glycol is melted together with polyethylene sorbitan monostearate. At 40° C., the ground active substance is homogeneously dispersed in the melt. The melt is cooled to 38° C. and poured into slightly pre-cooled suppository moulds.

Analogously to the examples above, it is possible to prepare the following compounds:

(1) 3-Z-[1-(4-(N-(2-dimethylaminoethyl)-N-methylsulphonylamino)anilino)-1-(4-(2-carboxyethyl)phenyl)methylene]-6-chloro-2-indolinone (2) 3-Z-[1-(4-(N-(dimethylaminomethylcarbonyl)-N-methylamino)anilino)-1-(4-(2-carboxyethyl)phenyl)methylene]-6-chloro-2-indolinone (3) 3-Z-[1-(4-(N-(2-dimethylaminoethyl)-N-acetylamino)anilino)-1-(4-(2-carboxyethyl)phenyl)methylene]-6-chloro-2-indolinone (4) 3-Z-[1-(4-(N-(2-methylaminoethyl)-N-acetylamino)anilino)-1-(4-(2-carboxyethyl)phenyl)methylene]-6-chloro-2-indolinone (5) 3-Z-[1-(4-(N-(3-dimethylaminopropyl)-N-acetylamino)anilino)-1-(4-(2-carboxyethyl)phenyl)methylene]-6-chloro-2-indolinone (6) 3-Z-[1-(4-(N-(3-methylaminopropyl)-N-acetylamino)anilino)-1-(4-(2-carboxyethyl)phenyl)methylene]-6-chloro-2-indolinone (7) 3-Z-[1-(4-(3-dimethylaminopropyl)anilino)-1-(4-(2-carboxyethyl)phenyl)methylene]-6-chloro-2-indolinone (8) 3-Z-[1-(4-ethylaminomethylanilino)-1-(4-(2-carboxyethyl)phenyl)methylene]-6-chloro-2-indolinone (9) 3-Z-[1-(4-methylaminomethylanilino)-1-(4-(2-carboxyethyl)phenyl)methylene]-6-chloro-2-indolinone

(10) 3-Z-[1-(4-(N-(4-methylpiperazin-1-ylmethylcarbonyl)-N-methylamino)anilino)-1-(4-(2-carboxyethyl)phenyl)methylene]-6-chloro-2-indolinone

(11) 3-Z-[1-(4-(4-methylpiperazin-1-ylcarbonyl)anilino)-1-(4-(2-carboxyethyl)phenyl)methylene]-6-chloro-2-indolinone

(12) 3-Z-[1-(4-(N-(3-dimethylaminopropyl)-N-methylsulphonylamino)anilino)-1-(4-(2-carboxyethyl)phenyl)methylene]-6-chloro-2-indolinone

(13) 3-Z-[1-(4-(N-(2-dimethylaminoethyl)-N-propylsulphonylamino)anilino)-1-(4-(2-carboxyethyl)phenyl)methylene]-6-chloro-2-indolinone

(14) 3-Z-[1-(4-aminomethylanilino)-1-(4-(2-carboxyethyl)phenyl)methylene]-6-chloro-2-indolinone

(15) 3-Z-[1-(3-(methylaminomethyl)anilino)-1-(4-(2-carboxyethyl)phenyl)methylene]-6-chloro-2-indolinone

(16) 3-Z-[1-(3-(2-dimethylaminoethyl)anilino)-1-(4-(2-carboxyethyl)phenyl)methylene]-6-chloro-2-indolinone

(17) 3-Z-[1-(3-(3-dimethylaminopropyl)anilino)-1-(4-(2-carboxyethyl)phenyl)methylene]-6-chloro-2-indolinone

(18) 3-Z-[1-(4-(N-(dimethylamino-carbonylmethyl)-N-methylsulphonylamino)anilino)-1-(4-(2-carboxyethyl)phenyl)methylene]-6-chloro-2-indolinone

(19) 3-Z-[1-(4-(N-methyl-N-methylsulphonylamino)anilino)-1-(4-(2-carboxyethyl)phenyl)methylene]-6-chloro-2-indolinone

(20) 3-Z-[1-(4-(N-methyl-N-acetylamino)anilino)-1-(4-(2-carboxyethyl)phenyl)methylene]-6-chloro-2-indolinone
(21) 3-Z-[1-(4-(N-(N-(2-dimethylaminoethyl)-N-methylaminomethylcarbonyl)-N-methylamino)anilino)-1-(4-(2-carboxyethyl)phenyl)methylene]-6-chloro-2-indolinone
(22) 3-Z-[1-(4-(2-diethylaminoethylsulphonyl)anilino)-1-(4-(2-carboxyethyl)phenyl)methylene]-6-chloro-2-indolinone
(23) 3-Z-[1-(4-(N-(2-dimethylaminoethyl-carbonyl)-N-methylamino)anilino)-1-(4-(2-carboxyethyl)phenyl)methylene]-6-chloro-2-indolinone
(24) 3-Z-[1-(4-(N-(2-dimethylaminoethyl)-N-methylaminomethyl)anilino)-1-(4-(2-carboxyethyl)phenyl)methylene]-6-chloro-2-indolinone
(25) 3-Z-[1-(4-(2-dimethylaminoethoxy)anilino)-1-(4-(2-carboxyethyl)phenyl)methylene]-6-chloro-2-indolinone
(26) 3-Z-[1-(4-(N-(4-dimethylaminobutylcarbonyl)-N-methylamino)anilino)-1-(4-(2-carboxyethyl)phenyl)methylene]-6-chloro-2-indolinone
(27) 3-Z-[1-(4-(N-(3-dimethylaminopropylcarbonyl)-N-methylamino)anilino)-1-(4-(2-carboxyethyl)phenyl)methylene]-6-chloro-2-indolinone
(28) 3-Z-[1-(4-(methylethylaminomethyl)anilino)-1-(4-(2-carboxyethyl)phenyl)methylene]-6-chloro-2-indolinone
(29) 3-Z-[1-(4-(methylpropylaminomethyl)anilino)-1-(4-(2-carboxyethyl)phenyl)methylene]-6-chloro-2-indolinone
(30) 3-Z-[1-(4-(methylbenzylaminomethyl)anilino)-1-(4-(2-carboxyethyl)phenyl)methylene]-6-chloro-2-indolinone
(31) 3-Z-[1-(4-(N-(2-dimethylaminoethyl)-N-methylaminomethyl)anilino)-1-(4-(2-carboxyethyl)phenylmethylene]-6-chloro-2-indolinone
(32) 3-Z-[1-(4-(azetidin-1-ylmethyl)anilino)-1-(4-(2-carboxyethyl)phenyl)methylene]-6-chloro-2-indolinone
(33) 3-Z-[1-(4-((4-methylpiperazin-1-yl)methyl)anilino)-1-(4-(2-carboxyethyl)phenyl)methylene]-6-chloro-2-indolinone
(34) 3-Z-[1-(4-(piperazin-1-ylmethyl)anilino)-1-(4-(2-carboxyethyl)phenyl)methylene]-6-chloro-2-indolinone
(35) 3-Z-[1-(4-(morpholin-4-ylmethyl)anilino)-1-(4-(2-carboxyethyl)phenyl)methylene]-6-chloro-2-indolinone
(36) 3-Z-[1-(4-(thiomorpholin-4-ylmethyl)anilino)-1-(4-(2-carboxyethyl)phenyl)methylene]-6-chloro-2-indolinone
(37) 3-Z-[1-(4-(imidazol-1-ylmethyl)anilino)-1-(4-(2-carboxyethyl)phenyl)methylene]-6-chloro-2-indolinone
(38) 3-Z-[1-(4-(N-(2-dimethylaminoethyl)-N-methylsulphonylamino)anilino)-1-(3-(2-carboxyethyl)phenyl)methylene]-6-chloro-2-indolinone
(39) 3-Z-[1-(4-(N-(dimethylaminomethylcarbonyl)-N-methylamino)anilino)-1-(3-(2-carboxyethyl)phenyl)methylene]-6-chloro-2-indolinone
(40) 3-Z-[1-(4-(N-(2-dimethylaminoethyl)-N-acetylamino)anilino)-1-(3-(2-carboxyethyl)phenyl)methylene]-6-chloro-2-indolinone
(41) 3-Z-[1-(4-(N-(2-methylaminoethyl)-N-acetylamino)anilino)-1-(3-(2-carboxyethyl)phenyl)methylene]-6-chloro-2-indolinone
(42) 3-Z-[1-(4-(N-(3-dimethylaminopropyl)-N-acetylamino)anilino)-1-(3-(2-carboxyethyl)phenyl)methylene]-6-chloro-2-indolinone
(43) 3-Z-[1-(4-(N-(3-methylaminopropyl)-N-acetylamino)anilino)-1-(3-(2-carboxyethyl)phenyl)methylene]-6-chloro-2-indolinone
(44) 3-Z-[1-(4-(3-dimethylaminopropyl)anilino)-1-(3-(2-carboxyethyl)phenyl)methylene]-6-chloro-2-indolinone
(45) 3-Z-[1-(4-ethylaminomethylanilino)-1-(3-(2-carboxyethyl)phenyl)methylene]-6-chloro-2-indolinone
(46) 3-Z-[1-(4-methylaminomethylanilino)-1-(3-(2-carboxyethyl)phenyl)methylene]-6-chloro-2-indolinone
(47) 3-Z-[1-(4-(N-(4-methylpiperazin-1-ylmethylcarbonyl)-N-methylamino)anilino)-1-(3-(2-carboxyethyl)phenyl)methylene]-6-chloro-2-indolinone
(48) 3-Z-[1-(4-(4-methylpiperazin-1-ylcarbonyl)anilino)-1-(3-(2-carboxyethyl)phenyl)methylene]-6-chloro-2-indolinone
(49) 3-Z-[1-(1-(4-(N-(3-dimethylaminopropyl)-N-methylsulphonylamino)anilino)-1-(3-(2-carboxyethyl)phenyl)methylene]-6-chloro-2-indolinone
(50) 3-Z-[1-(4-(N-(2-dimethylaminoethyl)-N-propylsulphonylamino)anilino)-1-(3-(2-carboxyethyl)phenyl)methylene]-6-chloro-2-indolinone
(51) 3-Z-[1-(4-aminomethylanilino)-1-(3-(2-carboxyethyl)phenyl)methylene]-6-chloro-2-indolinone
(52) 3-Z-[1-(3-(dimethylaminomethyl)anilino)-1-(3-(2-carboxyethyl)phenyl)methylene]-6-chloro-2-indolinone
(53) 3-Z-[1-(3-(methylaminomethyl)anilino)-1-(3-(2-carboxyethyl)phenyl)methylene]-6-chloro-2-indolinone
(54) 3-Z-[1-(3-(2-dimethylaminoethyl)anilino)-1-(3-(2-carboxyethyl)phenyl)methylene]-6-chloro-2-indolinone
(55) 3-Z-[1-(3-(3-dimethylaminopropyl)anilino)-1-(3-(2-carboxyethyl)phenyl)methylene]-6-chloro-2-indolinone
(56) 3-Z-[1-(4-(2-dimethylaminoethyl)anilino)-1-(3-(2-carboxyethyl)phenyl)methylene]-6-chloro-2-indolinone
(57) 3-Z-[1-(4-(N-(dimethylaminocarbonylmethyl)-N-methylsulphonylamino)anilino)-1-(3-(2-carboxyethyl)phenyl)methylene]-6-chloro-2-indolinone
(58) 3-Z-[1-(4-(N-methyl-N-methylsulphonylamino)anilino)-1-(3-(2-carboxyethyl)phenyl)methylene]-6-chloro-2-indolinone
(59) 3-Z-[1-(4-(N-methyl-N-acetylamino)anilino)-1-(3-(2-carboxyethyl)phenyl)methylene]-6-chloro-2-indolinone
(60) 3-Z-[1-(4-(1-methylimidazol-2-yl)anilino)-1-(3-(2-carboxyethyl)phenyl)methylene]-6-chloro-2-indolinone
(61) 3-Z-[1-(4-(N-(N-(2-dimethylaminoethyl)-N-methylaminomethylcarbonyl)-N-methylamino)anilino)-1-(3-(2-carboxyethyl)phenyl)methylene]-6-chloro-2-indolinone
(62) 3-Z-[1-(4-(2-diethylaminoethylsulphonyl)anilino)-1-(3-(2-carboxyethyl)phenyl)methylene]-6-chloro-2-indolinone
(63) 3-Z-[1-(4-(N-(2-dimethylaminoethylcarbonyl)-N-methylamino)anilino)-1-(3-(2-carboxyethyl)phenyl)methylene]-6-chloro-2-indolinone
(64) 3-Z-[1-(4-(N-(2-dimethylaminoethyl)-N-methylaminomethyl)anilino)-1-(3-(2-carboxyethyl)phenyl)methylene]-6-chloro-2-indolinone
(65) 3-Z-[1-(4-(2-dimethylaminoethoxy)anilino)-1-(3-(2-carboxyethyl)phenyl)methylene]-6-chloro-2-indolinone
(66) 3-Z-[1-(4-(N-(4-dimethylaminobutylcarbonyl)-N-methylamino)anilino)-1-(3-(2-carboxyethyl)phenyl)methylene]-6-chloro-2-indolinone
(67) 3-Z-[1-(4-(N-(3-dimethylaminopropylcarbonyl)-N-methylamino)anilino)-1-(3-(2-carboxyethyl)phenyl)methylene]-6-chloro-2-indolinone
(68) 3-Z-[1-(4-(methylethylaminomethyl)anilino)-1-(3-(2-carboxyethyl)phenyl)methylene]-6-chloro-2-indolinone
(69) 3-Z-[1-(4-(methylpropylaminomethyl)anilino)-1-(3-(2-carboxyethyl)phenyl)methylene]-6-chloro-2-indolinone
(70) 3-Z-[1-(4-(methylbenzylaminomethyl)anilino)-1-(3-(2-carboxyethyl)phenyl)methylene]-6-chloro-2-indolinone
(71) 3-Z-[1-(4-(diethylaminomethyl)anilino)-1-(3-(2-carboxyethyl)phenyl)methylene]-6-chloro-2-indolinone
(72) 3-Z-[1-(4-(N-(2-dimethylaminoethyl)-N-methylaminomethyl)anilino)-1-(3-(2-carboxyethyl)phenylmethylene]-6-chloro-2-indolinone

(73) 3-Z-[1-(4-(pyrrolidin-1-ylmethyl)anilino)-1-(3-(2-carboxyethyl)phenyl)methylene)-6-chloro-2-indolinone
(74) 3-Z-[1-(4-(azetidin-1-ylmethyl)anilino)-1-(3-(2-carboxyethyl)phenyl)methylene]-6-chloro-2-indolinone
(75) 3-Z-[1-(4-((4-methylpiperazin-1-yl)methyl)anilino)-1-(3-(2-carboxyethyl)phenyl)methylene]-6-chloro-2-indolinone
(76) 3-Z-[1-(4-(piperazin-1-ylmethyl)anilino)-1-(3-(2-carboxyethyl)phenyl)methylene)-6-chloro-2-indolinone
(77) 3-Z-[1-(4-(morpholin-4-ylmethyl)anilino)-1-(3-(2-carboxyethyl)phenyl)methylene)-6-chloro-2-indolinone
(78) 3-Z-[1-(4-(thiomorpholin-4-ylmethyl)anilino)-1-(3-(2-carboxyethyl)phenyl)methylene]-6-chloro-2-indolinone
(79) 3-Z-[1-(4-(imidazol-1-yl methyl)anilino)-1-(3-(2-carboxyethyl)phenyl)methylene)-6-chloro-2-indolinone
(80) 3-Z-[1-(4-(N-(2-methylaminoethyl)-N-acetylamino)anilino)-1-(4-(2-carboxyethyl)phenyl)methylene]-6-fluoro-2-indolinone
(81) 3-Z-[1-(4-(N-(3-methylaminopropyl)-N-acetylamino)anilino)-1-(4-(2-carboxyethyl)phenyl)methylene]-6-fluoro-2-indolinone
(82) 3-Z-[1-(4-(3-dimethylaminopropyl)anilino)-1-(4-(2-carboxyethyl)phenyl)methylene]-6-fluoro-2-indolinone
(83) 3-Z-[1-(4-ethylaminomethylanilino)-1-(4-(2-carboxyethyl)phenyl)methylene]-6-fluoro-2-indolinone
(84) 3-Z-[1-(4-(N-(3-dimethylaminopropyl)-N-methylsulphonylamino)anilino)-1-(4-(2-carboxyethyl)phenyl)methylene]-6-fluoro-2-indolinone
(85) 3-Z-[1-(4-(N-(2-dimethylaminoethyl)-N-propylsulphonylamino)anilino)-1-(4-(2-carboxyethyl)phenyl)methylene]-6-fluoro-2-indolinone
(86) 3-Z-[1-(3-(methylaminomethyl)anilino)-1-(4-(2-carboxyethyl)phenyl)methylene]-6-fluoro-2-indolinone
(87) 3-Z-[1-(3-(2-dimethylaminoethyl)anilino)-1-(4-(2-carboxyethyl)phenyl)methylene]-6-fluoro-2-indolinone
(88) 3-Z-[1-(3-(3-dimethylaminopropyl)anilino)-1-(4-(2-carboxyethyl)phenyl)methylene]-6-fluoro-2-indolinone
(89) 3-Z-[1-(4-(N-(dimethylaminocarbonylmethyl)-N-methylsulphonylamino)anilino)-1-(4-(2-carboxyethyl)phenyl)methylene]-6-fluoro-2-indolinone
(90) 3-Z-[1-(4-(N-methyl-N-methylsulphonylamino)anilino)-1-(4-(2-carboxyethyl)phenyl)methylene]-6-fluoro-2-indolinone
(91) 3-Z-[1-(4-(N-(N-(2-dimethylaminoethyl)-N-methylaminomethylcarbonyl)-N-methylamino)anilino)-1-(4-(2-carboxyethyl)phenyl)methylene]-6-fluoro-2-indolinone
(92) 3-Z-[1-(4-(2-diethylaminoethylsulphonyl)anilino)-1-(4-(2-carboxyethyl)phenyl)methylene]-6-fluoro-2-indolinone
(93) 3-Z-[1-(4-(2-dimethylaminoethoxy)anilino)-1-(4-(2-carboxyethyl)phenyl)methylene]-6-fluoro-2-indolinone
(94) 3-Z-[1-(4-(N-(3-dimethylaminopropylcarbonyl)-N-methylamino)anilino)-1-(4-(2-carboxyethyl)phenyl)methylene]-6-fluoro-2-indolinone
(95) 3-Z-[1-(4-(methylethylaminomethyl)anilino)-1-(4-(2-carboxyethyl)phenyl)methylene]-6-fluoro-2-indolinone
(96) 3-Z-[1-(4-(methylpropylaminomethyl)anilino)-1-(4-(2-carboxyethyl)phenyl)methylene]-6-fluoro-2-indolinone
(97) 3-Z-[1-(4-(methylbenzylaminomethyl)anilino)-1-(4-(2-carboxyethyl)phenyl)methylene]-6-fluoro-2-indolinone
(98) 3-Z-[1-(4-(azetidin-1-ylmethyl)anilino)-1-(4-(2-carboxyethyl)phenyl)methylene]-6-fluoro-2-indolinone
(99) 3-Z-(1-(4-(piperazin-1-ylmethyl)anilino)-1-(4-(2-carboxyethyl)phenyl)methylene]-6-fluoro-2-indolinone
(100) 3-Z-[1-(4-(morpholin-4-ylmethyl)anilino)-1-(4-(2-carboxyethyl)phenyl)methylene]-6-fluoro-2-indolinone
(101) 3-Z-[1-(4-(thiomorpholin-4-ylmethyl)anilino)-1-(4-(2-carboxyethyl)phenyl)methylene]-6-fluoro-2-indolinone
(102) 3-Z-[1-(4-(N-(2-dimethylaminoethyl)-N-acetylamino)anilino)-1-(3-(2-carboxyethyl)phenyl)methylene]-6-fluoro-2-indolinone
(103) 3-Z-[1-(4-(N-(2-methylaminoethyl)-N-acetylamino)anilino)-1-(3-(2-carboxyethyl)phenyl)methylene]-6-fluoro-2-indolinone
(104) 3-Z-[1-(4-(N-(3-methylaminopropyl)-N-acetylamino)anilino)-1-(3-(2-carboxyethyl)phenyl)methylene]-6-fluoro-2-indolinone
(105) 3-Z-[1-(4-(3-dimethylaminopropyl)anilino)-1-(3-(2-carboxyethyl)phenyl)methylene)-6-fluoro-2-indolinone
(106) 3-Z-[1-(4-ethylaminomethylanilino)-1-(3-(2-carboxyethyl)phenyl)methylene]-6-fluoro-2-indolinone
(107) 3-Z-[1-(4-(4-methylpiperazin-1-ylcarbonyl)anilino)-1-(3-(2-carboxyethyl)phenyl)methylene]-6-fluoro-2-indolinone
(108) 3-Z-[1-(4-(N-(3-dimethylaminopropyl)-N-methylsulphonylamino)anilino)-1-(3-(2-carboxyethyl)phenyl)methylene]-6-fluoro-2-indolinone
(109) 3-Z-[1-(4-(N-(2-dimethylaminoethyl)-N-propylsulphonylamino)anilino)-1-(3-(2-carboxyethyl)phenyl)methylene]-6-fluoro-2-indolinone
(110) 3-Z-[1-(3-(methylaminomethyl)anilino)-1-(3-(2-carboxyethyl)phenyl)methylene]-6-fluoro-2-indolinone
(111) 3-Z-[1-(3-(2-dimethylaminoethyl)anilino)-1-(3-(2-carboxyethyl)phenyl)methylene]-6-fluoro-2-indolinone
(112) 3-Z-[1-(3-(3-dimethylaminopropyl)anilino)-1-(3-(2-carboxyethyl)phenyl)methylene]-6-fluoro-2-indolinone
(113) 3-Z-[1-(4-(N-(dimethylaminocarbonylmethyl)-N-methylsulphonylamino)anilino)-1-(3-(2-carboxyethyl)phenyl)methylene]-6-fluoro-2-indolinone
(114) 3-Z-[1-(4-(N-methyl-N-methylsulphonylamino)anilino)-1-(3-(2-carboxyethyl)phenyl)methylene]-6-fluoro-2-indolinone
(115) 3-Z-[1-(4-(N-methyl-N-acetylamino)anilino)-1-(3-(2-carboxyethyl)phenyl)methylene]-6-fluoro-2-indolinone
(116) 3-Z-[1-(4-(N-(N-(2-dimethylaminoethyl)-N-methylaminomethylcarbonyl)-N-methylamino)anilino)-1-(3-(2-carboxyethyl)phenyl)methylene]-6-fluoro-2-indolinone
(117) 3-Z-[1-(4-(2-diethylaminoethylsulphonyl)anilino)-1-(3-(2-carboxyethyl)phenyl)methylene]-6-fluoro-2-indolinone
(118) 3-Z-[1-(4-(N-(2-dimethylaminoethylcarbonyl)-N-methylamino)anilino)-1-(3-(2-carboxyethyl)phenyl)methylene]-6-fluoro-2-indolinone
(119) 3-Z-[1-(4-(N-(2-dimethylaminoethyl)-N-methylaminomethyl)anilino)-1-(3-(2-carboxyethyl)phenyl)methylene]-6-fluoro-2-indolinone
(120) 3-Z-[1-(4-(2-dimethylaminoethoxy)anilino)-1-(3-(2-carboxyethyl)phenyl)methylene]-6-fluoro-2-indolinone
(121) 3-Z-[1-(4-(methylethylaminomethyl)anilino)-1-(3-(2-carboxyethyl)phenyl)methylene]-6-fluoro-2-indolinone
(122) 3-Z-[1-(4-(methylpropylaminomethyl)anilino)-1-(3-(2-carboxyethyl)phenyl)methylene]-6-fluoro-2-indolinone
(123) 3-Z-[1-(4-(methylbenzylaminomethyl)anilino)-1-(3-(2-carboxyethyl)phenyl)methylene]-6-fluoro-2-indolinone
(124) 3-Z-[1-(4-(diethylaminomethyl)anilino)-1-(3-(2-carboxyethyl)phenyl)methylene]-6-fluoro-2-indolinone
(125) 3-Z-[1-(4-(pyrrolidin-1-ylmethyl)anilino)-1-(3-(2-carboxyethyl)phenyl)methylene]-6-fluoro-2-indolinone
(126) 3-Z-[1-(4-(azetidin-1-ylmethyl)anilino)-1-(3-(2-carboxyethyl)phenyl)methylene]-6-fluoro-2-indolinone (127) 3-Z-[1-(4-(piperazin-1-ylmethyl)anilino)-1-(3-(2-carboxyethyl)phenyl)methylene]-6-fluoro-2-indolinone
(128) 3-Z-[1-(4-(morpholin-4-ylmethyl)anilino)-1-(3-(2-carboxyethyl)phenyl)methylene]-6-fluoro-2-indolinone
(129) 3-Z-[1-(4-(thiomorpholin-4-ylmethyl)anilino)-1-(3-(2-carboxyethyl)phenyl)methylene]-6-fluoro-2-indolinone
(130) 3-Z-[1-(4-(N-(2-dimethylaminoethyl)-N-methylsulphonylamino)anilino)-1-(4-(2-carboxyethyl)phenyl)methylene]-6-bromo-2-indolinone
(131) 3-Z-[1-(4-(N-(dimethylaminomethylcarbonyl)-N-methylamino)anilino)-1-(4-(2-carboxyethyl)phenyl)methylene]-6-bromo-2-indolinone
(132) 3-Z-[1-(4-(N-(2-dimethylaminoethyl)-N-acetylamino)anilino)-1-(4-(2-carboxyethyl)phenyl)methylene]-6-bromo-2-indolinone
(133) 3-Z-[1-(4-(N-(2-methylaminoethyl)-N-acetylamino)anilino)-1-(4-(2-carboxyethyl)phenyl)methylene]-6-bromo-2-indolinone
(134) 3-Z-[1-(4-(N-(3-dimethylaminopropyl)-N-acetylamino)anilino)-1-(4-(2-carboxyethyl)phenyl)methylene]-6-bromo-2-indolinone
(135) 3-Z-[1-(4-(N-(3-methylaminopropyl)-N-acetylamino)anilino)-1-(4-(2-carboxyethyl)phenyl)methylene]-6-bromo-2-indolinone
(136) 3-Z-[1-(4-(3-dimethylaminopropyl)anilino)-1-(4-(2-carboxyethyl)phenyl)methylene]-6-bromo-2-indolinone
(137) 3-Z-[1-(4-ethylaminomethylanilino)-1-(4-(2-carboxyethyl)phenyl)methylene]-6-bromo-2-indolinone
(138) 3-Z-[1-(4-methylaminomethylanilino)-1-(4-(2-carboxyethyl)phenyl)methylene]-6-bromo-2-indolinone
(139) 3-Z-[1-(4-(N-(4-methylpiperazin-1-ylmethylcarbonyl)-N-methylamino)anilino)-1-(4-(2-carboxyethyl)phenyl)methylene]-6-bromo-2-indolinone
(140) 3-Z-[1-(4-(4-methylpiperazin-1-ylcarbonyl)anilino)-1-(4-(2-carboxyethyl)phenyl)methylene]-6-bromo-2-indolinone
(141) 3-Z-[1-(4-(N-(3-dimethylaminopropyl)-N-methylsulphonylamino)anilino)-1-(4-(2-carboxyethyl)phenyl)methylene]-6-bromo-2-indolinone
(142) 3-Z-[1-(4-(N-(2-dimethylaminoethyl)-N-propylsulphonylamino)anilino)-1-(4-(2-carboxyethyl)phenyl)methylene]-6-bromo-2-indolinone
(143) 3-Z-1-(4-aminomethylanilino)-1-(4-(2-carboxyethyl)phenyl)methylene]-6-bromo-2-indolinone
(144) 3-Z-[1-(3-(dimethylaminomethyl)anilino)-1-(4-(2-carboxyethyl)phenyl)methylene]-6-bromo-2-indolinone
(145) 3-Z-[1-(3-(methylaminomethyl)anilino)-1-(4-(2-carboxyethyl)phenyl)methylene]-6-bromo-2-indolinone
(146) 3-Z-[1-(3-(2-dimethylaminoethyl)anilino)-1-(4-(2-carboxyethyl)phenyl)methylene]-6-bromo-2-indolinone
(147) 3-Z-[1-(1-(3-(3-dimethylaminopropyl)anilino)-1-(4-(2-carboxyethyl)phenyl)methylene]-6-bromo-2-indolinone
(148) 3-Z-[1-(4-(2-dimethylaminoethyl)anilino)-1-(4-(2-carboxyethyl)phenyl)methylene]-6-bromo-2-indolinone
(149) 3-Z-[1-(4-(N-(dimethylaminocarbonylmethyl)-N-methylsulphonylamino)anilino)-1-(4-(2-carboxyethyl)phenyl)methylene]-6-bromo-2-indolinone
(150) 3-Z-[1-(4-(N-methyl-N-methylsulphonylamino)anilino)-1-(4-(2-carboxyethyl)phenyl)methylene]-6-bromo-2-indolinone
(151) 3-Z-[1-(4-(N-methyl-N-acetylamino)anilino)-1-(4-(2-carboxyethyl)phenyl)methylene]-6-bromo-2-indolinone
(152) 3-Z-[1-(4-(1-methylimidazol-2-yl)anilino)-1-(4-(2-carboxyethyl)phenyl)methylene]-6-bromo-2-indolinone
(153) 3-Z-[1-(4-(N-(N-(2-dimethylaminoethyl)-N-methylaminomethylcarbonyl)-N-methylamino)anilino)-1-(4-(2-carboxyethyl)phenyl)methylene]-6-bromo-2-indolinone
(154) 3-Z-[1-(4-(2-diethylaminoethylsulphonyl)anilino)-1-(4-(2-carboxyethyl)phenyl)methylene]-6-bromo-2-indolinone
(155) 3-Z-[1-(4-(N-(2-dimethylaminoethylcarbonyl)-N-methylamino)anilino)-1-(4-(2-carboxyethyl)phenyl)methylene]-6-bromo-2-indolinone
(156) 3-Z-[1-(4-(N-(2-dimethylaminoethyl)-N-methylaminomethyl)anilino)-1-(4-(2-carboxyethyl)phenyl)methylene]-6-bromo-2-indolinone
(157) 3-Z-[1-(4-(2-dimethylaminoethoxy)anilino)-1-(4-(2-carboxyethyl)phenyl)methylene]-6-bromo-2-indolinone
(158) 3-Z-[1-(4-(N-(4-dimethylaminobutylcarbonyl)-N-methylamino)anilino)-1-(4-(2-carboxyethyl)phenyl)methylene]-6-bromo-2-indolinone
(159) 3-Z-[1-(4-(N-(3-dimethylaminopropylcarbonyl)-N-methylamino)anilino)-1-(4-(2-carboxyethyl)phenyl)methylene]-6-bromo-2-indolinone
(160) 3-Z-[1-(4-(methylethylaminomethyl)anilino)-1-(4-(2-carboxyethyl)phenyl)methylene]-6-bromo-2-indolinone
(161) 3-Z-[1-(4-(methylpropylaminomethyl)anilino)-1-(4-(2-carboxyethyl)phenyl)methylene]-6-bromo-2-indolinone
(162) 3-Z-[1-(4-(methylbenzylaminomethyl)anilino)-1-(4-(2-carboxyethyl)phenyl)methylene]-6-bromo-2-indolinone
(163) 3-Z-[1-(4-(diethylaminomethyl)anilino)-1-(4-(2-carboxyethyl)phenyl)methylene]-6-bromo-2-indolinone
(164) 3-Z-[1-(4-(N-(2-dimethylaminoethyl)-N-methylaminomethyl)anilino)-1-(4-(2-carboxyethyl)-phenylmethylene]-6-bromo-2-indolinone
(165) 3-Z-[1-(4-(pyrrolidin-1-ylmethyl)anilino)-1-(4-(2-carboxyethyl)phenyl)methylene]-6-bromo-2-indolinone
(166) 3-Z-[1-(4-(azetidin-1-ylmethyl)anilino)-1-(4-(2-carboxyethyl)phenyl)methylene]-6-bromo-2-indolinone
(167) 3-Z-[1-(4-((4-methylpiperazin-1-yl)methyl)anilino)-1-(4-(2-carboxyethyl)phenyl)methylene]-6-bromo-2-indolinone
(168) 3-Z-[1-(4-(piperazin-1-ylmethyl)anilino)-1-(4-(2-carboxyethyl)phenyl)methylene]-6-bromo-2-indolinone
(169) 3-Z-[1-(4-(morpholin-4-ylmethyl)anilino)-1-(4-(2-carboxyethyl)phenyl)methylene]-6-bromo-2-indolinone
(170) 3-Z-[1-(4-(thiomorpholin-4-ylmethyl)anilino)-1-(4-(2-carboxyethyl)phenyl)methylene]-6-bromo-2-indolinone
(171) 3-Z-[1-(4-(imidazol-1-ylmethyl)anilino)-1-(4-(2-carboxyethyl)phenyl)methylene]-6-bromo-2-indolinone
(172) 3-Z-[1-(4-dimethylaminomethylanilino)-1-(3-(2-carboxyethyl)phenyl)methylene]-6-bromo-2-indolinone
(173) 3-Z-[1-(4-(N-(2-dimethylaminoethyl)-N-methylsulphonylamino)anilino)-1-(3-(2-carboxyethyl)phenyl)methylene]-6-bromo-2-indolinone
(174) 3-Z-[1-(4-(N-(dimethylaminomethylcarbonyl)-N-methylamino)anilino)-1-(3-(2-carboxyethyl)phenyl)methylene]-6-bromo-2-indolinone
(175) 3-Z-[1-(4-(N-(2-dimethylaminoethyl)-N-acetylamino)anilino)-1-(3-(2-carboxyethyl)phenyl)methylene]-6-bromo-2-indolinone
(176) 3-Z-[1-(4-(N-(2-methylaminoethyl)-N-acetylamino)anilino)-1-(3-(2-carboxyethyl)phenyl)methylene]-6-bromo-2-indolinone
(177) 3-Z-[1-(4-(N-(3-dimethylaminopropyl)-N-acetylamino)anilino)-1-(3-(2-carboxyethyl)phenyl)methylene]-6-bromo-2-indolinone (178) 3-Z-[1-(4-(N-(3-methylaminopropyl)-N-acetylamino)anilino)-1-(3-(2-carboxyethyl)phenyl)methylene]-6-bromo-2-indolinone
(179) 3-Z-[1-(4-(3-dimethylaminopropyl)anilino)-1-(3-(2-carboxyethyl)phenyl)methylene]-6-bromo-2-indolinone
(180) 3-Z-[1-(4-ethylaminomethylanilino)-1-(3-(2-carboxyethyl)phenyl)methylene]-6-bromo-2-indolinone
(181) 3-Z-[1-(4-methylaminomethylanilino)-1-(3-(2-carboxyethyl)phenyl)methylene]-6-bromo-2-indolinone
(182) 3-Z-[1-(4-(N-(4-methylpiperazin-1-ylmethylcarbonyl)-N-methylamino)anilino)-1-(3-(2-carboxyethyl)phenyl)methylene]-6-bromo-2-indolinone
(183) 3-Z-[1-(4-(4-methylpiperazin-1-ylcarbonyl)anilino)-1-(3-(2-carboxyethyl)phenyl)methylene]-6-bromo-2-indolinone
(184) 3-Z-[1-(4-(N-(3-dimethylaminopropyl)-N-methylsulphonylamino)anilino)-1-(3-(2-carboxyethyl)phenyl)methylene]-6-bromo-2-indolinone
(185) 3-Z-[1-(4-(N-(2-dimethylaminoethyl)-N-propylsulphonylamino)anilino)-1-(3-(2-carboxyethyl)phenyl)methylene]-6-bromo-2-indolinone
(186) 3-Z-[1-(4-aminomethylanilino)-1-(3-(2-carboxyethyl)phenyl)methylene]-6-bromo-2-indolinone
(187) 3-Z-[1-(3-(dimethylaminomethyl)anilino)-1-(3-(2-carboxyethyl)phenyl)methylene]-6-bromo-2-indolinone
(188) 3-Z-[1-(3-(methylaminomethyl)anilino)-1-(3-(2-carboxyethyl)phenyl)methylene]-6-bromo-2-indolinone
(189) 3-Z-[1-(3-(2-dimethylaminoethyl)anilino)-1-(3-(2-carboxyethyl)phenyl)methylene]-6-bromo-2-indolinone
(190) 3-Z-[1-(3-(3-dimethylaminopropyl)anilino)-1-(3-(2-carboxyethyl)phenyl)methylene]-6-bromo-2-indolinone
(191) 3-Z-[1-(4-(2-dimethylaminoethyl)anilino)-1-(3-(2-carboxyethyl)phenyl)methylene]-6-bromo-2-indolinone
(192) 3-Z-[1-(4-(N-(dimethylaminocarbonylmethyl)-N-methylsulphonylamino)anilino)-1-(3-(2-carboxyethyl)phenyl)methylene]-6-bromo-2-indolinone
(193) 3-Z-[1-(4-(N-methyl-N-methylsulphonylamino)anilino)-1-(3-(2-carboxyethyl)phenyl)methylene]-6-bromo-2-indolinone
(194) 3-Z-[1-(4-(N-methyl-N-acetylamino)anilino)-1-(3-(2-carboxyethyl)phenyl)methylene]-6-bromo-2-indolinone
(195) 3-Z-[1-(4-(1-methylimidazol-2-yl)anilino)-1-(3-(2-carboxyethyl)phenyl)methylene]-6-bromo-2-indolinone
(196) 3-Z-[1-(4-(N-(N-(2-dimethylaminoethyl)-N-methylaminomethylcarbonyl)-N-methylamino)anilino)-1-(3-(2-carboxyethyl)phenyl)methylene]-6-bromo-2-indolinone
(197) 3-Z-[1-(4-(2-diethylaminoethylsulphonyl)anilino)-1-(3-(2-carboxyethyl)phenyl)methylene]-6-bromo-2-indolinone
(198) 3-Z-[1-(4-(N-(2-dimethylaminoethylcarbonyl)-N-methylamino)anilino)-1-(3-(2-carboxyethyl)phenyl)methylene]-6-bromo-2-indolinone
(199) 3-Z-[1-(4-(N-(2-dimethylaminoethyl)-N-methylaminomethyl)anilino)-1-(3-(2-carboxyethyl)phenyl)methylene]-6-bromo-2-indolinone
(200) 3-Z-[1-(4-(2-dimethylaminoethoxy)anilino)-1-(3-(2-carboxyethyl)phenyl)methylene]-6-bromo-2-indolinone
(201) 3-Z-[1-(4-(N-(4-dimethylaminobutylcarbonyl)-N-methylamino)anilino)-1-(3-(2-carboxyethyl)phenyl)methylene]-6-bromo-2-indolinone
(202) 3-Z-[1-(4-(N-(3-dimethylaminopropylcarbonyl)-N-methylamino)anilino)-1-(3-(2-carboxyethyl)phenyl)methylene]-6-bromo-2-indolinone
(203) 3-Z-[1-(4-(methylethylaminomethyl)anilino)-1-(3-(2-carboxyethyl)phenyl)methylene]-6-bromo-2-indolinone
(204) 3-Z-[1-(4-(methylpropylaminomethyl)anilino)-1-(3-(2-carboxyethyl)phenyl)methylene]-6-bromo-2-indolinone
(205) 3-Z-[1-(4-(methylbenzylaminomethyl)anilino)-1-(3-(2-carboxyethyl)phenyl)methylene]-6-bromo-2-indolinone
(206) 3-Z-[1-(4-(diethylaminomethyl)anilino)-1-(3-(2-carboxyethyl)phenyl)methylene]-6-bromo-2-indolinone
(207) 3-Z-[1-(4-(N-(2-dimethylaminoethyl)-N-methylaminomethyl)anilino)-1-(3-(2-carboxyethyl)phenylmethylene]-6-bromo-2-indolinone
(208) 3-Z-[1-(4-(pyrrolidin-1-ylmethyl)anilino)-1-(3-(2-carboxyethyl)phenyl)methylene]-6-bromo-2-indolinone
(209) 3-Z-[1-(4-(azetidin-1-ylmethyl)anilino)-1-(3-(2-carboxyethyl)phenyl)methylene]-6-bromo-2-indolinone
(210) 3-Z-[1-(4-((4-methylpiperazin-1-yl)methyl)anilino)-1-(3-(2-carboxyethyl)phenyl)methylene]-6-bromo-2-indolinone
(211) 3-Z-[1-(4-(piperazin-1-ylmethyl)anilino)-1-(3-(2-carboxyethyl)phenyl)methylene]-6-bromo-2-indolinone
(212) 3-Z-[1-(4-(morpholin-4-ylmethyl)anilino)-1-(3-(2-carboxyethyl)phenyl)methylene]-6-bromo-2-indolinone
(213) 3-Z-[1-(4-(thiomorpholin-4-ylmethyl)anilino)-1-(3-(2-carboxyethyl)phenyl)methylene]-6-bromo-2-indolinone
(214) 3-Z-[1-(4-(imidazol-1-yl methyl)anilino)-1-(3-(2-carboxyethyl)phenyl)methylene]-6-bromo-2-indolinone
(215) 3-Z-[1-(4-dimethylaminomethylanilino)-1-(4-carboxymethylaminophenyl)-methylene]-6-fluoro-2-indolinone
(216) 3-Z-[1-(4-dimethylaminomethylanilino)-1-(3-carboxymethylamino-phenyl)-methylene]-6-fluoro-2-indolinone
(217) 3-Z-[1-(4-dimethylaminomethylanilino)-1-(4-(N-methyl-carboxymethylamino)phenyl)methylene]-6-fluoro-2-indolinone
(218) 3-Z-[1-(4-dimethylaminomethylanilino)-1-(3-(N-methyl-carboxymethylamino)phenyl)methylene]-6-fluoro-2-indolinone
(219) 3-Z-[1-(4-dimethylaminomethylanilino)-1-(4-carboxymethoxyphenyl)-methylene]-6-chloro-2-indolinone
(220) 3-Z-[1-(4-dimethylaminomethylanilino)-1-(3-carboxymethoxyphenyl)-methylene]-6-chloro-2-indolinone
(221) 3-Z-[1-(4-dimethylaminomethylanilino)-1-(4-carboxymethylaminophenyl)-methylene]-6-chloro-2-indolinone
(222) 3-Z-[1-(4-dimethylaminomethylanilino)-1-(3-carboxymethylaminophenyl)-methylene]-6-chloro-2-indolinone
(223) 3-Z-[1-(4-dimethylaminomethylanilino)-1-(4-(N-methyl-carboxymethylamino)phenyl)methylene]-6-chloro-2-indolinone
(224) 3-Z-[1-(4-dimethylaminomethylanilino)-1-(3-(N-methyl-carboxymethylamino)phenyl)methylene]-6-chloro-2-indolinone
(225) 3-Z-[1-(4-dimethylaminomethylanilino)-1-(4-carboxymethoxyphenyl)-methylene]-6-bromo-2-indolinone
(226) 3-Z-[1-(4-dimethylaminomethylanilino)-1-(3-carboxymethoxyphenyl)-methylene]-6-bromo-2-indolinone
(227) 3-Z-[1-(4-dimethylaminomethylanilino)-1-(4-carboxymethylaminophenyl)-methylene]-6-bromo-2-indolinone
(228) 3-Z-[1-(4-dimethylaminomethylanilino)-1-(3-carboxymethylaminophenyl)-methylene]-6-bromo-2-indolinone (229) 3-Z-[1-(4-dimethylaminomethylanilino)-1-(4-(N-methyl-carboxymethylamino)phenyl)methylene]-6-bromo-2-indolinone (230) 3-Z-[1-(4-dimethylaminomethylanilino)-1-(3-(N-methyl-carboxymethylamino)phenyl)methylene]-6-bromo-2-indolinone In the tables above,
Me is methyl,
Et is ethyl,
Pr is propyl,
nPr is n-propyl,
iPr is isopropyl,
nBu is n-butyl,
tBu is tert-butyl and
Bn is benzyl.

What is claimed is:
1. A compound of the formula

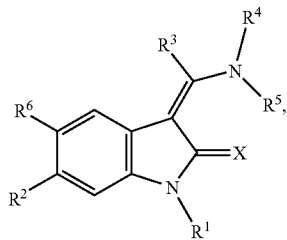

in which
X is an oxygen atom,
$R^1$ is a hydrogen atom,
$R^2$ is a fluorine, chlorine or bromine atom or a cyano group,
$R^3$ is a phenyl group which is substituted by a carboxy-$C_{1-3}$-alkyl or $C_{1-4}$-alkoxy-carbonyl-$C_{1-3}$-alkyl group
$R^4$ is a phenyl group which is monosubstituted
by a $C_{1-3}$-alkyl group which is terminally substituted by di-($C_{1-2}$-alkyl)-amino-, imidazol-1-yl, pyrrolidin-1-yl,
1-($C_{1-3}$-alkyl)imidazol-2-yl, or
by a group of the formula

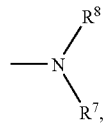

in which
$R^7$ is a $C_{1-2}$-alkyl, $C_{1-2}$-alkyl-carbonyl, or $C_{1-3}$-alkyl-sulphonyl group and
$R^8$ is ω-[di-($C_{1-2}$-alkyl)-amino]-$C_{2-3}$-alkyl, or
a ($C_{1-3}$-alkyl)-carbonyl group which is terminally substituted by a di-($C_{1-2}$-alkyl)-amino, piperazin-1-yl or 4-($C_{1-3}$-alkyl)-piperazin-1-yl group,
where all dialkylamino groups present in the radical $R^4$ may also be present in quaternized form, for example as an N-methyl-(N,N-dialkyl)-ammonium group, where the counterion is preferably selected from the group consisting of iodide, chloride, bromide, methylsulphonate, para-toluenesulphonate and trifluoroacetate,
$R^5$ is a hydrogen atom and
$R^6$ is a hydrogen atom,
where the abovementioned alkyl groups include linear and branched alkyl groups in which additionally one to 3 hydrogen atoms may be replaced by fluorine atoms,
where additionally a carboxyl, amino or imino group present may be substituted by an in vivo cleavable radical or may be present in the form of a prodrug radical, for example in the form of a group which can be converted in vivo into a carboxyl group or in the form of a group which can be converted in vivo into an imino or amino group,
or a salt thereof.

2. A compound of the formula I according to claim 1, selected from the following group:
(a) 3-Z-[1-(4-dimethylaminomethylanilino)-1-(3-(2-carboxyethyl)phenyl)methylene]-6-chloro-2-indolinone
(b) 3-Z-[1-(4-dimethylaminomethylanilino)-1-(4-(2-carboxyethyl)phenyl)methylene]-6-fluoro-2-indolinone
(c) 3-Z-[1-(4-dimethylaminomethylanilino)-1-(3-(2-carboxyethyl)phenyl)methylene]-6-fluoro-2-indolinone
(d) 3-Z-[1-(4-(diethylaminomethyl)anilino)-1-(4-(2-carboxyethyl)phenyl)methylene]-6-fluoro-2-indolinone
(e) 3-Z-[1-(4-(2-dimethylaminoethyl)anilino)-1-(4-(2-carboxyethyl)phenyl)methylene]-6-chloro-2-indolinone
(f) 3-Z-[1-(4-dimethylaminomethylanilino)-1-(4-(2-carboxyethyl)phenyl)methylene]-6-chloro-2-indolinone
(g) 3-Z-[1-(4-(dimethylaminomethyl)anilino)-1-(4-(2-carboxyethyl)phenyl)methylene]-6-bromo-2-indolinone
(h) 3-Z-[1-(4-(dimethylaminomethyl)anilino)-1-(4-(2-carboxyethyl)-methylene]-6-bromo-2-indolinone, and
(i) 3-Z-[1-(4-dimethylaminomethylanilino)-1-(4-(2-ethoxycarbonylethyl)phenyl)methylene]-6-fluoro-2-indolinone
or a salt of any of the above recited compounds.

3. The compound of formula I according to claim 2

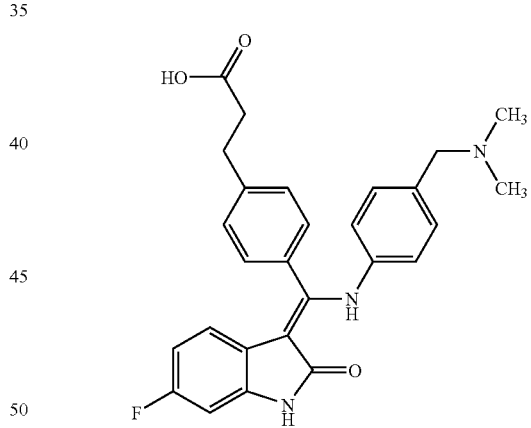

3-Z-[1-(4-dimethylaminomethylanilino)-1-(4-(2-carboxyethyl)phenyl)methylene]-6-fluoro-2-indolinone
or a salt thereof.

4. A compound having the following formula and name:
1-acetyl-6-fluoro-2-indolinone

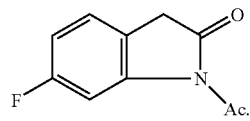

* * * * *